United States Patent [19]
Wrighton et al.

[11] Patent Number: 5,830,851
[45] Date of Patent: Nov. 3, 1998

[54] METHODS OF ADMINISTERING PEPTIDES THAT BIND TO THE ERYTHROPOIETIN RECEPTOR

[75] Inventors: Nicholas C. Wrighton, Palo Alto; William J. Dower, Menlo Park; Ray S. Chang, Colma; Arun K. Kashyap, Fremont, all of Calif.

[73] Assignee: Affymax Technologies N.V., Greenford, England

[21] Appl. No.: 484,631

[22] Filed: Jun. 7, 1995

Related U.S. Application Data

[63] Continuation-in-part of Ser. No. 155,940, Nov. 19, 1993, abandoned.

[51] Int. Cl.$^6$ .............................. A61K 38/04; C07K 7/04; C12N 15/00
[52] U.S. Cl. .................................. 514/2; 514/8; 514/12; 514/13; 514/14; 514/15; 435/69.1
[58] Field of Search .............................. 514/2, 8, 12, 13, 514/14, 15; 435/69.1

[56] References Cited

U.S. PATENT DOCUMENTS

| | | | |
|---|---|---|---|
| 4,677,195 | 6/1987 | Hewick | 530/397 |
| 4,703,008 | 10/1987 | Lin | 435/240.2 |
| 5,106,954 | 4/1992 | Fibi | 530/324 |
| 5,278,065 | 1/1994 | D'Andrea | 435/252.3 |
| 5,322,837 | 6/1994 | Hewick et al. | 514/8 |
| 5,369,014 | 11/1994 | Brugnara et al. | 435/29 |
| 5,399,551 | 3/1995 | Ise et al. | 514/8 |
| 5,482,924 | 1/1996 | Royet et al. | 514/8 |

FOREIGN PATENT DOCUMENTS

| | | |
|---|---|---|
| 2021528 | 1/1991 | Canada . |
| 0 427 189 | 5/1991 | European Pat. Off. . |
| 0 428 267 | 5/1991 | European Pat. Off. . |
| WO 90/08822 | 8/1990 | WIPO . |
| WO 91/05867 | 5/1991 | WIPO . |
| WO 93/25221 | 12/1993 | WIPO . |
| WO 94/02611 | 2/1994 | WIPO . |
| 9640749 | 12/1996 | WIPO .............................. C07K 7/00 |
| 9640772 | 12/1996 | WIPO .......................... C07K 14/505 |

OTHER PUBLICATIONS

Barker, Peter L., et al. (1992) "Cyclic RGD Peptide Analogues as Antiplatelet Antithrombotics", *J. Med. Chem.*, 35:2040–2048.

Or, Yat Sun, et al. (1991) "Cysteine Alkylation in Unprotected Peptides: Synthesis of a Carbavasopressin Analogue by Intramolecular Cysteine Alkylation", *J. Org. Chem.* 56:3146–3149.

Sawyer, Stephen T., et al. (1987) "Binding and Receptor-mediated Endocytosis of Erythropoietin in Friend Virus-infected Erythroid Cells", *The Journal of Biological Chemistry*, 262(12):5554–5562.

Sasaki, Hiroshi, et al. (1987) "Carbohydrate Structure of Erythropoietin Expressed in Chinese Hamster Ovary Cells by a Human Erythorpoietin cDNA", *The Journal of Biological Chemistry*, 262(25):12059–12076.

Sawyer, Stephen, T., et al. (1987) "Identification of the receptor for erythropoietin by cross–linking to Friend virus-infected erythroid cells", *Proc. Natl. Acad. Sci. USA*, 84:3690–3694.

Landschulz, Katherine T., et al. (1989) "Erythropoietin Receptors on Murine Erythroid Colony–Forming Units: Natural History", *Blood*, 73(6):1476–1486.

Kitamura, Toshio, et al. (1989) "Identification and Analysis of Human Erythropoietin Receptors on a Factor–Dependent Cell Line, TF–1", *Blood*, 73(2):375–380.

Krystal, Gerald (1983) "A Simple Microassay for Erythropoietin Based on $^3$H–Thymidine Incorporation into Spleen Cells from Phenylhydrazine Treated Mice", *Exp. Hematol.*, 11(7):649–660.

Cwirla, Steven E., et al. (1990) "Peptides on phage: A vast library of peptides for identifying ligands", *Proc. Natl. Acad. Sci. USA*, 87:6378–6382.

Bowie, James U., et al. (1990) "Deciphering the Message in Protein Sequences: Tolerance to Amino Acid Substitutions", *Science*, 247:1306–1310.

*Primary Examiner*—Stephen Walsh
*Assistant Examiner*—Elizabeth C. Kemmerer
*Attorney, Agent, or Firm*—Eugenia Garrett-Wackowski; Lauren L. Stevens

[57] ABSTRACT

Peptides of 10 to 40 or more amino acid residues in length and having the sequence $X_3X_4X_5GPX_6TWX_7X_8$ (SEQ ID NO:252) where each amino acid is indicated by standard one letter abbreviation; $X_3$ is C; $X_4$ is R, H, L, or W; $X_5$ is M, F, or I; $X_6$ is independently selected from any one of the 20 genetically coded L-amino acids; $X_7$ is D, E, I, L, or V; and $X_8$ is C, which bind and activate the erythropoietin receptor (EPO-R) or otherwise act as an EPO agonist, and methods for their use.

7 Claims, 17 Drawing Sheets

RIGPITWV (SEQ ID NO: 237) MUTAGENESIS OLIGO

```
                ↓                        | 70/10/10/10
    C TCT CAC TCC GGA GGC NNK NNK NNK TGT cgK atK ggK ccK atK acK
        |
    tgK gtK TGT NNK NNK NNK GGA GGC GGG GGT AGC ACT GTT GAA

AGT TGT   (SEQ ID NO: 238)
```

FIG. 1.

| | |
|---|---|
| GGTYRCSMGPMTWVCLPMGG | SEQ ID NO: 203 |
| GGMYSCRMGPMTWVCGPSGG | SEQ ID NO: 204 |
| GGWAWCRMGPITWVCSAHGG | SEQ ID NO: 205 |
| GGMYSCRMGPMTWVCIPYGG | SEQ ID NO: 206 |
| GGEYKCYMGPITWVCKPEGG | SEQ ID NO: 55 |
| GGDYTCRMGPMTWICTATGG | SEQ ID NO: 207 |
| GGNYLCRFGPTWDCTGFRG | SEQ ID NO: 208 |
| GGNYVCRMGPITWICTPAGG | SEQ ID NO: 34 |
| GGKDVCRMGPITWDCRSTGG | SEQ ID NO: 209 |
| GGSYLCRMGPTTWLCTAQRGGGN | SEQ ID NO: 58 |
| GGNYLCRMGPATWVCGRMGG | SEQ ID NO: 210 |
| GGEYKCRMGPLTWVCQYAGG | SEQ ID NO: 211 |
| GGDYTCRMGPMTWICTATRG | SEQ ID NO: 36 |
| GGVYVCRMGPLTWECTASGG | SEQ ID NO: 212 |
| GGEYSCRMGPMTWVCSPTGG | SEQ ID NO: 213 |
| GGEYLCRMGPITWVCERYGG | SEQ ID NO: 31 |
| GGNYICRMGPMTWVCTAHGG | SEQ ID NO: 214 |
| GGDYLCRMGPATWVCGRMGG | SEQ ID NO: 215 |
| GGLYLCRFGPVTWDCGYKGG | SEQ ID NO: 7 |
| GGLYSCRMGPITWVCTKAGG | SEQ ID NO: 216 |
| GGGYHCRMGPMTWVCRPVGG | SEQ ID NO: 217 |
| GGTYSCHFGPLTWVCKPQGG | SEQ ID NO: 8 |
| GGIYKCLMGPLTWVCTPDGG | SEQ ID NO: 27 |
| GGLYSCLMGPITWLCKPKGG | SEQ ID NO: 218 |
| GGDYHCRMGPLTWVCKPLGG | SEQ ID NO: 9 |
| GGDYSCRMGPTTWVCTPPGG | SEQ ID NO: 219 |
| GGDYWCRMGPSTWECNAHGG | SEQ ID NO: 220 |
| GGKYLCSFGPITWVCARYGG | SEQ ID NO: 221 |
| GGLYKCRLGPITWVCSPLGG | SEQ ID NO: 222 |
| GGSYTCRFGPETWVCRPNGG | SEQ ID NO: 223 |
| GGSYSCRMGPITWVCKPGGG | SEQ ID NO: 224 |
| GGSYTCRMGPITWVCLPAGG | SEQ ID NO: 225 |
| GGLYECRMGPMTWVCRPGGG | SEQ ID NO: 41 |

FIG. 2-1.

| | |
|---|---|
| GGDYTCRMGPITWICTKAGG | SEQ ID NO: 226 |
| GGVYSCRMGPTTWECNRYVG | SEQ ID NO: 227 |
| GGAYLCHMGPITWVCRPQGG | SEQ ID NO: 228 |
| GGEYSCRMGPNTWVCKPVGG | SEQ ID NO: 229 |
| GGLYLCRMGPVTWECQPRGG | SEQ ID NO: 24 |
| GGLYTCRMGPITWVCLLPGG | SEQ ID NO: 230 |
| GGLYTCRMGPVTWVCTGAGG | SEQ ID NO: 231 |
| GGVYKCRMGPLTWECRPTGG | SEQ ID NO: 232 |
| GGDYNCRFGPLTWVCKPSGG | SEQ ID NO: 37 |
| GGSYLCRFGPTTWLCSSAGG | SEQ ID NO: 233 |
| GGSYLCRMGPTTWVCTRMGG | SEQ ID NO: 234 |
| GGSYLCRFGPTTWLCTQRGG | SEQ ID NO: 235 |
| GGWVTCRMGPITWVCGVHGG | SEQ ID NO: 22 |
| GGQLLCGIGPITWVCRWVGG | SEQ ID NO: 23 |
| GGKYSCFMGPTTWVCSPVGRGV | SEQ ID NO: 25 |
| GGWVYCRIGPITWVCDTNGG | SEQ ID NO: 26 |
| GGMYYCRMGPMTWVCKGAGG | SEQ ID NO: 28 |
| GGTTQCWIGPITWVCRARGG | SEQ ID NO: 29 |
| GGPYHCRMGPITWVCGPVGG | SEQ ID NO: 30 |
| GGEYRCRMGPISWVCSPQGG | SEQ ID NO: 32 |
| GGNYTCRFGPLTWECTPQGGGA | SEQ ID NO: 33 |
| GGSWDCRIGPITWVCKWSGG | SEQ ID NO: 35 |
| VGNYMCHFGPITWVCRPGGG | SEQ ID NO: 10 |
| GGLYLCRMGPQTWMCQPGGG | SEQ ID NO: 39 |
| GGDYVCRMGPMTWVCAPYGR | SEQ ID NO: 40 |
| GGWYSCLMGPMTWVCKAHRG | SEQ ID NO: 42 |
| GGKYYCWMGPMTWVCSPAGG | SEQ ID NO: 43 |
| GGYVMCRIGPITWVCDIPGG | SEQ ID NO: 44 |
| GSCLQCCIGPITWVCRHAGG | SEQ ID NO: 45 |
| GGNYFCRMGPITWVCQRSVG | SEQ ID NO: 46 |
| GGEYICRMGPLTWECKRTGG | SEQ ID NO: 47 |
| GGLYACRMGPITWVCKYMAG | SEQ ID NO: 48 |
| GGQYLCTFGPITWLCRGAGG | SEQ ID NO: 236 |
| GGVYACRMGPITWVCSPLGG | SEQ ID NO: 11 |
| GGYTTCRMGPITWVCSAHGG | SEQ ID NO: 50 |
| GGTYKCWMGPMTWVCRPVGG | SEQ ID NO: 51 |
| GGNYYCRFGPITFECHPTGG | SEQ ID NO: 53 |
| GGLYACHMGPMTWVCQPLRG | SEQ ID NO: 14 |
| GGEYLCRMGPMTWVCTPVGG | SEQ ID NO: 57 |
| GGLYTCRMGPITWVCLPAGG | SEQ ID NO: 59 |

*FIG. 2-2.*

MUTAGENESIS LIBRARY ON2598

GGXXXXYXCRIGPITWVCXXXXXX (G₄S) (SEQ ID NO: 239) 4 - pIIIV

FIG. 3.

ON 3007
(NNK)₁₀ Tyr (NNK) Cys (NNK)₂ Gly Pro (NNK) Thr Trp (NNK) Cys (Gly)₄ Ser (SEQ ID NO: 255) - pIII/pVIII

FIG. 4A.

ON 3016
Gly Gly (NNK)₄ Tyr Cys (NNK)₂ Gly Pro (NNK) Thr Trp (NNK) Cys (NNK)₅ (Gly)₄ Ser (SEQ ID NO: 256) - pIII/pVIII

FIG. 4B.

ON 3017
Gly Gly Tyr (NNK) Cys (NNK)₂ Gly Pro (NNK) Thr Trp (NNK) Cys (NNK)₁₀ - (Gly)₄ Ser (SEQ ID NO: 257) - pIII/pVIII

NNK = RANDOM AMINO ACID RESIDUE.
RESIDUES IN BOLD ARE FIXED.

FIG. 4C.

AF11157
ggTYSCHFGPLTWVCKPQgg (SEQ ID NO: 8)

-X₄YXCHFGPLTWVCX₆ (SEQ ID NO: 258) (C-TERMINUS)

FIG. 5.

ON3236
  -X₄YXCXXGPETWECX6 (SEQ ID NO: 259) (C-TERMINUS)
  Y-C-G-P-T-W-C   FIXED
  E   91:3:3:3/9I:3:3:3/K
  X   NNK

FIG. 6.

1 mg/mouse, n=8
2 mg/mouse, n=8

SEQUENCE LISTING ( 1 ) GENERAL INFORMATION:

( i i i ) NUMBER OF SEQUENCES: 259

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Xaa = Cys, Ala,
            alpha-amino- gamma-bromobutyric acid,
            or homocysteine, provided that either Xaa
            in position 1 or position 10 is Cys or
            homocysteine"

( i x ) FEATURE:
        ( A ) NAME/KEY: Modified-site
        ( B ) LOCATION: 2
        ( D ) OTHER INFORMATION: /note= "Xaa = Arg, His, Leu, or
            Trp"

( i x ) FEATURE:
        ( A ) NAME/KEY: Modified-site
        ( B ) LOCATION: 3
        ( D ) OTHER INFORMATION: /note= "Xaa = Met, Phe, or Ile"

( i x ) FEATURE:
        ( A ) NAME/KEY: Modified-site
        ( B ) LOCATION: 6
        ( D ) OTHER INFORMATION: /note= "Xaa = any amino acid"

( i x ) FEATURE:
        ( A ) NAME/KEY: Modified-site
        ( B ) LOCATION: 9
        ( D ) OTHER INFORMATION: /note= "Xaa = Asp, Glu, Ile, Leu,
            or Val"

( i x ) FEATURE:
        ( A ) NAME/KEY: Modified-site
        ( B ) LOCATION: 10
        ( D ) OTHER INFORMATION: /note= "Xaa = Cys, Ala,
            alpha-amino- gamma-bromobutyric acid,
            or homocysteine, provided that either Xaa
            in position 1 or position 10 is Cys or
            homocysteine"

( x i ) SEQUENCE DESCRIPTION: SEQ ID NO:1:

Xaa  Xaa  Xaa  Gly  Pro  Xaa  Thr  Trp  Xaa  Xaa
    1                        5                                  1 0

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /note= "Xaa = any amino acid"

( i x ) FEATURE:

( A ) NAME/KEY: Modified-site
( B ) LOCATION: 3
( D ) OTHER INFORMATION: /note= "Xaa = Cys, Ala,
   alpha-amino- gamma-bromobutyric acid,
   or homocysteine, provided that either Xaa
   in position 3 or position 12 is Cys or
   homocysteine"

( i x ) FEATURE:
   ( A ) NAME/KEY: Modified-site
   ( B ) LOCATION: 4
   ( D ) OTHER INFORMATION: /note= "Xaa = Arg, His, Leu, or
      Trp"

( i x ) FEATURE:
   ( A ) NAME/KEY: Modified-site
   ( B ) LOCATION: 5
   ( D ) OTHER INFORMATION: /note= "Xaa = Met, Phe, or Ile"

( i x ) FEATURE:
   ( A ) NAME/KEY: Modified-site
   ( B ) LOCATION: 8
   ( D ) OTHER INFORMATION: /note= "Xaa = any amino acid"

( i x ) FEATURE:
   ( A ) NAME/KEY: Modified-site
   ( B ) LOCATION: 11
   ( D ) OTHER INFORMATION: /note= "Xaa = Asp, Glu, Ile, Leu,
      or Val"

( i x ) FEATURE:
   ( A ) NAME/KEY: Modified-site
   ( B ) LOCATION: 12
   ( D ) OTHER INFORMATION: /note= "Xaa = Cys, Ala,
      alpha-amino- gamma-bromobutyric acid,
      or homocysteine, provided that either Xaa
      in position 3 or position 12 is Cys or
      homocysteine"

( x i ) SEQUENCE DESCRIPTION: SEQ ID NO:2:

Tyr Xaa Xaa Xaa Xaa Gly Pro Xaa Thr Trp Xaa Xaa
1               5                       10

( 2 ) INFORMATION FOR SEQ ID NO:3:

( i ) SEQUENCE CHARACTERISTICS:
      ( A ) LENGTH: 16 amino acids
      ( B ) TYPE: amino acid
      ( C ) STRANDEDNESS:
      ( D ) TOPOLOGY: linear ( i i ) MOLECULE TYPE: peptide ( i x ) FEATURE:
      ( A ) NAME/KEY: Modified-site
      ( B ) LOCATION: 1
      ( D ) OTHER INFORMATION: /note= "Xaa = any amino acid"

( i x ) FEATURE:
      ( A ) NAME/KEY: Modified-site
      ( B ) LOCATION: 3
      ( D ) OTHER INFORMATION: /note= "Xaa = any amino acid"

( i x ) FEATURE:
      ( A ) NAME/KEY: Modified-site
      ( B ) LOCATION: 4
      ( D ) OTHER INFORMATION: /note= "Xaa = Cys, Ala,
         alpha-amino- gamma-bromobutyric acid,
         or homocysteine, provided that either Xaa
         in position 4 or position 13 is Cys or
         homocysteine"

( i x ) FEATURE:
      ( A ) NAME/KEY: Modified-site
      ( B ) LOCATION: 5
      ( D ) OTHER INFORMATION: /note= "Xaa = Arg, His, Leu, or
         Trp"

( i x ) FEATURE:
    ( A ) NAME/KEY: Modified-site
    ( B ) LOCATION: 6
    ( D ) OTHER INFORMATION: /note= "Xaa = Met, Phe, or Ile"

( i x ) FEATURE:
    ( A ) NAME/KEY: Modified-site
    ( B ) LOCATION: 9
    ( D ) OTHER INFORMATION: /note= "Xaa = any amino acid"

( i x ) FEATURE:
    ( A ) NAME/KEY: Modified-site
    ( B ) LOCATION: 12
    ( D ) OTHER INFORMATION: /note= "Xaa = Asp, Glu, Ile, Leu, or Val"

( i x ) FEATURE:
    ( A ) NAME/KEY: Modified-site
    ( B ) LOCATION: 13
    ( D ) OTHER INFORMATION: /note= "Xaa = Cys, Ala, alpha-amino- gamma-bromobutyric acid, or homocysteine, provided that either Xaa in position 4 or position 13 is Cys or homocysteine"

( i x ) FEATURE:
    ( A ) NAME/KEY: Modified-site
    ( B ) LOCATION: 14
    ( D ) OTHER INFORMATION: /note= "Xaa = any amino acid"

( i x ) FEATURE:
    ( A ) NAME/KEY: Modified-site
    ( B ) LOCATION: 15
    ( D ) OTHER INFORMATION: /note= "Xaa = any amino acid"

( i x ) FEATURE:
    ( A ) NAME/KEY: Modified-site
    ( B ) LOCATION: 16
    ( D ) OTHER INFORMATION: /note= "Xaa = any amino acid"

( x i ) SEQUENCE DESCRIPTION: SEQ ID NO:3:

Xaa Tyr Xaa Xaa Xaa Xaa Gly Pro Xaa Thr Trp Xaa Xaa Xaa Xaa Xaa
1               5                       10                      15

( 2 ) INFORMATION FOR SEQ ID NO:4:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Xaa = any amino acid"

( i x ) FEATURE:
        ( A ) NAME/KEY: Modified-site
        ( B ) LOCATION: 3
        ( D ) OTHER INFORMATION: /note= "Xaa = any amino acid"

( i x ) FEATURE:
        ( A ) NAME/KEY: Modified-site
        ( B ) LOCATION: 5
        ( D ) OTHER INFORMATION: /note= "Xaa = Arg, His, Leu, or Trp"

( i x ) FEATURE:
        ( A ) NAME/KEY: Modified-site
        ( B ) LOCATION: 6
        ( D ) OTHER INFORMATION: /note= "Xaa = Met, Phe, or Ile"

( i x ) FEATURE:
        ( A ) NAME/KEY: Modified-site
        ( B ) LOCATION: 9

-continued (D) OTHER INFORMATION: /note= "Xaa = any amino acid"

(ix) FEATURE:
  (A) NAME/KEY: Modified-site
  (B) LOCATION: 12
  (D) OTHER INFORMATION: /note= "Xaa = Asp, Glu, Ile, Leu,
    or Val"

(ix) FEATURE:
  (A) NAME/KEY: Modified-site
  (B) LOCATION: 14
  (D) OTHER INFORMATION: /note= "Xaa = any amino acid"

(ix) FEATURE:
  (A) NAME/KEY: Modified-site
  (B) LOCATION: 15
  (D) OTHER INFORMATION: /note= "Xaa = any amino acid"

(ix) FEATURE:
  (A) NAME/KEY: Modified-site
  (B) LOCATION: 16
  (D) OTHER INFORMATION: /note= "Xaa = any amino acid"

(xi) SEQUENCE DESCRIPTION: SEQ ID NO:4:

Xaa Tyr Xaa Cys Xaa Xaa Gly Pro Xaa Thr Trp Xaa Cys Xaa Xaa Xaa
1      5          10         15

(2) INFORMATION FOR SEQ ID NO:5:

(i) SEQUENCE CHARACTERISTICS:
  (A) LENGTH: 16 amino acids
  (B) TYPE: amino acid
  (C) STRANDEDNESS:
  (D) TOPOLOGY: linear (ii) MOLECULE TYPE: peptide (ix) FEATURE:
  (A) NAME/KEY: Modified-site
  (B) LOCATION: 1
  (D) OTHER INFORMATION: /note= "Xaa = any amino acid"

(ix) FEATURE:
  (A) NAME/KEY: Modified-site
  (B) LOCATION: 3
  (D) OTHER INFORMATION: /note= "Xaa = any amino acid"

(ix) FEATURE:
  (A) NAME/KEY: Modified-site
  (B) LOCATION: 5
  (D) OTHER INFORMATION: /note= "Xaa = Arg or His"

(ix) FEATURE:
  (A) NAME/KEY: Modified-site
  (B) LOCATION: 6
  (D) OTHER INFORMATION: /note= "Xaa = Phe or Met"

(ix) FEATURE:
  (A) NAME/KEY: Modified-site
  (B) LOCATION: 9
  (D) OTHER INFORMATION: /note= "Xaa = Ile, Leu, Thr, Met,
    or Val"

(ix) FEATURE:
  (A) NAME/KEY: Modified-site
  (B) LOCATION: 12
  (D) OTHER INFORMATION: /note= "Xaa = Asp or Val"

(ix) FEATURE:
  (A) NAME/KEY: Modified-site
  (B) LOCATION: 14
  (D) OTHER INFORMATION: /note= "Xaa = Gly, Lys, Leu, Gln,
    Arg, Ser, or Thr"

(ix) FEATURE:
  (A) NAME/KEY: Modified-site
  (B) LOCATION: 15
  (D) OTHER INFORMATION: /note= "Xaa = Ala, Gly, Pro, Arg, or Tyr"

(ix) FEATURE:
    (A) NAME/KEY: Modified-site
    (B) LOCATION: 16
    (D) OTHER INFORMATION: /note= "Xaa = any amino acid"

(xi) SEQUENCE DESCRIPTION: SEQ ID NO:5:

Xaa Tyr Xaa Cys Xaa Xaa Gly Pro Xaa Thr Trp Xaa Cys Xaa Xaa Xaa
 1               5                   10                  15

(2) INFORMATION FOR SEQ ID NO:6:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = Asp, Glu, Leu, Asn,
             Ser, Thr, or Val"

(ix) FEATURE:
        (A) NAME/KEY: Modified-site
        (B) LOCATION: 3
        (D) OTHER INFORMATION: /note= "Xaa = Ala, His, Lys, Leu,
             Met, Ser, or Thr"

(ix) FEATURE:
        (A) NAME/KEY: Modified-site
        (B) LOCATION: 5
        (D) OTHER INFORMATION: /note= "Xaa = Arg or His"

(ix) FEATURE:
        (A) NAME/KEY: Modified-site
        (B) LOCATION: 6
        (D) OTHER INFORMATION: /note= "Xaa = Phe or Met"

(ix) FEATURE:
        (A) NAME/KEY: Modified-site
        (B) LOCATION: 9
        (D) OTHER INFORMATION: /note= "Xaa = Ile, Leu, Thr, Met,
             or Val"

(ix) FEATURE:
        (A) NAME/KEY: Modified-site
        (B) LOCATION: 12
        (D) OTHER INFORMATION: /note= "Xaa = Asp or Val"

(ix) FEATURE:
        (A) NAME/KEY: Modified-site
        (B) LOCATION: 14
        (D) OTHER INFORMATION: /note= "Xaa = Lys, Arg, Ser, or
             Thr"

(ix) FEATURE:
        (A) NAME/KEY: Modified-site
        (B) LOCATION: 16
        (D) OTHER INFORMATION: /note= "Xaa = any amino acid"

(xi) SEQUENCE DESCRIPTION: SEQ ID NO:6:

Xaa Tyr Xaa Cys Xaa Xaa Gly Pro Xaa Thr Trp Xaa Cys Xaa Pro Xaa
 1               5                   10                  15

(2) INFORMATION FOR SEQ ID NO:7:

(i) SEQUENCE CHARACTERISTICS:
        (A) LENGTH: 20 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:7:

```
Gly Gly Leu Tyr Leu Cys Arg Phe Gly Pro Val Thr Trp Asp Cys Gly
1               5                   10                  15
Tyr Lys Gly Gly
            20
```

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:8:

```
Gly Gly Thr Tyr Ser Cys His Phe Gly Pro Leu Thr Trp Val Cys Lys
1               5                   10                  15
Pro Gln Gly Gly
            20
```

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:9:

```
Gly Gly Asp Tyr His Cys Arg Met Gly Pro Leu Thr Trp Val Cys Lys
1               5                   10                  15
Pro Leu Gly Gly
            20
```

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:10:

```
Val Gly Asn Tyr Met Cys His Phe Gly Pro Ile Thr Trp Val Cys Arg
1               5                   10                  15
Pro Gly Gly Gly
            20
```

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:11:

```
Gly Gly Val Tyr Ala Cys Arg Met Gly Pro Ile Thr Trp Val Cys Ser
1               5                   10                  15

Pro Leu Gly Gly
            20
```

( 2 ) INFORMATION FOR SEQ ID NO:12:

( i ) SEQUENCE CHARACTERISTICS:
        ( A ) LENGTH: 19 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:12:

```
Val Gly Asn Tyr Met Ala His Met Gly Pro Ile Thr Trp Val Cys Arg
1               5                   10                  15

Pro Gly Gly
```

( 2 ) INFORMATION FOR SEQ ID NO:13:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:13:

```
Gly Gly Thr Tyr Ser Cys His Phe Gly Pro Leu Thr Trp Val Cys Lys
1               5                   10                  15

Pro Gln
```

( 2 ) INFORMATION FOR SEQ ID NO:14:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:14:

```
Gly Gly Leu Tyr Ala Cys His Met Gly Pro Met Thr Trp Val Cys Gln
1               5                   10                  15

Pro Leu Arg Gly
            20
```

( 2 ) INFORMATION FOR SEQ ID NO:15:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:15:

```
Thr Ile Ala Gln Tyr Ile Cys Tyr Met Gly Pro Glu Thr Trp Glu Cys
1               5                   10                  15

Arg Pro Ser Pro Lys Ala
            20
```

( 2 ) INFORMATION FOR SEQ ID NO:16:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:16:

```
Tyr  Ser  Cys  His  Phe  Gly  Pro  Leu  Thr  Trp  Val  Cys  Lys
1                   5                        10
```

( 2 ) INFORMATION FOR SEQ ID NO:17:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:17:

```
Tyr  Cys  His  Phe  Gly  Pro  Leu  Thr  Trp  Val  Cys
1              5                        10
```

( 2 ) INFORMATION FOR SEQ ID NO:18:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
            / note= "Xaa = N-acetyl-glycine"

( x i ) SEQUENCE DESCRIPTION: SEQ ID NO:18:

```
Xaa  Gly  Thr  Tyr  Ser  Cys  His  Phe  Gly  Pro  Leu  Thr  Trp  Val  Cys  Lys
1                   5                        10                            15

Pro  Gln  Gly  Gly
               20
```

( 2 ) INFORMATION FOR SEQ ID NO:19:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:19:

```
Gly  Gly  Cys  Arg  Ile  Gly  Pro  Ile  Thr  Trp  Val  Cys  Gly  Gly
1                   5                        10
```

( 2 ) INFORMATION FOR SEQ ID NO:20:

( i ) SEQUENCE CHARACTERISTICS:
        ( A ) LENGTH: 23 amino acids
        ( B ) TYPE: amino acid ( C ) STRANDEDNESS:
( D ) TOPOLOGY: linear ( i i ) MOLECULE TYPE: peptide ( x i ) SEQUENCE DESCRIPTION: SEQ ID NO:20:

Gly Gly Thr Tyr Ser Cys His Phe Gly Pro Leu Thr Trp Val Cys Lys
1               5                   10                  15

Pro Gln Gly Gly Ser Ser Lys
            20

( 2 ) INFORMATION FOR SEQ ID NO:21:

( i ) SEQUENCE CHARACTERISTICS:
( A ) LENGTH: 22 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:21:

Leu Gly Arg Lys Tyr Ser Cys His Phe Gly Pro Leu Thr Trp Val Cys
1               5                   10                  15

Gln Pro Ala Lys Lys Asp
            20

( 2 ) INFORMATION FOR SEQ ID NO:22:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:22:

Gly Gly Trp Val Thr Cys Arg Met Gly Pro Ile Thr Trp Val Cys Gly
1               5                   10                  15

Val His Gly Gly
            20

( 2 ) INFORMATION FOR SEQ ID NO:23:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:23:

Gly Gly Gln Leu Leu Cys Gly Ile Gly Pro Ile Thr Trp Val Cys Arg
1               5                   10                  15

Trp Val Gly Gly
            20

( 2 ) INFORMATION FOR SEQ ID NO:24:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:24:

Gly Gly Leu Tyr Leu Cys Arg Met Gly Pro Val Thr Trp Glu Cys Gln
1               5                   10                  15

Pro Arg Gly Gly
            20

( 2 ) INFORMATION FOR SEQ ID NO:25:

( i ) SEQUENCE CHARACTERISTICS:
( A ) LENGTH: 22 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:25:

Gly Gly Lys Tyr Ser Cys Phe Met Gly Pro Thr Thr Trp Val Cys Ser
1               5                   10                  15

Pro Val Gly Arg Gly Val
            20

( 2 ) INFORMATION FOR SEQ ID NO:26:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:26:

Gly Gly Trp Val Tyr Cys Arg Ile Gly Pro Ile Thr Trp Val Cys Asp
1               5                   10                  15

Thr Asn Gly Gly
            20

( 2 ) INFORMATION FOR SEQ ID NO:27:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:27:

Gly Gly Ile Tyr Lys Cys Leu Met Gly Pro Leu Thr Trp Val Cys Thr
1               5                   10                  15

Pro Asp Gly Gly
            20

( 2 ) INFORMATION FOR SEQ ID NO:28:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:28:

Gly Gly Met Tyr Tyr Cys Arg Met Gly Pro Met Thr Trp Val Cys Lys

```
                1               5                      10                      15

Gly  Ala  Gly  Gly
                        20
```

( 2 ) INFORMATION FOR SEQ ID NO:29:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:29:

```
        Gly  Gly  Thr  Thr  Gln  Cys  Trp  Ile  Gly  Pro  Ile  Thr  Trp  Val  Cys  Arg
        1                   5                        10                      15

Ala  Arg  Gly  Gly
                        20
```

( 2 ) INFORMATION FOR SEQ ID NO:30:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:30:

```
        Gly  Gly  Pro  Tyr  His  Cys  Arg  Met  Gly  Pro  Ile  Thr  Trp  Val  Cys  Gly
        1                   5                        10                      15

Pro  Val  Gly  Gly
                        20
```

( 2 ) INFORMATION FOR SEQ ID NO:31:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:31:

```
        Gly  Gly  Glu  Tyr  Leu  Cys  Arg  Met  Gly  Pro  Ile  Thr  Trp  Val  Cys  Glu
        1                   5                        10                      15

Arg  Tyr  Gly  Gly
                        20
```

( 2 ) INFORMATION FOR SEQ ID NO:32:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:32:

```
        Gly  Gly  Glu  Tyr  Arg  Cys  Arg  Met  Gly  Pro  Ile  Ser  Trp  Val  Cys  Ser
        1                   5                        10                      15

Pro  Gln  Gly  Gly
                        20
```

( 2 ) INFORMATION FOR SEQ ID NO:33:

( i ) SEQUENCE CHARACTERISTICS:
    ( A ) LENGTH: 22 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:33:

```
Gly  Gly  Asn  Tyr  Thr  Cys  Arg  Phe  Gly  Pro  Leu  Thr  Trp  Glu  Cys  Thr
1                   5                        10                       15
Pro  Gln  Gly  Gly  Gly  Ala
               20
```

( 2 ) INFORMATION FOR SEQ ID NO:34:

( i ) SEQUENCE CHARACTERISTICS:
    ( A ) LENGTH: 20 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:34:

```
Gly  Gly  Asn  Tyr  Val  Cys  Arg  Met  Gly  Pro  Ile  Thr  Trp  Ile  Cys  Thr
1                   5                        10                       15
Pro  Ala  Gly  Gly
               20
```

( 2 ) INFORMATION FOR SEQ ID NO:35:

( i ) SEQUENCE CHARACTERISTICS:
    ( A ) LENGTH: 20 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:35:

```
Gly  Gly  Ser  Trp  Asp  Cys  Arg  Ile  Gly  Pro  Ile  Thr  Trp  Val  Cys  Lys
1                   5                        10                       15
Trp  Ser  Gly  Gly
               20
```

( 2 ) INFORMATION FOR SEQ ID NO:36:

( i ) SEQUENCE CHARACTERISTICS:
    ( A ) LENGTH: 20 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:36:

```
Gly  Gly  Asp  Tyr  Thr  Cys  Arg  Met  Gly  Pro  Met  Thr  Trp  Ile  Cys  Thr
1                   5                        10                       15
Ala  Thr  Arg  Gly
               20
```

( 2 ) INFORMATION FOR SEQ ID NO:37:

( i ) SEQUENCE CHARACTERISTICS:
    ( A ) LENGTH: 20 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:37:

```
Gly Gly Asp Tyr Asn Cys Arg Phe Gly Pro Leu Thr Trp Val Cys Lys
1               5                   10                  15
Pro Ser Gly Gly
            20
```

( 2 ) INFORMATION FOR SEQ ID NO:38:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:38:

```
Gly Gly Ser Tyr Leu Cys Arg Met Gly Pro Thr Thr Trp Leu Cys Thr
1               5                   10                  15
Ala Gln Arg Gly
            20
```

( 2 ) INFORMATION FOR SEQ ID NO:39:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:39:

```
Gly Gly Leu Tyr Leu Cys Arg Met Gly Pro Gln Thr Trp Met Cys Gln
1               5                   10                  15
Pro Gly Gly Gly
            20
```

( 2 ) INFORMATION FOR SEQ ID NO:40:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:40:

```
Gly Gly Asp Tyr Val Cys Arg Met Gly Pro Met Thr Trp Val Cys Ala
1               5                   10                  15
Pro Tyr Gly Arg
            20
```

( 2 ) INFORMATION FOR SEQ ID NO:41:

( i ) SEQUENCE CHARACTERISTICS:
        ( A ) LENGTH: 20 amino acids
        ( B ) TYPE: amino acid
        ( C ) STRANDEDNESS:

(D) TOPOLOGY: linear (i i) MOLECULE TYPE: peptide (x i) SEQUENCE DESCRIPTION: SEQ ID NO:41:

Gly Gly Leu Tyr Glu Cys Arg Met Gly Pro Met Thr Trp Val Cys Arg
1               5                   10                  15
Pro Gly Gly Gly
            20

(2) INFORMATION FOR SEQ ID NO:42:

(i) SEQUENCE CHARACTERISTICS:
    (A) LENGTH: 20 amino acids
    (B) TYPE: amino acid
    (C) STRANDEDNESS:
    (D) TOPOLOGY: linear (i i) MOLECULE TYPE: peptide (x i) SEQUENCE DESCRIPTION: SEQ ID NO:42:

Gly Gly Trp Tyr Ser Cys Leu Met Gly Pro Met Thr Trp Val Cys Lys
1               5                   10                  15
Ala His Arg Gly
            20

(2) INFORMATION FOR SEQ ID NO:43:

(i) SEQUENCE CHARACTERISTICS:
    (A) LENGTH: 20 amino acids
    (B) TYPE: amino acid
    (C) STRANDEDNESS:
    (D) TOPOLOGY: linear (i i) MOLECULE TYPE: peptide (x i) SEQUENCE DESCRIPTION: SEQ ID NO:43:

Gly Gly Lys Tyr Tyr Cys Trp Met Gly Pro Met Thr Trp Val Cys Ser
1               5                   10                  15
Pro Ala Gly Gly
            20

(2) INFORMATION FOR SEQ ID NO:44:

(i) SEQUENCE CHARACTERISTICS:
    (A) LENGTH: 20 amino acids
    (B) TYPE: amino acid
    (C) STRANDEDNESS:
    (D) TOPOLOGY: linear (i i) MOLECULE TYPE: peptide (x i) SEQUENCE DESCRIPTION: SEQ ID NO:44:

Gly Gly Tyr Val Met Cys Arg Ile Gly Pro Ile Thr Trp Val Cys Asp
1               5                   10                  15
Ile Pro Gly Gly
            20

(2) INFORMATION FOR SEQ ID NO:45:

(i) SEQUENCE CHARACTERISTICS:
    (A) LENGTH: 20 amino acids
    (B) TYPE: amino acid
    (C) STRANDEDNESS:
    (D) TOPOLOGY: linear (i i) MOLECULE TYPE: peptide ( x i ) SEQUENCE DESCRIPTION: SEQ ID NO:45:

Gly Ser Cys Leu Gln Cys Cys Ile Gly Pro Ile Thr Trp Val Cys Arg
1               5                   10                  15

His Ala Gly Gly
            20

( 2 ) INFORMATION FOR SEQ ID NO:46:

( i ) SEQUENCE CHARACTERISTICS:
    ( A ) LENGTH: 20 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:46:

Gly Gly Asn Tyr Phe Cys Arg Met Gly Pro Ile Thr Trp Val Cys Gln
1               5                   10                  15

Arg Ser Val Gly
            20

( 2 ) INFORMATION FOR SEQ ID NO:47:

( i ) SEQUENCE CHARACTERISTICS:
    ( A ) LENGTH: 20 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:47:

Gly Gly Glu Tyr Ile Cys Arg Met Gly Pro Leu Thr Trp Glu Cys Lys
1               5                   10                  15

Arg Thr Gly Gly
            20

( 2 ) INFORMATION FOR SEQ ID NO:48:

( i ) SEQUENCE CHARACTERISTICS:
    ( A ) LENGTH: 20 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:48:

Gly Gly Leu Tyr Ala Cys Arg Met Gly Pro Ile Thr Trp Val Cys Lys
1               5                   10                  15

Tyr Met Ala Gly
            20

( 2 ) INFORMATION FOR SEQ ID NO:49:

( i ) SEQUENCE CHARACTERISTICS:
    ( A ) LENGTH: 22 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:49:

Gly Gly Gln Tyr Leu Cys Thr Phe Gly Pro Ile Thr Trp Leu Cys Arg
1               5                   10                  15

```
                Gly  Ala  Gly  Gly  Gly  Ser
                              20
```

( 2 ) INFORMATION FOR SEQ ID NO:50:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:50:

```
Gly  Gly  Tyr  Thr  Thr  Cys  Arg  Met  Gly  Pro  Ile  Thr  Trp  Val  Cys  Ser
 1                  5                           10                         15
Ala  His  Gly  Gly
              20
```

( 2 ) INFORMATION FOR SEQ ID NO:51:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:51:

```
Gly  Gly  Thr  Tyr  Lys  Cys  Trp  Met  Gly  Pro  Met  Thr  Trp  Val  Cys  Arg
 1                  5                           10                         15
Pro  Val  Gly  Gly
              20
```

( 2 ) INFORMATION FOR SEQ ID NO:52:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:52:

```
Gly  Gly  Thr  Ala  Ser  Cys  His  Phe  Gly  Pro  Leu  Thr  Trp  Val  Cys  Lys
 1                  5                           10                         15
Pro  Gln  Gly  Gly
              20
```

( 2 ) INFORMATION FOR SEQ ID NO:53:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:53:

```
Gly  Gly  Asn  Tyr  Tyr  Cys  Arg  Phe  Gly  Pro  Ile  Thr  Phe  Glu  Cys  His
 1                  5                           10                         15
Pro  Thr  Gly  Gly
              20
```

( 2 ) INFORMATION FOR SEQ ID NO:54:

( i ) SEQUENCE CHARACTERISTICS:
        ( A ) LENGTH: 23 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:54:

```
Gly Gly Leu Tyr Ala Cys His Met Gly Pro Met Thr Trp Val Cys Gln
1               5                   10                  15
Pro Leu Arg Gly Gly Gly Ser
            20
```

( 2 ) INFORMATION FOR SEQ ID NO:55:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:55:

```
Gly Gly Glu Tyr Lys Cys Tyr Met Gly Pro Ile Thr Trp Val Cys Lys
1               5                   10                  15
Pro Glu Gly Gly
            20
```

( 2 ) INFORMATION FOR SEQ ID NO:56:

( i ) SEQUENCE CHARACTERISTICS:
        ( A ) LENGTH: 23 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:56:

```
Gly Gly Asp Tyr Val Cys Arg Met Gly Pro Met Thr Trp Val Cys Ala
1               5                   10                  15
Pro Tyr Gly Arg Gly Gly Ser
            20
```

( 2 ) INFORMATION FOR SEQ ID NO:57:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:57:

```
Gly Gly Glu Tyr Leu Cys Arg Met Gly Pro Met Thr Trp Val Cys Thr
1               5                   10                  15
Pro Val Gly Gly
            20
```

( 2 ) INFORMATION FOR SEQ ID NO:58:

( i ) SEQUENCE CHARACTERISTICS:

(A) LENGTH: 23 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:58:

Gly Gly Ser Tyr Leu Cys Arg Met Gly Pro Thr Thr Trp Leu Cys Thr
1               5                   10                  15
Ala Gln Arg Gly Gly Gly Asn
            20

(2) INFORMATION FOR SEQ ID NO:59:

(i) SEQUENCE CHARACTERISTICS:
(A) LENGTH: 20 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:59:

Gly Gly Leu Tyr Thr Cys Arg Met Gly Pro Ile Thr Trp Val Cys Leu
1               5                   10                  15
Pro Ala Gly Gly
            20

(2) INFORMATION FOR SEQ ID NO:60:

(i) SEQUENCE CHARACTERISTICS:
(A) LENGTH: 20 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:60:

Gly Gly Leu Tyr Lys Cys Arg Met Gly Pro Met Thr Trp Val Cys Ser
1               5                   10                  15
Pro Phe Gly Gly
            20

(2) INFORMATION FOR SEQ ID NO:61:

(i) SEQUENCE CHARACTERISTICS:
(A) LENGTH: 18 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:61:

Gly Gly Pro His His Val Tyr Ala Cys Arg Met Gly Pro Leu Thr Trp
1               5                   10                  15
Ile Cys (2) INFORMATION FOR SEQ ID NO:62:

(i) SEQUENCE CHARACTERISTICS:
(A) LENGTH: 12 amino acids
(B) TYPE: amino acid
(C) STRANDEDNESS:
(D) TOPOLOGY: linear ( i i ) MOLECULE TYPE: peptide ( x i ) SEQUENCE DESCRIPTION: SEQ ID NO:62:

Tyr Xaa Cys Arg Ile Gly Pro Ile Thr Trp Val Cys
1               5                   10

( 2 ) INFORMATION FOR SEQ ID NO:63:

( i ) SEQUENCE CHARACTERISTICS:
      ( A ) LENGTH: 23 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:63:

Gly Gly Glu Tyr Ile Cys Val Met Gly Pro Asn Thr Trp Val Cys Ser
1               5                   10                  15

Pro Thr Arg Gly His Gly Ser
                20

( 2 ) INFORMATION FOR SEQ ID NO:64:

( i ) SEQUENCE CHARACTERISTICS:
      ( A ) LENGTH: 22 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:64:

Gly Gly Glu Tyr Leu Cys Arg Met Gly Pro Met Thr Trp Val Ser Pro
1               5                   10                  15

Phe Thr Arg Lys Gly Gly
                20

( 2 ) INFORMATION FOR SEQ ID NO:65:

( i ) SEQUENCE CHARACTERISTICS:
      ( A ) LENGTH: 22 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:65:

Gly Gly Gln Tyr Ile Cys Arg Phe Gly Pro Ile Thr Trp Gln Ser Gln
1               5                   10                  15

Pro Ala Gly Gly Gly Ser
                20

( 2 ) INFORMATION FOR SEQ ID NO:66:

( i ) SEQUENCE CHARACTERISTICS:
      ( A ) LENGTH: 23 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:66:

Gly Arg Glu Tyr Ser Cys Arg Met Gly Pro Ile Thr Trp Val Cys Met
1               5                   10                  15

```
          Pro  Arg  Ala  Ser  Leu  Gly  Ser
                         20
```

(2) INFORMATION FOR SEQ ID NO:67:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:67:

```
Gly  Asp  Tyr  Leu  Cys  Ser  Met  Gly  Pro  Ile  Thr  Trp  Ile  Cys  Val  Pro
1                   5                        10                       15
Glu  Arg  Gly  Gly  Gly  Ser
                    20
```

(2) INFORMATION FOR SEQ ID NO:68:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:68:

```
Glu  Leu  Trp  Tyr  Ser  Cys  Arg  Met  Gly  Pro  Val  Thr  Trp  Met  Cys  Gly
1                   5                        10                       15
Arg  Tyr  Gln  Gly  Gly  Gly  Ser
                    20
```

(2) INFORMATION FOR SEQ ID NO:69:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:69:

```
Gln  Ile  Cys  Arg  Ala  Asp  Arg  Lys  Gly  Ile  Tyr  Gln  Cys  Trp  Tyr  Gly
1                   5                        10                       15
Pro  Glu  Thr  Trp  Ile  Cys  Gly  Gly
                    20
```

(2) INFORMATION FOR SEQ ID NO:70:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:70:

```
Gln  Gln  Gly  Tyr  Ser  Leu  Trp  Leu  Pro  Trp  Tyr  Asn  Cys  Val  Leu  Gly
1                   5                        10                       15
Pro  Tyr  Thr  Trp  Val  Cys  Gly  Gly
                    20
```

(2) INFORMATION FOR SEQ ID NO:71:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:71:

```
Tyr  Gly  Gly  Ser  Ala  Ala  Val  Pro  Trp  Lys  Tyr  Gly  Cys  Ser  Leu  Gly
1                   5                        10                       15

Pro  Val  Thr  Trp  Val  Cys  Gly  Gly
               20
```

(2) INFORMATION FOR SEQ ID NO:72:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:72:

```
Gln  Ile  Val  Ser  Trp  Gly  Leu  Tyr  Ser  Gly  Tyr  Leu  Cys  Met  Val  Gly
1                   5                        10                       15

Pro  Val  Thr  Trp  Leu  Cys  Gly  Gly
               20
```

(2) INFORMATION FOR SEQ ID NO:73:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:73:

```
Gly  Ser  Gly  Ala  Leu  Ser  Ala  Ala  Gly  Trp  Tyr  Gly  Cys  Arg  Val  Gly
1                   5                        10                       15

Pro  Leu  Thr  Trp  Val  Cys  Gly  Gly
               20
```

(2) INFORMATION FOR SEQ ID NO:74:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:74:

```
Ser  Val  Val  Ser  His  Asp  Ala  Ala  Gly  Val  Tyr  Asp  Cys  Val  Ile  Gly
1                   5                        10                       15

Pro  Val  Thr  Trp  Ile  Cys  Gly  Gly
               20
```

(2) INFORMATION FOR SEQ ID NO:75:

(i) SEQUENCE CHARACTERISTICS:
        (A) LENGTH: 24 amino acids ( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:75:

Ile Tyr Ser Trp Thr Gly Ile Leu Gly Ser Tyr Val Cys Trp Tyr Gly
1               5                   10                  15

Pro Asp Thr Trp Val Cys Gly Gly
            20

( 2 ) INFORMATION FOR SEQ ID NO:76:

( i ) SEQUENCE CHARACTERISTICS:
( A ) LENGTH: 24 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:76:

Ser Cys Ile Tyr Val Arg Phe Phe Tyr Cys Tyr Gln Cys Ser Glu Gly
1               5                   10                  15

Pro Ala Thr Trp Leu Cys Gly Gly
            20

( 2 ) INFORMATION FOR SEQ ID NO:77:

( i ) SEQUENCE CHARACTERISTICS:
( A ) LENGTH: 24 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:77:

Thr Val Ala Lys Gly Gln Ser Gly Val Arg Tyr Ser Cys Leu Arg Gly
1               5                   10                  15

Pro Glu Thr Trp Val Cys Gly Gly
            20

( 2 ) INFORMATION FOR SEQ ID NO:78:

( i ) SEQUENCE CHARACTERISTICS:
( A ) LENGTH: 24 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:78:

Val Gln Pro Gln Tyr Lys Trp Ala Thr Met Tyr Gln Cys Trp Lys Gly
1               5                   10                  15

Pro Ser Thr Trp Phe Cys Gly Gly
            20

( 2 ) INFORMATION FOR SEQ ID NO:79:

( i ) SEQUENCE CHARACTERISTICS:
( A ) LENGTH: 24 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:79:

Lys Ser Gly Val Trp Glu Met Gly Ser Ser Tyr Gln Cys Ala Arg Gly
1               5                   10                  15

Pro Arg Thr Trp Cys Cys Gly Gly
            20

( 2 ) INFORMATION FOR SEQ ID NO:80:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:80:

Cys Ser Val Arg Arg Met Asp Arg Glu Tyr Tyr Arg Cys Cys Arg Gly
1               5                   10                  15

Pro Phe Thr Trp Gln Cys Gly Gly
            20

( 2 ) INFORMATION FOR SEQ ID NO:81:

( i ) SEQUENCE CHARACTERISTICS:
        ( A ) LENGTH: 23 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:81:

Lys Tyr Gln Glu Glu Met Phe Met Gly Tyr Gln Cys Leu Gln Gly Pro
1               5                   10                  15

Lys Thr Gln Leu Cys Gly Gly
            20

( 2 ) INFORMATION FOR SEQ ID NO:82:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:82:

Val Cys Pro Gly Ser Glu Phe Arg Val Gly Tyr Ile Cys Ala Met Gly
1               5                   10                  15

Pro Tyr Thr Trp Asp Cys Gly Gly
            20

( 2 ) INFORMATION FOR SEQ ID NO:83:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:83:

```
Ser  Leu  Cys  Ser  Ser  Arg  Cys  Asn  Ser  Pro  Tyr  Phe  Cys  Ser  Ile  Gly
1                  5                       10                      15

Pro  Ser  Thr  Trp  Arg  Cys  Gly  Gly
               20
```

( 2 ) INFORMATION FOR SEQ ID NO:84:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:84:

```
Gln  Ala  Ser  Leu  Gly  Leu  Pro  Leu  Lys  Gln  Tyr  Leu  Cys  Val  Leu  Gly
1                  5                       10                      15

Pro  His  Thr  Trp  Leu  Cys  Gly  Gly
               20
```

( 2 ) INFORMATION FOR SEQ ID NO:85:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:85:

```
Ala  Cys  Lys  Pro  Ala  Ala  Leu  Phe  Val  Gln  Tyr  Gly  Cys  Val  Leu  Gly
1                  5                       10                      15

Pro  Met  Thr  Trp  Ile  Cys  Gly  Gly
               20
```

( 2 ) INFORMATION FOR SEQ ID NO:86:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:86:

```
Ser  Cys  Glu  Arg  Ala  Gly  Gly  Arg  Trp  Glu  Tyr  Val  Cys  Gln  Trp  Gly
1                  5                       10                      15

Pro  Asp  Thr  Trp  Leu  Cys  Gly  Gly
               20
```

( 2 ) INFORMATION FOR SEQ ID NO:87:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:87:

```
Arg  Val  Ala  Arg  Gln  Val  Gln  Gln  Val  Ser  Tyr  Trp  Cys  Ala  His  Gly
1                  5                       10                      15

Pro  Ala  Thr  Cys  Tyr  Cys  Gly  Gly
```

20

( 2 ) INFORMATION FOR SEQ ID NO:88:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:88:

```
His  Lys  Tyr  Asp  Thr  Leu  Met  Leu  Thr  Asn  Tyr  Val  Cys  Gln  Arg  Gly
1                   5                        10                       15
Pro  Leu  Thr  Gln  Leu  Cys  Gly  Gly
                20
```

( 2 ) INFORMATION FOR SEQ ID NO:89:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:89:

```
Gly  Gly  Tyr  His  Cys  Glu  Trp  Gly  Pro  Glu  Thr  Trp  Ile  Cys  Arg  Pro
1                   5                        10                       15
Glu  Ile  Ser  Pro  Leu  Thr  Val  Met  Gly  Gly
                20                       25
```

( 2 ) INFORMATION FOR SEQ ID NO:90:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:90:

```
Gly  Gly  Tyr  Ile  Cys  Asp  Tyr  Gly  Pro  Leu  Thr  Trp  Ala  Cys  Lys  Pro
1                   5                        10                       15
Ala  Gly  Ala  Thr  Leu  Leu  Gln  Pro  Gly  Gly
                20                       25
```

( 2 ) INFORMATION FOR SEQ ID NO:91:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:91:

```
Gly  Gly  Tyr  Thr  Cys  Arg  Phe  Gly  Pro  Val  Thr  Trp  Asp  Cys  Leu  Pro
1                   5                        10                       15
Ala  Ile  Asn  His  Asn  Gly  Val  Leu  Gly  Gly
                20                       25
```

( 2 ) INFORMATION FOR SEQ ID NO:92:

(i) SEQUENCE CHARACTERISTICS:
  (A) LENGTH: 26 amino acids
  (B) TYPE: amino acid
  (C) STRANDEDNESS:
  (D) TOPOLOGY: linear (ii) MOLECULE TYPE: peptide (xi) SEQUENCE DESCRIPTION: SEQ ID NO:92:

```
Gly Gly Tyr Val Cys Asp Phe Gly Pro Thr Thr Trp Ile Cys Arg Gly
1               5                   10                  15
Gln Val Met Glu His Ile Asn Thr Gly Gly
            20                  25
```

(2) INFORMATION FOR SEQ ID NO:93:

(i) SEQUENCE CHARACTERISTICS:
  (A) LENGTH: 26 amino acids
  (B) TYPE: amino acid
  (C) STRANDEDNESS:
  (D) TOPOLOGY: linear (ii) MOLECULE TYPE: peptide (xi) SEQUENCE DESCRIPTION: SEQ ID NO:93:

```
Gly Gly Tyr Met Cys Asn Met Gly Pro Leu Thr Trp Asp Cys Ser Pro
1               5                   10                  15
Val Arg Ser Thr Ser Met Ala Trp Gly Gly
            20                  25
```

(2) INFORMATION FOR SEQ ID NO:94:

(i) SEQUENCE CHARACTERISTICS:
  (A) LENGTH: 26 amino acids
  (B) TYPE: amino acid
  (C) STRANDEDNESS:
  (D) TOPOLOGY: linear (ii) MOLECULE TYPE: peptide (xi) SEQUENCE DESCRIPTION: SEQ ID NO:94:

```
Gly Gly Tyr Asn Cys Thr Met Gly Pro Asn Thr Trp Val Cys Thr Pro
1               5                   10                  15
Ala Ala Glu Ser Pro Ala Val Phe Gly Gly
            20                  25
```

(2) INFORMATION FOR SEQ ID NO:95:

(i) SEQUENCE CHARACTERISTICS:
  (A) LENGTH: 23 amino acids
  (B) TYPE: amino acid
  (C) STRANDEDNESS:
  (D) TOPOLOGY: linear (ii) MOLECULE TYPE: peptide (xi) SEQUENCE DESCRIPTION: SEQ ID NO:95:

```
Gly Gly Tyr Gly Cys Arg Ile Gly Pro Ile Thr Trp Ile Cys Asp Asp
1               5                   10                  15
Val Ser Arg Ser Pro Arg Ala
            20
```

(2) INFORMATION FOR SEQ ID NO:96:

(i) SEQUENCE CHARACTERISTICS:
  (A) LENGTH: 21 amino acids
  (B) TYPE: amino acid ( C ) STRANDEDNESS:
( D ) TOPOLOGY: linear ( i i ) MOLECULE TYPE: peptide ( x i ) SEQUENCE DESCRIPTION: SEQ ID NO:96:

Gly Gly Tyr Thr Cys Arg Met Gly Pro Gln Thr Trp Glu Cys Leu Pro
1               5                   10                  15

Met Ser Glu Gly Val
            20

( 2 ) INFORMATION FOR SEQ ID NO:97:

( i ) SEQUENCE CHARACTERISTICS:
( A ) LENGTH: 22 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:97:

Gly Gly Tyr Asn Cys Lys Phe Gly Pro Gln Thr Trp Asp Cys Ser Ser
1               5                   10                  15

Ala Asn Leu Lys Glu Val
            20

( 2 ) INFORMATION FOR SEQ ID NO:98:

( i ) SEQUENCE CHARACTERISTICS:
( A ) LENGTH: 22 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:98:

Gly Tyr Leu Cys Glu Met Gly Pro Glu Thr Trp Met Cys Arg Pro Glu
1               5                   10                  15

Asp Ala Lys Leu Gly Val
            20

( 2 ) INFORMATION FOR SEQ ID NO:99:

( i ) SEQUENCE CHARACTERISTICS:
( A ) LENGTH: 23 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:99:

Gly Gly Tyr Gly Cys Lys Phe Gly Pro Val Thr Trp Ile Cys Glu Asp
1               5                   10                  15

Leu Leu Leu Asp Pro Met Tyr
            20

( 2 ) INFORMATION FOR SEQ ID NO:100:

( i ) SEQUENCE CHARACTERISTICS:
( A ) LENGTH: 24 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:100:

Gly Gly Tyr Asn Cys Lys Phe Gly Pro Gln Thr Trp Asp Cys Ser Ser
1               5                   10                  15

Ala Asn Leu Lys Glu Val Leu Val
            20

( 2 ) INFORMATION FOR SEQ ID NO:101:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:101:

Gly Tyr Leu Cys Glu Met Gly Pro Glu Thr Trp Met Cys Arg Pro Glu
1               5                   10                  15

Asp Cys Glu Ala Trp
            20

( 2 ) INFORMATION FOR SEQ ID NO:102:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:102:

Gly Gly Tyr Gly Cys Gly Leu Ala Pro Val Thr Trp Glu Cys Pro Gln
1               5                   10                  15

Val Ser Ile Pro Tyr Gly Leu Ser Gly Gly
            20                  25

( 2 ) INFORMATION FOR SEQ ID NO:103:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:103:

Gly Gly Tyr Gly Cys Arg Ile Gly Pro Thr Thr Trp Ile Cys Asp Ser
1               5                   10                  15

Thr Val Pro Gln Leu Arg Glu Val Gly Gly
            20                  25

( 2 ) INFORMATION FOR SEQ ID NO:104:

( i ) SEQUENCE CHARACTERISTICS:
        ( A ) LENGTH: 19 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:104:

Gly Gly Tyr Arg Cys Ser Trp Ala Pro Glu Thr Trp Val Cys Asp Asn (2) INFORMATION FOR SEQ ID NO:105:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:105:

```
His Ser Ala

Gly Tyr Leu Cys Asn Phe Gly Pro Ile Thr Trp Asp Cys Val Ser Ser
 1               5                  10                  15
Ala Gln Ser Glu Met Gln Ile Gly Gly
            20              25
```

(2) INFORMATION FOR SEQ ID NO:106:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:106:

```
Gly Gly Ala Glu Leu Gln Tyr Cys Lys Ile Gly Pro Glu Thr Trp Val
 1               5                  10                  15
Cys Asp Trp Pro His Ile Gly Gly
            20
```

(2) INFORMATION FOR SEQ ID NO:107:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:107:

```
Gly Gly Pro Tyr Glu Gly Tyr Cys Ser Gly Gly Pro Val Thr Trp Glu
 1               5                  10                  15
Cys Cys Val Ser Val Cys Gly Gly
            20
```

(2) INFORMATION FOR SEQ ID NO:108:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:108:

```
Gly Gly Gln Pro Leu Pro Tyr Cys Ser Pro Gly Pro Thr Thr Trp Phe
 1               5                  10                  15
Cys Ile Asn Trp Leu Phe Gly Gly
            20
```

( 2 ) INFORMATION FOR SEQ ID NO:109:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:109:

```
Gly Gly Cys Ser Tyr Gly Tyr Cys Pro Met Gly Pro Phe Thr Trp Met
 1               5                   10                  15
Cys Arg Gln Arg Arg Leu Gly Gly
                20
```

( 2 ) INFORMATION FOR SEQ ID NO:110:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:110:

```
Gly Gly Val Arg Gly Ser Tyr Cys Gln Ser Gly Pro Pro Thr Trp Gln
 1               5                   10                  15
Cys Asp Leu Arg Phe Phe Gly Gly
                20
```

( 2 ) INFORMATION FOR SEQ ID NO:111:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:111:

```
Gly Gly Arg Cys Ala Arg Tyr Cys Ala Cys Gly Pro Gly Thr Trp Asn
 1               5                   10                  15
Cys Leu Gly Arg Cys Gln Gly Gly
                20
```

( 2 ) INFORMATION FOR SEQ ID NO:112:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:112:

```
Gly Gly Leu Gly Arg Cys Tyr Cys Val Tyr Gly Pro Leu Thr Trp Trp
 1               5                   10                  15
Cys Ser Gln Thr Ser Leu Gly Gly
                20
```

( 2 ) INFORMATION FOR SEQ ID NO:113:

( i ) SEQUENCE CHARACTERISTICS:

(A) LENGTH: 24 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:113:

Gly Gly Leu Cys Val Trp Tyr Cys Ser Ala Gly Pro Trp Thr Trp Tyr
1               5                   10                  15

Cys Ile Tyr Arg Ser Ala Gly Gly
                20

(2) INFORMATION FOR SEQ ID NO:114:

(i) SEQUENCE CHARACTERISTICS:
            (A) LENGTH: 24 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:114:

Gly Gly Lys Pro Gly Pro Tyr Cys Ser Phe Gly Pro Glu Thr Trp Val
1               5                   10                  15

Cys Thr Ala Leu Gly Met Gly Gly
                20

(2) INFORMATION FOR SEQ ID NO:115:

(i) SEQUENCE CHARACTERISTICS:
            (A) LENGTH: 24 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:115:

Gly Gly Arg Leu Gly Glu Tyr Cys Glu Ile Gly Pro Ile Thr Trp Ile
1               5                   10                  15

Cys Arg Leu Phe Leu Pro Gly Gly
                20

(2) INFORMATION FOR SEQ ID NO:116:

(i) SEQUENCE CHARACTERISTICS:
            (A) LENGTH: 24 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:116:

Gly Gly Pro Gly Leu Gly Tyr Cys Asp Phe Gly Pro Leu Thr Trp Val
1               5                   10                  15

Cys Asp Gly Ser Val Asp Gly Gly
                20

(2) INFORMATION FOR SEQ ID NO:117:

(i) SEQUENCE CHARACTERISTICS:
            (A) LENGTH: 24 amino acids
            (B) TYPE: amino acid
            (C) STRANDEDNESS:
            (D) TOPOLOGY: linear ( i i ) MOLECULE TYPE: peptide ( x i ) SEQUENCE DESCRIPTION: SEQ ID NO:117:

```
Gly  Gly  Leu  Ser  Ser  Ala  Tyr  Cys  Arg  Tyr  Gly  Pro  Glu  Thr  Trp  Ile
1                   5                        10                       15
Cys  Trp  Ala  Gly  Thr  Gly  Gly  Gly
                    20
```

( 2 ) INFORMATION FOR SEQ ID NO:118:

( i ) SEQUENCE CHARACTERISTICS:
      ( A ) LENGTH: 24 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:118:

```
Gly  Gly  Val  Leu  His  Leu  Tyr  Cys  Tyr  Tyr  Gly  Pro  Glu  Thr  Trp  Asp
1                   5                        10                       15
Cys  Leu  Pro  Ile  Lys  Ala  Gly  Gly
                    20
```

( 2 ) INFORMATION FOR SEQ ID NO:119:

( i ) SEQUENCE CHARACTERISTICS:
      ( A ) LENGTH: 24 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:119:

```
Gly  Gly  Gly  Gly  Gly  Val  Tyr  Cys  Leu  Val  Gly  Pro  Val  Thr  Trp  Leu
1                   5                        10                       15
Cys  Gly  Pro  Ala  Ala  Met  Gly  Gly
                    20
```

( 2 ) INFORMATION FOR SEQ ID NO:120:

( i ) SEQUENCE CHARACTERISTICS:
      ( A ) LENGTH: 24 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:120:

```
Gly  Gly  Leu  Thr  Arg  Asn  Tyr  Cys  Arg  Ile  Gly  Pro  Glu  Thr  Trp  Ile
1                   5                        10                       15
Cys  Gln  Glu  Val  Ala  Ile  Gly  Gly
                    20
```

( 2 ) INFORMATION FOR SEQ ID NO:121:

( i ) SEQUENCE CHARACTERISTICS:
      ( A ) LENGTH: 24 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:121:

Gly Gly Trp Ser Glu Arg Tyr Cys Val Leu Gly Pro Leu Thr Trp Glu
1               5                           10                          15

Cys Val His Leu Phe Ala Gly Gly
                20

( 2 ) INFORMATION FOR SEQ ID NO:122:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:122:

Gly Gly Met Pro Leu Lys Tyr Cys Gly Met Gly Pro Val Thr Trp Val
1               5                           10                          15

Cys Cys Glu Ala Val Ser Gly Gly
                20

( 2 ) INFORMATION FOR SEQ ID NO:123:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:123:

Gly Gly Ser Val Met Arg Tyr Cys His Phe Gly Pro Glu Thr Trp Ile
1               5                           10                          15

Cys Pro Tyr Asp Met Pro Gly Gly
                20

( 2 ) INFORMATION FOR SEQ ID NO:124:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:124:

Gly Gly Ala Leu Tyr Pro Tyr Cys Leu Ile Gly Pro Met Thr Trp Val
1               5                           10                          15

Cys Gln Val Gly Trp Ile Gly Gly
                20

( 2 ) INFORMATION FOR SEQ ID NO:125:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:125:

Gly Gly Thr Tyr Gly Asn Tyr Cys Arg Gly Gly Pro Gly Thr Trp His
1               5                           10                          15

```
Cys Glu Asp Thr Arg Gly Gly Gly
              20
```

(2) INFORMATION FOR SEQ ID NO:126:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:126:

```
Gly Gly Ala Ser Tyr Cys Tyr Cys Ser Lys Gly Pro Ala Thr Trp Lys
1               5                   10                  15
Cys Val Gly Ser Ile Leu Gly Gly
              20
```

(2) INFORMATION FOR SEQ ID NO:127:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:127:

```
Gly Gly Ser Leu Ala Ala Tyr Cys Leu Gln Gly Pro Lys Thr Trp Pro
1               5                   10                  15
Cys Val Arg Arg Arg Leu Gly Gly
              20
```

(2) INFORMATION FOR SEQ ID NO:128:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:128:

```
Gly Gly Thr Asp Ser Leu Tyr Cys Lys Leu Gly Pro Leu Thr Trp His
1               5                   10                  15
Cys Gln Leu Tyr Gln Lys Gly Gly
              20
```

(2) INFORMATION FOR SEQ ID NO:129:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:129:

```
Gly Ile Ser Gln Gln Tyr Cys Trp Arg Gly Pro Ala Thr Trp Val Cys
1               5                   10                  15
Leu Glu Trp Glu Leu Gly Gly
              20
```

( 2 ) INFORMATION FOR SEQ ID NO:130:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:130:

```
Arg  Thr  Lys  Glu  Tyr  Ser  Cys  Gln  Met  Gly  Pro  Leu  Thr  Trp  Ile  Cys
1                  5                      10                         15
Val  Pro  Lys  Ser
                20
```

( 2 ) INFORMATION FOR SEQ ID NO:131:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:131:

```
Ser  Lys  Ala  Arg  Tyr  Met  Cys  His  Met  Gly  Pro  Leu  Thr  Trp  Val  Cys
1                  5                      10                         15
Arg  Pro  Glu  Val
                20
```

( 2 ) INFORMATION FOR SEQ ID NO:132:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:132:

```
Gly  Gly  Lys  Ala  Tyr  Met  Cys  Arg  Leu  Gly  Pro  Val  Thr  Trp  Val  Cys
1                  5                      10                         15
Ser  Pro  Arg  Ile  Lys  Leu
                20
```

( 2 ) INFORMATION FOR SEQ ID NO:133:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:133:

```
Leu  Leu  Arg  Gly  Tyr  Glu  Cys  Tyr  Met  Gly  Pro  Leu  Thr  Trp  Val  Cys
1                  5                      10                         15
Arg  Ser  Ser  Lys  Pro  Arg
                20
```

( 2 ) INFORMATION FOR SEQ ID NO:134:

( i ) SEQUENCE CHARACTERISTICS:
        ( A ) LENGTH: 22 amino acids (B) TYPE: amino acid
(C) STRANDEDNESS:
(D) TOPOLOGY: linear (i i) MOLECULE TYPE: peptide (x i) SEQUENCE DESCRIPTION: SEQ ID NO:134:

```
Asn Gly Arg Thr Tyr Ser Cys Gln Leu Gly Pro Val Thr Trp Val Cys
1               5                   10                  15
Ser Arg Gly Val Arg Arg
            20
```

(2) INFORMATION FOR SEQ ID NO:135:

(i) SEQUENCE CHARACTERISTICS:
(A) LENGTH: 19 amino acids
(B) TYPE: amino acid
(C) STRANDEDNESS:
(D) TOPOLOGY: linear (i i) MOLECULE TYPE: peptide (x i) SEQUENCE DESCRIPTION: SEQ ID NO:135:

```
Met Lys Thr Lys Tyr Lys Cys Tyr Met Gly Pro Leu Thr Trp Val Cys
1               5                   10                  15
Glu Gly Ser
```

(2) INFORMATION FOR SEQ ID NO:136:

(i) SEQUENCE CHARACTERISTICS:
(A) LENGTH: 19 amino acids
(B) TYPE: amino acid
(C) STRANDEDNESS:
(D) TOPOLOGY: linear (i i) MOLECULE TYPE: peptide (x i) SEQUENCE DESCRIPTION: SEQ ID NO:136:

```
Ser Lys Thr Lys Tyr Arg Cys Glu Met Gly Pro Leu Thr Trp Val Cys
1               5                   10                  15
Glu Arg Trp
```

(2) INFORMATION FOR SEQ ID NO:137:

(i) SEQUENCE CHARACTERISTICS:
(A) LENGTH: 22 amino acids
(B) TYPE: amino acid
(C) STRANDEDNESS:
(D) TOPOLOGY: linear (i i) MOLECULE TYPE: peptide (x i) SEQUENCE DESCRIPTION: SEQ ID NO:137:

```
Leu Thr Arg Leu Tyr Ser Cys His Met Gly Pro Ser Thr Trp Val Cys
1               5                   10                  15
Ser Thr Ala Leu Arg Lys
            20
```

(2) INFORMATION FOR SEQ ID NO:138:

(i) SEQUENCE CHARACTERISTICS:
(A) LENGTH: 22 amino acids
(B) TYPE: amino acid
(C) STRANDEDNESS:
(D) TOPOLOGY: linear (i i) MOLECULE TYPE: peptide ( x i ) SEQUENCE DESCRIPTION: SEQ ID NO:138:

Arg Gly Gln Leu Tyr Ala Cys His Phe Gly Pro Val Thr Trp Val Cys
1               5                   10                  15

Lys Arg Arg Lys Arg Val
            20

( 2 ) INFORMATION FOR SEQ ID NO:139:

( i ) SEQUENCE CHARACTERISTICS:
      ( A ) LENGTH: 22 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:139:

Ser Gly Ile Leu Tyr Glu Cys His Met Gly Pro Leu Thr Trp Val Cys
1               5                   10                  15

Thr Pro Ser Arg Arg Arg
            20

( 2 ) INFORMATION FOR SEQ ID NO:140:

( i ) SEQUENCE CHARACTERISTICS:
      ( A ) LENGTH: 20 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:140:

Gly Ser Lys Thr Tyr Ser Cys Gln Leu Gly Pro Val Thr Trp Val Cys
1               5                   10                  15

Gly Arg Lys Arg
            20

( 2 ) INFORMATION FOR SEQ ID NO:141:

( i ) SEQUENCE CHARACTERISTICS:
      ( A ) LENGTH: 22 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:141:

Ala Arg Gly Lys Tyr Gln Cys Gln Phe Gly Pro Leu Thr Trp Glu Cys
1               5                   10                  15

Leu Pro Ile Arg Pro Arg
            20

( 2 ) INFORMATION FOR SEQ ID NO:142:

( i ) SEQUENCE CHARACTERISTICS:
      ( A ) LENGTH: 18 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO:142:

Val Thr Arg Met Tyr Arg Cys Arg Met Gly Pro Leu Thr Trp Val Cys
1               5                   10                  15

Glu Arg ( 2 ) INFORMATION FOR SEQ ID NO:143:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:143:

Lys Pro Ser Leu Tyr Glu Cys His Leu Gly Pro Leu Thr Trp Glu Cys
1               5                   10                  15
Arg Pro Arg Arg Arg Glu
            20

( 2 ) INFORMATION FOR SEQ ID NO:144:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:144:

Arg Gly His Met Tyr Ser Cys Gln Leu Gly Pro Val Thr Trp Val Cys
1               5                   10                  15
Lys Pro Leu Ser Gly Arg
            20

( 2 ) INFORMATION FOR SEQ ID NO:145:

( i ) SEQUENCE CHARACTERISTICS:
        ( A ) LENGTH: 25 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:145:

Ile Thr Pro Thr Tyr His Cys Lys Phe Gly Pro Gln Thr Trp Val Cys
1               5                   10                  15
Ala Pro Lys Arg Ser Ala Leu Thr Lys
            20                  25

( 2 ) INFORMATION FOR SEQ ID NO:146:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:146:

Gly Asn Arg Met Tyr Gln Cys His Met Gly Pro Leu Thr Trp Val Cys
1               5                   10                  15
Gln Pro Thr Arg Ile His
            20

( 2 ) INFORMATION FOR SEQ ID NO:147:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:147:

```
Met  Lys  Thr  Lys  Tyr  Lys  Cys  Tyr  Met  Gly  Pro  Leu  Thr  Trp  Val  Cys
1                   5                        10                       15
Glu  Gly  Ser  Arg  Leu  Lys
                20
```

( 2 ) INFORMATION FOR SEQ ID NO:148:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:148:

```
His  Leu  Gly  Lys  Tyr  Asp  Cys  Ser  Phe  Gly  Pro  Gln  Thr  Trp  Val  Cys
1                   5                        10                       15
Lys  Pro  Arg  Arg  Ser  Leu
                20
```

( 2 ) INFORMATION FOR SEQ ID NO:149:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:149:

```
Glu  Arg  Arg  Val  Tyr  Glu  Cys  Gln  Met  Gly  Pro  Leu  Thr  Trp  Glu  Cys
1                   5                        10                       15
Lys  Pro  Gly  Val  Lys  Gly
                20
```

( 2 ) INFORMATION FOR SEQ ID NO:150:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:150:

```
Arg  Gly  Arg  Gly  Tyr  Ser  Cys  Gln  Met  Gly  Pro  Val  Thr  Trp  Val  Cys
1                   5                        10                       15
Lys  Arg  Glu  Arg  Tyr  Phe
                20
```

( 2 ) INFORMATION FOR SEQ ID NO:151:

( i ) SEQUENCE CHARACTERISTICS:
        ( A ) LENGTH: 22 amino acids (B) TYPE: amino acid
(C) STRANDEDNESS:
(D) TOPOLOGY: linear (ii) MOLECULE TYPE: peptide (xi) SEQUENCE DESCRIPTION: SEQ ID NO:151:

Arg Leu Arg Glu Tyr Arg Cys His Met Gly Pro Gln Thr Trp Val Cys
1               5                   10                  15
Asn Gly His His Ser Lys
            20

(2) INFORMATION FOR SEQ ID NO:152:

(i) SEQUENCE CHARACTERISTICS:
    (A) LENGTH: 22 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:152:

Ser Gly Ala Leu Tyr Asp Cys Gln Met Gly Pro Ile Thr Trp Val Cys
1               5                   10                  15
Arg Ala Asn Arg Gln Lys
            20

(2) INFORMATION FOR SEQ ID NO:153:

(i) SEQUENCE CHARACTERISTICS:
    (A) LENGTH: 22 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:153:

Thr Asn Gln Val Tyr Gly Cys Lys Phe Gly Pro Lys Thr Trp Val Cys
1               5                   10                  15
Lys Pro Ala Pro Arg Ile
            20

(2) INFORMATION FOR SEQ ID NO:154:

(i) SEQUENCE CHARACTERISTICS:
    (A) LENGTH: 22 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:154:

Thr Arg Gly Met Tyr Ala Cys His Met Gly Pro Gln Thr Trp Val Cys
1               5                   10                  15
Arg Pro Thr Gln Pro Arg
            20

(2) INFORMATION FOR SEQ ID NO:155:

(i) SEQUENCE CHARACTERISTICS:
    (A) LENGTH: 22 amino acids
    (B) TYPE: amino acid
    (C) STRANDEDNESS:
    (D) TOPOLOGY: linear (i i) MOLECULE TYPE: peptide (x i) SEQUENCE DESCRIPTION: SEQ ID NO:155:

Val Leu Ser Asn Tyr Glu Cys Thr Met Gly Pro Lys Thr Trp Val Cys
1               5                   10                  15

Lys Pro Leu Arg Leu Lys
            20

(2) INFORMATION FOR SEQ ID NO:156:

(i) SEQUENCE CHARACTERISTICS:
      (A) LENGTH: 22 amino acids
      (B) TYPE: amino acid
      (C) STRANDEDNESS:
      (D) TOPOLOGY: linear (i i) MOLECULE TYPE: peptide (x i) SEQUENCE DESCRIPTION: SEQ ID NO:156:

Ala Leu Lys Lys Tyr Asp Cys Tyr Phe Gly Pro Glu Thr Trp Glu Cys
1               5                   10                  15

Leu Ala Arg Arg Pro His
            20

(2) INFORMATION FOR SEQ ID NO:157:

(i) SEQUENCE CHARACTERISTICS:
      (A) LENGTH: 18 amino acids
      (B) TYPE: amino acid
      (C) STRANDEDNESS:
      (D) TOPOLOGY: linear (i i) MOLECULE TYPE: peptide (x i) SEQUENCE DESCRIPTION: SEQ ID NO:157:

Glu Arg Arg Phe Tyr Lys Cys Arg Phe Gly Pro Glu Thr Trp Glu Cys
1               5                   10                  15

Thr Leu (2) INFORMATION FOR SEQ ID NO:158:

(i) SEQUENCE CHARACTERISTICS:
      (A) LENGTH: 22 amino acids
      (B) TYPE: amino acid
      (C) STRANDEDNESS:
      (D) TOPOLOGY: linear (i i) MOLECULE TYPE: peptide (x i) SEQUENCE DESCRIPTION: SEQ ID NO:158:

Phe Gly Gln Glu Tyr Arg Cys His Leu Gly Pro Glu Thr Trp Gln Cys
1               5                   10                  15

Ser Pro Val Arg Val Gly
            20

(2) INFORMATION FOR SEQ ID NO:159:

(i) SEQUENCE CHARACTERISTICS:
      (A) LENGTH: 21 amino acids
      (B) TYPE: amino acid
      (C) STRANDEDNESS:
      (D) TOPOLOGY: linear (i i) MOLECULE TYPE: peptide (x i) SEQUENCE DESCRIPTION: SEQ ID NO:159:

Phe Arg Pro Glu Tyr Met Cys Arg Met Gly Pro Glu Thr Trp Glu Cys

```
            1               5                   10                  15

Gly  Gly  Ala  Arg  Pro
                          20
```

( 2 ) INFORMATION FOR SEQ ID NO:160:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:160:

```
        Gly  Ser  Arg  Lys  Tyr  Trp  Cys  Arg  Met  Gly  Pro  Glu  Thr  Trp  Glu  Cys
        1                 5                        10                       15

Met  Lys  Pro  Val  Arg  Leu
                          20
```

( 2 ) INFORMATION FOR SEQ ID NO:161:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:161:

```
        Gly  Leu  Lys  Ala  Tyr  Gly  Cys  Arg  Tyr  Gly  Pro  Glu  Thr  Trp  Asp  Cys
        1                 5                        10                       15

Arg  Ser  Val  Ile  Leu  Ile
                          20
```

( 2 ) INFORMATION FOR SEQ ID NO:162:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:162:

```
        Ile  Arg  Gln  Pro  Tyr  Ile  Cys  His  Met  Gly  Pro  Glu  Thr  Trp  Glu  Cys
        1                 5                        10                       15

Gly  Arg  Tyr  Pro  Ala  Gly
                          20
```

( 2 ) INFORMATION FOR SEQ ID NO:163:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:163:

```
        Lys  Gly  Ala  Ser  Tyr  His  Cys  Ile  Met  Gly  Pro  Glu  Thr  Trp  Glu  Cys
        1                 5                        10                       15

Ile  Pro  Gln  Arg  Val  Trp
                          20
```

( 2 ) INFORMATION FOR SEQ ID NO:164:

( i ) SEQUENCE CHARACTERISTICS:
    ( A ) LENGTH: 22 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:164:

```
Met Lys Gln Leu Tyr Ser Cys Ile Met Gly Pro Glu Thr Trp Glu Cys
1               5                   10                  15
Arg Pro Gly Val Glu Arg
            20
```

( 2 ) INFORMATION FOR SEQ ID NO:165:

( i ) SEQUENCE CHARACTERISTICS:
    ( A ) LENGTH: 22 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:165:

```
Gln Arg His Tyr Tyr Arg Cys Ala Leu Gly Pro Glu Thr Trp Glu Cys
1               5                   10                  15
Arg Pro Met Ser Pro Glu
            20
```

( 2 ) INFORMATION FOR SEQ ID NO:166:

( i ) SEQUENCE CHARACTERISTICS:
    ( A ) LENGTH: 22 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:166:

```
Thr Lys Arg Leu Tyr His Cys His Met Gly Pro Glu Thr Trp Glu Cys
1               5                   10                  15
His Gly Pro Met Arg Lys
            20
```

( 2 ) INFORMATION FOR SEQ ID NO:167:

( i ) SEQUENCE CHARACTERISTICS:
    ( A ) LENGTH: 20 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:167:

```
Thr Arg Pro Ser Tyr Arg Cys Ala Phe Gly Pro Val Thr Trp Glu Cys
1               5                   10                  15
Ile Pro Ala Arg
            20
```

( 2 ) INFORMATION FOR SEQ ID NO:168:

( i ) SEQUENCE CHARACTERISTICS:
    ( A ) LENGTH: 22 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:168:

```
Arg His Lys Ser Tyr Val Cys Thr Phe Gly Pro Glu Thr Trp Glu Cys
1               5                   10                  15
Thr Gly Ala Ile Arg Arg
            20
```

( 2 ) INFORMATION FOR SEQ ID NO:169:

( i ) SEQUENCE CHARACTERISTICS:
    ( A ) LENGTH: 22 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:169:

```
Arg Gly Arg Met Tyr Asn Cys Arg Met Gly Pro Glu Thr Trp Glu Cys
1               5                   10                  15
Lys Gly Gln Ser Lys Asp
            20
```

( 2 ) INFORMATION FOR SEQ ID NO:170:

( i ) SEQUENCE CHARACTERISTICS:
    ( A ) LENGTH: 22 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:170:

```
Arg Arg Arg Tyr Tyr Arg Cys Trp Met Gly Pro Glu Thr Trp Glu Cys
1               5                   10                  15
Ser Pro Val Ser Asn Lys
            20
```

( 2 ) INFORMATION FOR SEQ ID NO:171:

( i ) SEQUENCE CHARACTERISTICS:
    ( A ) LENGTH: 22 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:171:

```
Val Ala Asp Asn Tyr Asp Cys Pro Ile Gly Pro Val Thr Trp Glu Cys
1               5                   10                  15
Ile His Val Arg Ala Ser
            20
```

( 2 ) INFORMATION FOR SEQ ID NO:172:

( i ) SEQUENCE CHARACTERISTICS:
    ( A ) LENGTH: 21 amino acids
    ( B ) TYPE: amino acid
    ( C ) STRANDEDNESS:

(D) TOPOLOGY: linear (ii) MOLECULE TYPE: peptide (xi) SEQUENCE DESCRIPTION: SEQ ID NO:172:

Val Gln Lys Lys Tyr Leu Cys His Phe Gly Pro Glu Thr Trp Glu Cys
1               5                           10                          15

Gly Pro Asp Arg Asp
            20

(2) INFORMATION FOR SEQ ID NO:173:

(i) SEQUENCE CHARACTERISTICS:
    (A) LENGTH: 21 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:173:

Trp Gln Thr Trp Tyr Ile Cys Glu Arg Gly Pro Glu Thr Trp Glu Cys
1               5                           10                          15

Arg Trp Leu Val Leu
            20

(2) INFORMATION FOR SEQ ID NO:174:

(i) SEQUENCE CHARACTERISTICS:
    (A) LENGTH: 22 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:174:

Tyr Arg Met Pro Tyr Arg Cys Lys Met Gly Pro Glu Thr Trp Glu Cys
1               5                           10                          15

Val Gly Gly Arg Gly Arg
            20

(2) INFORMATION FOR SEQ ID NO:175:

(i) SEQUENCE CHARACTERISTICS:
    (A) LENGTH: 22 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:175:

Tyr Ser Arg Glu Tyr Ser Cys Arg Met Gly Pro Glu Thr Trp Glu Cys
1               5                           10                          15

Xaa Arg Gly Phe Leu Arg
            20

(2) INFORMATION FOR SEQ ID NO:176:

(i) SEQUENCE CHARACTERISTICS:
    (A) LENGTH: 22 amino acids
    (B) TYPE: amino acid
    (C) STRANDEDNESS:
    (D) TOPOLOGY: linear (ii) MOLECULE TYPE: peptide ( x i ) SEQUENCE DESCRIPTION: SEQ ID NO:176:

Arg Ser Met Trp Tyr Arg Cys Gln Met Gly Pro Gln Thr Trp Val Cys
1               5                   10                  15

Gly Pro Arg Ser Ala Ser
            20

( 2 ) INFORMATION FOR SEQ ID NO:177:

( i ) SEQUENCE CHARACTERISTICS:
         ( A ) LENGTH: 22 amino acids
         ( B ) TYPE: amino acid
         ( C ) STRANDEDNESS:
         ( D ) TOPOLOGY: linear ( i i ) MOLECULE TYPE: peptide ( x i ) SEQUENCE DESCRIPTION: SEQ ID NO:177:

Ser Arg Arg Glu Tyr Ile Cys His Leu Gly Pro Gln Thr Trp Val Cys
1               5                   10                  15

Gly Pro Gly Gly Arg Lys
            20

( 2 ) INFORMATION FOR SEQ ID NO:178:

( i ) SEQUENCE CHARACTERISTICS:
         ( A ) LENGTH: 22 amino acids
         ( B ) TYPE: amino acid
         ( C ) STRANDEDNESS:
         ( D ) TOPOLOGY: linear ( i i ) MOLECULE TYPE: peptide ( x i ) SEQUENCE DESCRIPTION: SEQ ID NO:178:

Gly Ser Pro Ser Tyr His Cys His Leu Gly Pro Leu Thr Trp Val Cys
1               5                   10                  15

Lys Pro His Arg Met Arg
            20

( 2 ) INFORMATION FOR SEQ ID NO:179:

( i ) SEQUENCE CHARACTERISTICS:
         ( A ) LENGTH: 21 amino acids
         ( B ) TYPE: amino acid
         ( C ) STRANDEDNESS:
         ( D ) TOPOLOGY: linear ( i i ) MOLECULE TYPE: peptide ( x i ) SEQUENCE DESCRIPTION: SEQ ID NO:179:

Met Val Gly Arg Tyr Gln Cys His Met Gly Pro Arg Thr Trp Val Cys
1               5                   10                  15

Lys Pro Trp His Gly
            20

( 2 ) INFORMATION FOR SEQ ID NO:180:

( i ) SEQUENCE CHARACTERISTICS:
         ( A ) LENGTH: 22 amino acids
         ( B ) TYPE: amino acid
         ( C ) STRANDEDNESS:
         ( D ) TOPOLOGY: linear ( i i ) MOLECULE TYPE: peptide ( x i ) SEQUENCE DESCRIPTION: SEQ ID NO:180:

Gly Thr Ala Arg Tyr Gln Cys His Phe Gly Pro Leu Thr Trp Val Cys
1               5                   10                  15

```
        Lys   Pro   Ser   Leu   Lys   Gly
                          20
```

( 2 ) INFORMATION FOR SEQ ID NO:181:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:181:

```
Glu   Leu   Arg   Gly   Tyr   Ile   Cys   His   Phe   Gly   Pro   Val   Thr   Trp   Val   Cys
1                       5                             10                              15

Lys   Pro   Asn   Gly   Ser   Arg
                        20
```

( 2 ) INFORMATION FOR SEQ ID NO:182:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:182:

```
Leu   Lys   Gln   Gly   Tyr   Gln   Cys   Gln   Leu   Gly   Pro   Gln   Thr   Trp   Val   Cys
1                       5                             10                              15

Arg   Pro   Leu   Arg   Met   Pro
                        20
```

( 2 ) INFORMATION FOR SEQ ID NO:183:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:183:

```
Lys   Glu   Arg   Lys   Tyr   Glu   Cys   Gln   Phe   Gly   Pro   Arg   Thr   Trp   Val   Cys
1                       5                             10                              15

Gln   Pro   Thr   Arg   Ala   Asn
                        20
```

( 2 ) INFORMATION FOR SEQ ID NO:184:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:184:

```
Val   Arg   Lys   Val   Tyr   Ala   Cys   His   Met   Gly   Pro   Val   Thr   Trp   Val   Cys
1                       5                             10                              15

Val   Pro   Gly   Tyr   Lys   Gly
                        20
```

( 2 ) INFORMATION FOR SEQ ID NO:185:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:185:

```
Ser  Gly  Gln  Arg  Tyr  Val  Cys  Arg  Met  Gly  Pro  Glu  Thr  Trp  Val  Cys
1                    5                        10                       15
Arg  Ser  Tyr  Arg  Gly  Leu
               20
```

( 2 ) INFORMATION FOR SEQ ID NO:186:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:186:

```
Glu  Arg  Arg  Ser  Tyr  Ser  Cys  Gln  Met  Gly  Pro  Val  Thr  Trp  Val  Cys
1                    5                        10                       15
Gly  Arg  Gln  Met  Gly  Gln
               20
```

( 2 ) INFORMATION FOR SEQ ID NO:187:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:187:

```
Val  Lys  Asn  Asn  Tyr  Arg  Cys  Gln  Phe  Gly  Pro  Val  Thr  Trp  Val  Cys
1                    5                        10                       15
Lys  Ala  Phe  Arg
               20
```

( 2 ) INFORMATION FOR SEQ ID NO:188:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:188:

```
Ser  Gly  Ala  Ser  Tyr  Asp  Cys  Gln  Met  Gly  Pro  Ile  Thr  Trp  Val  Cys
1                    5                        10                       15
Arg  Ala  Asn  Arg  Gln  Lys
               20
```

( 2 ) INFORMATION FOR SEQ ID NO:189:

( i ) SEQUENCE CHARACTERISTICS:

(A) LENGTH: 20 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:189:

```
Gly Gly Thr Thr Ser Cys His Phe Gly Pro Leu Thr Trp Val Cys Lys
1               5                   10                  15
Pro Gln Gly Gly
            20
```

(2) INFORMATION FOR SEQ ID NO:190:

(i) SEQUENCE CHARACTERISTICS:
(A) LENGTH: 20 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:190:

```
Gly Gly Thr Phe Ser Cys His Phe Gly Pro Leu Thr Trp Val Cys Lys
1               5                   10                  15
Pro Gln Gly Gly
            20
```

(2) INFORMATION FOR SEQ ID NO:191:

(i) SEQUENCE CHARACTERISTICS:
(A) LENGTH: 20 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:191:

```
Gly Gly Thr Tyr Ser Cys His Phe Gly Ala Leu Thr Trp Val Cys Lys
1               5                   10                  15
Pro Gln Gly Gly
            20
```

(2) INFORMATION FOR SEQ ID NO:192:

(i) SEQUENCE CHARACTERISTICS:
(A) LENGTH: 20 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:192:

```
Gly Gly Thr Tyr Ser Cys His Phe Gly Pro Leu Ala Trp Val Cys Lys
1               5                   10                  15
Pro Gln Gly Gly
            20
```

(2) INFORMATION FOR SEQ ID NO:193:

(i) SEQUENCE CHARACTERISTICS:
(A) LENGTH: 20 amino acids
(B) TYPE: amino acid
(C) STRANDEDNESS:
(D) TOPOLOGY: linear ( i i ) MOLECULE TYPE: peptide ( x i ) SEQUENCE DESCRIPTION: SEQ ID NO:193:

Gly Gly Thr Tyr Ser Cys His Phe Ala Pro Leu Thr Trp Val Cys Lys
1               5                   10                  15
Pro Gln Gly Gly
            20

( 2 ) INFORMATION FOR SEQ ID NO:194:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:194:

Gly Gly Thr Tyr Ser Cys His Phe Gly Pro Ala Thr Trp Val Cys Lys
1               5                   10                  15
Pro Gln Gly Gly
            20

( 2 ) INFORMATION FOR SEQ ID NO:195:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:195:

Gly Gly Thr Tyr Ser Cys His Phe Gly Pro Leu Thr Ala Val Cys Lys
1               5                   10                  15
Pro Gln Gly Gly
            20

( 2 ) INFORMATION FOR SEQ ID NO:196:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:196:

Gly Gly Thr Tyr Ser Cys His Phe Gly Pro Leu Thr Phe Val Cys Lys
1               5                   10                  15
Pro Gln Gly Gly
            20

( 2 ) INFORMATION FOR SEQ ID NO:197:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:197:

```
Thr  Tyr  Ser  Cys  His  Phe  Gly  Pro  Leu  Thr  Trp  Val  Cys  Lys  Pro  Gln
1                   5                        10                      15
```

(2) INFORMATION FOR SEQ ID NO:198:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:198:

```
Tyr  Ser  Cys  His  Phe  Gly  Pro  Leu  Thr  Trp  Val  Cys  Lys  Pro
1              5                        10
```

(2) INFORMATION FOR SEQ ID NO:199:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:199:

```
Tyr  Ser  Cys  His  Phe  Gly  Ala  Leu  Thr  Trp  Val  Cys  Lys
1              5                        10
```

(2) INFORMATION FOR SEQ ID NO:200:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:200:

```
Ser  Cys  His  Phe  Gly  Pro  Leu  Thr  Trp  Val  Cys  Lys
1              5                        10
```

(2) INFORMATION FOR SEQ ID NO:201:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:201:

```
His  Phe  Gly  Pro  Leu  Thr  Trp  Val
1              5
```

(2) INFORMATION FOR SEQ ID NO:202:

(i) SEQUENCE CHARACTERISTICS:
        (A) LENGTH: 20 amino acids
        (B) TYPE: amino acid
        (C) STRANDEDNESS:
        (D) TOPOLOGY: circular (ii) MOLECULE TYPE: peptide (ix) FEATURE:

( A ) NAME/KEY: Cross-links
( B ) LOCATION: 6..16
( D ) OTHER INFORMATION: /product="OTHER"
/ note= "An amide bond joins the
delta carboxyl group of Glu at
position 6 to the epsilon amine group
of Lys at position 16"

( x i ) SEQUENCE DESCRIPTION: SEQ ID NO:202:

Gly Gly Thr Tyr Ser Glu His Phe Gly Pro Leu Thr Trp Val Lys Lys
1               5                   10                  15

Pro Gln Gly Gly
            20

( 2 ) INFORMATION FOR SEQ ID NO:203:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:203:

Gly Gly Thr Tyr Arg Cys Ser Met Gly Pro Met Thr Trp Val Cys Leu
1               5                   10                  15

Pro Met Gly Gly
            20

( 2 ) INFORMATION FOR SEQ ID NO:204:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:204:

Gly Gly Met Tyr Ser Cys Arg Met Gly Pro Met Thr Trp Val Cys Gly
1               5                   10                  15

Pro Ser Gly Gly
            20

( 2 ) INFORMATION FOR SEQ ID NO:205:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:205:

Gly Gly Trp Ala Trp Cys Arg Met Gly Pro Ile Thr Trp Val Cys Ser
1               5                   10                  15

Ala His Gly Gly
            20

( 2 ) INFORMATION FOR SEQ ID NO:206:

( i ) SEQUENCE CHARACTERISTICS:
( A ) LENGTH: 20 amino acids
( B ) TYPE: amino acid
( C ) STRANDEDNESS:

(D) TOPOLOGY: linear (ii) MOLECULE TYPE: peptide (xi) SEQUENCE DESCRIPTION: SEQ ID NO:206:

```
Gly Gly Met Tyr Ser Cys Arg Met Gly Pro Met Thr Trp Val Cys Ile
1               5                   10                  15
Pro Tyr Gly Gly
            20
```

(2) INFORMATION FOR SEQ ID NO:207:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:207:

```
Gly Gly Asp Tyr Thr Cys Arg Met Gly Pro Met Thr Trp Ile Cys Thr
1               5                   10                  15
Ala Thr Gly Gly
            20
```

(2) INFORMATION FOR SEQ ID NO:208:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:208:

```
Gly Gly Asn Tyr Leu Cys Arg Phe Gly Pro Gly Thr Trp Asp Cys Thr
1               5                   10                  15
Gly Phe Arg Gly
            20
```

(2) INFORMATION FOR SEQ ID NO:209:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:209:

```
Gly Gly Lys Asp Val Cys Arg Met Gly Pro Ile Thr Trp Asp Cys Arg
1               5                   10                  15
Ser Thr Gly Gly
            20
```

(2) INFORMATION FOR SEQ ID NO:210:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide ( x i ) SEQUENCE DESCRIPTION: SEQ ID NO:210:

Gly Gly Asn Tyr Leu Cys Arg Met Gly Pro Ala Thr Trp Val Cys Gly
1               5                           10                          15

Arg Met Gly Gly
            20

( 2 ) INFORMATION FOR SEQ ID NO:211:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:211:

Gly Gly Glu Tyr Lys Cys Arg Met Gly Pro Leu Thr Trp Val Cys Gln
1               5                           10                          15

Tyr Ala Gly Gly
            20

( 2 ) INFORMATION FOR SEQ ID NO:212:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:212:

Gly Gly Val Tyr Val Cys Arg Met Gly Pro Leu Thr Trp Glu Cys Thr
1               5                           10                          15

Ala Ser Gly Gly
            20

( 2 ) INFORMATION FOR SEQ ID NO:213:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:213:

Gly Gly Glu Tyr Ser Cys Arg Met Gly Pro Met Thr Trp Val Cys Ser
1               5                           10                          15

Pro Thr Gly Gly
            20

( 2 ) INFORMATION FOR SEQ ID NO:214:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:214:

Gly Gly Asn Tyr Ile Cys Arg Met Gly Pro Met Thr Trp Val Cys Thr
1               5                           10                          15

Ala    His    Gly    Gly
                             20

( 2 ) INFORMATION FOR SEQ ID NO:215:

( i ) SEQUENCE CHARACTERISTICS:
                ( A ) LENGTH: 20 amino acids
                ( B ) TYPE: amino acid
                ( C ) STRANDEDNESS:
                ( D ) TOPOLOGY: linear ( i i ) MOLECULE TYPE: peptide ( x i ) SEQUENCE DESCRIPTION: SEQ ID NO:215:

Gly    Gly    Asp    Tyr    Leu    Cys    Arg    Met    Gly    Pro    Ala    Thr    Trp    Val    Cys    Gly
        1                           5                                  1 0                                 1 5

Arg    Met    Gly    Gly
                             2 0

( 2 ) INFORMATION FOR SEQ ID NO:216:

( i ) SEQUENCE CHARACTERISTICS:
                ( A ) LENGTH: 20 amino acids
                ( B ) TYPE: amino acid
                ( C ) STRANDEDNESS:
                ( D ) TOPOLOGY: linear ( i i ) MOLECULE TYPE: peptide ( x i ) SEQUENCE DESCRIPTION: SEQ ID NO:216:

Gly    Gly    Leu    Tyr    Ser    Cys    Arg    Met    Gly    Pro    Ile    Thr    Trp    Val    Cys    Thr
        1                           5                                  1 0                                 1 5

Lys    Ala    Gly    Gly
                             2 0

( 2 ) INFORMATION FOR SEQ ID NO:217:

( i ) SEQUENCE CHARACTERISTICS:
                ( A ) LENGTH: 20 amino acids
                ( B ) TYPE: amino acid
                ( C ) STRANDEDNESS:
                ( D ) TOPOLOGY: linear ( i i ) MOLECULE TYPE: peptide ( x i ) SEQUENCE DESCRIPTION: SEQ ID NO:217:

Gly    Gly    Gly    Tyr    His    Cys    Arg    Met    Gly    Pro    Met    Thr    Trp    Val    Cys    Arg
        1                           5                                  1 0                                 1 5

Pro    Val    Gly    Gly
                             2 0

( 2 ) INFORMATION FOR SEQ ID NO:218:

( i ) SEQUENCE CHARACTERISTICS:
                ( A ) LENGTH: 20 amino acids
                ( B ) TYPE: amino acid
                ( C ) STRANDEDNESS:
                ( D ) TOPOLOGY: linear ( i i ) MOLECULE TYPE: peptide ( x i ) SEQUENCE DESCRIPTION: SEQ ID NO:218:

Gly    Gly    Leu    Tyr    Ser    Cys    Leu    Met    Gly    Pro    Ile    Thr    Trp    Leu    Cys    Lys
        1                           5                                  1 0                                 1 5

Pro    Lys    Gly    Gly
                             2 0

( 2 ) INFORMATION FOR SEQ ID NO:219:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:219:

```
Gly Gly Asp Tyr Ser Cys Arg Met Gly Pro Thr Thr Trp Val Cys Thr
 1               5                  10                  15
Pro Pro Gly Gly
            20
```

( 2 ) INFORMATION FOR SEQ ID NO:220:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:220:

```
Gly Gly Asp Tyr Trp Cys Arg Met Gly Pro Ser Thr Trp Glu Cys Asn
 1               5                  10                  15
Ala His Gly Gly
            20
```

( 2 ) INFORMATION FOR SEQ ID NO:221:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:221:

```
Gly Gly Lys Tyr Leu Cys Ser Phe Gly Pro Ile Thr Trp Val Cys Ala
 1               5                  10                  15
Arg Tyr Gly Gly
            20
```

( 2 ) INFORMATION FOR SEQ ID NO:222:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:222:

```
Gly Gly Leu Tyr Lys Cys Arg Leu Gly Pro Ile Thr Trp Val Cys Ser
 1               5                  10                  15
Pro Leu Gly Gly
            20
```

( 2 ) INFORMATION FOR SEQ ID NO:223:

( i ) SEQUENCE CHARACTERISTICS:

( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:223:

Gly Gly Ser Tyr Thr Cys Arg Phe Gly Pro Glu Thr Trp Val Cys Arg
1               5                   10                  15
Pro Asn Gly Gly
            20

( 2 ) INFORMATION FOR SEQ ID NO:224:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:224:

Gly Gly Ser Tyr Ser Cys Arg Met Gly Pro Ile Thr Trp Val Cys Lys
1               5                   10                  15
Pro Gly Gly Gly
            20

( 2 ) INFORMATION FOR SEQ ID NO:225:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:225:

Gly Gly Ser Tyr Thr Cys Arg Met Gly Pro Ile Thr Trp Val Cys Leu
1               5                   10                  15
Pro Ala Gly Gly
            20

( 2 ) INFORMATION FOR SEQ ID NO:226:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:226:

Gly Gly Asp Tyr Thr Cys Arg Met Gly Pro Ile Thr Trp Ile Cys Thr
1               5                   10                  15
Lys Ala Gly Gly
            20

( 2 ) INFORMATION FOR SEQ ID NO:227:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear (i i) MOLECULE TYPE: peptide (x i) SEQUENCE DESCRIPTION: SEQ ID NO:227:

```
Gly Gly Val Tyr Ser Cys Arg Met Gly Pro Thr Thr Trp Glu Cys Asn
1               5                   10                  15
Arg Tyr Val Gly
            20
```

(2) INFORMATION FOR SEQ ID NO:228:

(i) SEQUENCE CHARACTERISTICS:
        (A) LENGTH: 20 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:228:

```
Gly Gly Ala Tyr Leu Cys His Met Gly Pro Ile Thr Trp Val Cys Arg
1               5                   10                  15
Pro Gln Gly Gly
            20
```

(2) INFORMATION FOR SEQ ID NO:229:

(i) SEQUENCE CHARACTERISTICS:
        (A) LENGTH: 20 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:229:

```
Gly Gly Glu Tyr Ser Cys Arg Met Gly Pro Asn Thr Trp Val Cys Lys
1               5                   10                  15
Pro Val Gly Gly
            20
```

(2) INFORMATION FOR SEQ ID NO:230:

(i) SEQUENCE CHARACTERISTICS:
        (A) LENGTH: 20 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:230:

```
Gly Gly Leu Tyr Thr Cys Arg Met Gly Pro Ile Thr Trp Val Cys Leu
1               5                   10                  15
Leu Pro Gly Gly
            20
```

(2) INFORMATION FOR SEQ ID NO:231:

(i) SEQUENCE CHARACTERISTICS:
        (A) LENGTH: 20 amino acids
        (B) TYPE: amino acid
        (C) STRANDEDNESS:
        (D) TOPOLOGY: linear (i i) MOLECULE TYPE: peptide (x i) SEQUENCE DESCRIPTION: SEQ ID NO:231:

```
      Gly  Gly  Leu  Tyr  Thr  Cys  Arg  Met  Gly  Pro  Val  Thr  Trp  Val  Cys  Thr
      1              5                        10                       15

Gly  Ala  Gly  Gly
                    20
```

( 2 ) INFORMATION FOR SEQ ID NO:232:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:232:

```
      Gly  Gly  Val  Tyr  Lys  Cys  Arg  Met  Gly  Pro  Leu  Thr  Trp  Glu  Cys  Arg
      1              5                        10                       15

Pro  Thr  Gly  Gly
                    20
```

( 2 ) INFORMATION FOR SEQ ID NO:233:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:233:

```
      Gly  Gly  Ser  Tyr  Leu  Cys  Arg  Phe  Gly  Pro  Thr  Thr  Trp  Leu  Cys  Ser
      1              5                        10                       15

Ser  Ala  Gly  Gly
                    20
```

( 2 ) INFORMATION FOR SEQ ID NO:234:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:234:

```
      Gly  Gly  Ser  Tyr  Leu  Cys  Arg  Met  Gly  Pro  Thr  Thr  Trp  Val  Cys  Thr
      1              5                        10                       15

Arg  Met  Gly  Gly
                    20
```

( 2 ) INFORMATION FOR SEQ ID NO:235:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:235:

```
      Gly  Gly  Ser  Tyr  Leu  Cys  Arg  Phe  Gly  Pro  Thr  Thr  Trp  Leu  Cys  Thr
      1              5                        10                       15
```

```
         Gln  Arg  Gly  Gly
                         20
```

( 2 ) INFORMATION FOR SEQ ID NO:236:

( i ) SEQUENCE CHARACTERISTICS:
       ( A ) LENGTH: 20 amino acids
       ( B ) TYPE: amino acid
       ( C ) STRANDEDNESS:
       ( D ) TOPOLOGY: linear ( i i ) MOLECULE TYPE: peptide ( x i ) SEQUENCE DESCRIPTION: SEQ ID NO:236:

```
 Gly  Gly  Gln  Tyr  Leu  Cys  Thr  Phe  Gly  Pro  Ile  Thr  Trp  Leu  Cys  Arg
 1                   5                        10                       15

Gly  Ala  Gly  Gly
                20
```

( 2 ) INFORMATION FOR SEQ ID NO:237:

( i ) SEQUENCE CHARACTERISTICS:
       ( A ) LENGTH: 8 amino acids
       ( B ) TYPE: amino acid
       ( C ) STRANDEDNESS:
       ( D ) TOPOLOGY: linear ( i i ) MOLECULE TYPE: peptide ( x i ) SEQUENCE DESCRIPTION: SEQ ID NO:237:

```
 Arg  Ile  Gly  Pro  Ile  Thr  Trp  Val
 1                   5
```

( 2 ) INFORMATION FOR SEQ ID NO:238:

( i ) SEQUENCE CHARACTERISTICS:
       ( A ) LENGTH: 94 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:238:

```
CTCTCACTCC  GGAGGCNNKN  NKNNKTGTCG  KATKGGKCCK  ATKACKTGKG  TKTGTNNKNN      60

KNNKGGAGGC  GGGGGTAGCA  CTGTTGAAAG  TTGT                                    94
```

( 2 ) INFORMATION FOR SEQ ID NO:239:

( i ) SEQUENCE CHARACTERISTICS:
       ( A ) LENGTH: 29 amino acids
       ( B ) TYPE: amino acid
       ( C ) STRANDEDNESS:
       ( D ) TOPOLOGY: linear ( i i ) MOLECULE TYPE: peptide ( x i ) SEQUENCE DESCRIPTION: SEQ ID NO:239:

```
 Gly  Gly  Xaa  Xaa  Xaa  Xaa  Tyr  Xaa  Cys  Arg  Ile  Gly  Pro  Ile  Thr  Trp
 1                   5                        10                       15

Val  Cys  Xaa  Xaa  Xaa  Xaa  Xaa  Xaa  Gly  Gly  Gly  Gly  Ser
                20                        25
```

( 2 ) INFORMATION FOR SEQ ID NO:240:

( i ) SEQUENCE CHARACTERISTICS:
       ( A ) LENGTH: 4 amino acids
       ( B ) TYPE: amino acid (C) STRANDEDNESS:
(D) TOPOLOGY: linear (ii) MOLECULE TYPE: peptide (xi) SEQUENCE DESCRIPTION: SEQ ID NO:240:

Gly Gly Gly Ser
1

(2) INFORMATION FOR SEQ ID NO:241:

(i) SEQUENCE CHARACTERISTICS:
(A) LENGTH: 26 amino acids
(B) TYPE: amino acid
(C) STRANDEDNESS:
(D) TOPOLOGY: linear (ii) MOLECULE TYPE: peptide (ix) FEATURE:
(A) NAME/KEY: Modified-site
(B) LOCATION: 5
(D) OTHER INFORMATION: /note= "Xaa = unsure amino acid"

(xi) SEQUENCE DESCRIPTION: SEQ ID NO:241:

Gly Gly Tyr Gln Xaa Phe Met Gly Pro Glu Thr Trp Val Cys Ala Pro
1               5                   10                  15

Glu Pro Arg Val Glu Arg Val Ser Gly Gly
            20                  25

(2) INFORMATION FOR SEQ ID NO:242:

(i) SEQUENCE CHARACTERISTICS:
(A) LENGTH: 26 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:242:

Gly Gly Tyr Leu Cys Arg Phe Gly Pro Glu Thr Trp Thr Cys Ala Pro
1               5                   10                  15

Glu Arg Ser Val Val Thr Gln Ser Gly Gly
            20                  25

(2) INFORMATION FOR SEQ ID NO:243:

(i) SEQUENCE CHARACTERISTICS:
(A) LENGTH: 22 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:243:

Leu Gly Arg Lys Tyr Ser Cys His Phe Gly Pro Val Thr Trp Val Cys
1               5                   10                  15

Gln Pro Ala Lys Lys Asp
            20

(2) INFORMATION FOR SEQ ID NO:244:

(i) SEQUENCE CHARACTERISTICS:
(A) LENGTH: 19 amino acids
(B) TYPE: amino acid
(C) STRANDEDNESS:
(D) TOPOLOGY: linear ( i i ) MOLECULE TYPE: peptide ( x i ) SEQUENCE DESCRIPTION: SEQ ID NO:244:

Gly Gly Thr Tyr Ser Cys Phe Gly Pro Leu Thr Trp Val Cys Lys Pro
1               5                   10                  15

Gln Gly Gly ( 2 ) INFORMATION FOR SEQ ID NO:245:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:245:

Thr Tyr Ser Cys His Phe Gly Pro Leu Thr Trp Val Cys Lys Pro Gln
1               5                   10                  15

Gly Gly ( 2 ) INFORMATION FOR SEQ ID NO:246:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:246:

Tyr Ser Cys His Phe Gly Pro Leu Thr Trp Val Cys
1               5                   10

( 2 ) INFORMATION FOR SEQ ID NO:247:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /product="OTHER"
            / note= "Xaa = para-nitro-phenylalanine"

( x i ) SEQUENCE DESCRIPTION: SEQ ID NO:247:

Gly Gly Thr Xaa Ser Cys His Phe Gly Pro Leu Thr Trp Val Cys Lys
1               5                   10                  15

Pro Gln Gly Gly
        20

( 2 ) INFORMATION FOR SEQ ID NO:248:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( i x ) FEATURE:
    ( A ) NAME/KEY: Modified-site
    ( B ) LOCATION: 4
    ( D ) OTHER INFORMATION: /product="OTHER"
        / note= "Xaa = para-amino-phenylalanine"

( x i ) SEQUENCE DESCRIPTION: SEQ ID NO:248:

```
Gly Gly Thr Xaa Ser Cys His Phe Gly Pro Leu Thr Trp Val Cys Lys
1               5                   10                  15
Pro Gln Gly Gly
            20
```

( 2 ) INFORMATION FOR SEQ ID NO:249:

( i ) SEQUENCE CHARACTERISTICS:
    ( A ) LENGTH: 20 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Modified-site
    ( B ) LOCATION: 4
    ( D ) OTHER INFORMATION: /product="OTHER"
        / note= "Xaa = para-fluoro-phenylalanine"

( x i ) SEQUENCE DESCRIPTION: SEQ ID NO:249:

```
Gly Gly Thr Xaa Ser Cys His Phe Gly Pro Leu Thr Trp Val Cys Lys
1               5                   10                  15
Pro Gln Gly Gly
            20
```

( 2 ) INFORMATION FOR SEQ ID NO:250:

( i ) SEQUENCE CHARACTERISTICS:
    ( A ) LENGTH: 20 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Modified-site
    ( B ) LOCATION: 4
    ( D ) OTHER INFORMATION: /product="OTHER"
        / note= "Xaa = 3,5-dibromo-tyrosine"

( x i ) SEQUENCE DESCRIPTION: SEQ ID NO:250:

```
Gly Gly Thr Xaa Ser Cys His Phe Gly Pro Leu Thr Trp Val Cys Lys
1               5                   10                  15
Pro Gln Gly Gly
            20
```

( 2 ) INFORMATION FOR SEQ ID NO:251:

( i ) SEQUENCE CHARACTERISTICS:
    ( A ) LENGTH: 20 amino acids
    ( B ) TYPE: amino acid
    ( C ) STRANDEDNESS:
    ( D ) TOPOLOGY: linear ( i i ) MOLECULE TYPE: peptide ( x i ) SEQUENCE DESCRIPTION: SEQ ID NO:251:

```
Gly Gly Thr Tyr Ser Cys His Phe Gly Pro Leu Thr Phe Val Cys Lys
1               5                   10                  15
```

```
Pro Gln Gly Gly
        20
```

(2) INFORMATION FOR SEQ ID NO:252:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Xaa = Arg, His, or Leu"

(ix) FEATURE:
        (A) NAME/KEY: Modified-site
        (B) LOCATION: 3
        (D) OTHER INFORMATION: /note= "Xaa = Met, Phe, or Ile"

(ix) FEATURE:
        (A) NAME/KEY: Modified-site
        (B) LOCATION: 6
        (D) OTHER INFORMATION: /note= "Xaa = any amino acid"

(ix) FEATURE:
        (A) NAME/KEY: Modified-site
        (B) LOCATION: 9
        (D) OTHER INFORMATION: /note= "Xaa = Asp, Glu, Ile, Leu,
            or Val"

(xi) SEQUENCE DESCRIPTION: SEQ ID NO:252:

```
Cys Xaa Xaa Gly Pro Xaa Thr Trp Xaa Cys
 1               5                   10
```

(2) INFORMATION FOR SEQ ID NO:253:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Xaa = any amino acid"

(ix) FEATURE:
        (A) NAME/KEY: Modified-site
        (B) LOCATION: 4
        (D) OTHER INFORMATION: /note= "Xaa = Arg, His, or Leu"

(ix) FEATURE:
        (A) NAME/KEY: Modified-site
        (B) LOCATION: 5
        (D) OTHER INFORMATION: /note= "Xaa = Met, Phe, or Ile"

(ix) FEATURE:
        (A) NAME/KEY: Modified-site
        (B) LOCATION: 8
        (D) OTHER INFORMATION: /note= "Xaa = any amino acid"

(ix) FEATURE:
        (A) NAME/KEY: Modified-site
        (B) LOCATION: 11
        (D) OTHER INFORMATION: /note= "Xaa = Asp, Glu, Ile, Leu,
            or Val"

(xi) SEQUENCE DESCRIPTION: SEQ ID NO:253:

```
Tyr Xaa Cys Xaa Xaa Gly Pro Xaa Thr Trp Xaa Cys
```

(2) INFORMATION FOR SEQ ID NO:254:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa = any amino acid"

(ix) FEATURE:
        (A) NAME/KEY: Modified-site
        (B) LOCATION: 3
        (D) OTHER INFORMATION: /note= "Xaa = any amino acid"

(ix) FEATURE:
        (A) NAME/KEY: Modified-site
        (B) LOCATION: 5
        (D) OTHER INFORMATION: /note= "Xaa = Arg, His, or Leu"

(ix) FEATURE:
        (A) NAME/KEY: Modified-site
        (B) LOCATION: 6
        (D) OTHER INFORMATION: /note= "Xaa = Met, Phe, or Ile"

(ix) FEATURE:
        (A) NAME/KEY: Modified-site
        (B) LOCATION: 9
        (D) OTHER INFORMATION: /note= "Xaa = any amino acid"

(ix) FEATURE:
        (A) NAME/KEY: Modified-site
        (B) LOCATION: 12
        (D) OTHER INFORMATION: /note= "Xaa = Asp, Glu, Ile, Leu, or Val"

(ix) FEATURE:
        (A) NAME/KEY: Modified-site
        (B) LOCATION: 14
        (D) OTHER INFORMATION: /note= "Xaa = any amino acid"

(ix) FEATURE:
        (A) NAME/KEY: Modified-site
        (B) LOCATION: 15
        (D) OTHER INFORMATION: /note= "Xaa = any amino acid"

(ix) FEATURE:
        (A) NAME/KEY: Modified-site
        (B) LOCATION: 16
        (D) OTHER INFORMATION: /note= "Xaa = any amino acid"

(xi) SEQUENCE DESCRIPTION: SEQ ID NO:254:

```
Xaa Tyr Xaa Cys Xaa Xaa Gly Pro Xaa Thr Trp Xaa Cys Xaa Xaa Xaa
 1               5                  10                 15
```

(2) INFORMATION FOR SEQ ID NO:255:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:255:

```
Xaa Xaa Xaa Xaa Xaa Xaa Xaa Xaa Xaa Xaa Tyr Xaa Cys Xaa Xaa Gly
 1               5                  10                 15
```

Pro Xaa Thr Trp Xaa Cys Gly Gly Gly Gly Ser
                 20                      25

(2) INFORMATION FOR SEQ ID NO:256:

(i) SEQUENCE CHARACTERISTICS:
      (A) LENGTH: 27 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:256:

Gly Gly Xaa Xaa Xaa Xaa Tyr Cys Xaa Xaa Gly Pro Xaa Thr Trp Xaa
   1               5                   10                  15
   Cys Xaa Xaa Xaa Xaa Xaa Gly Gly Gly Gly Ser
                20                  25

(2) INFORMATION FOR SEQ ID NO:257:

(i) SEQUENCE CHARACTERISTICS:
      (A) LENGTH: 29 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:257:

Gly Gly Tyr Xaa Cys Xaa Xaa Gly Pro Xaa Thr Trp Xaa Cys Xaa Xaa
   1               5                   10                  15
   Xaa Xaa Xaa Xaa Xaa Xaa Xaa Xaa Gly Gly Gly Gly Ser
                20                  25

(2) INFORMATION FOR SEQ ID NO:258:

(i) SEQUENCE CHARACTERISTICS:
      (A) LENGTH: 22 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:258:

Xaa Xaa Xaa Xaa Tyr Xaa Cys His Phe Gly Pro Leu Thr Trp Val Cys
   1               5                   10                  15
   Xaa Xaa Xaa Xaa Xaa Xaa
                20

(2) INFORMATION FOR SEQ ID NO:259:

(i) SEQUENCE CHARACTERISTICS:
      (A) LENGTH: 22 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:259:

Xaa Xaa Xaa Xaa Tyr Xaa Cys Xaa Xaa Gly Pro Glu Thr Trp Glu Cys
   1               5                   10                  15
   Xaa Xaa Xaa Xaa Xaa Xaa
                20

METHODS OF ADMINISTERING PEPTIDES THAT BIND TO THE ERYTHROPOIETIN RECEPTOR

This application is a continuation-in-part of Ser. No. 08/155,940, filed Nov. 19, 1993, now abandoned which is incorporated herein by reference.

FIELD OF THE INVENTION

The present invention provides, inter alia, peptides and compounds that bind and activate the erythropoietin receptor (EPO-R) or otherwise act as an EPO agonist. The invention has application in the fields of biochemistry and medicinal chemistry and particularly provides EPO agonists for use in the treatment of human disease.

BACKGROUND OF THE INVENTION

Erythropoietin (EPO) is a glycoprotein hormone with 165 amino acids, 4 glycosylation sites on amino-acid positions 24, 38, 83, and 126, and a molecular weight of about 34,000. It is initially produced as a precursor protein with a signal peptide of 23 amino acids. EPO can occur in three forms: α, β, and asialo. The α and β forms differ slightly in the carbohydrate components, but have the same potency, biological activity, and molecular weight. The asialo form is an α or β form with the terminal carbohydrate (sialic acid) removed. The DNA sequences encoding EPO have been reported. See, Lin (1987) U.S. Pat. No. 4,703,008, which is incorporated herein by reference.

EPO stimulates mitotic division and the differentiation of erythrocyte precursor cells and thus ensures the production of erythrocytes. It is produced in the kidney when hypoxic conditions prevail. During EPO-induced differentiation of erythrocyte precursor cells, there is induction of globin synthesis and increases in the synthesis of the heme complex and in the number of ferritin receptors. This makes it possible for the cell to take on more iron and synthesize functional hemoglobin. Hemoglobin in mature erythrocytes binds oxygen. Thus, the erythrocytes and the hemoglobin contained in them play a key part in supplying the body with oxygen. The complex processes which have been described are initiated by the interaction of EPO with an appropriate receptor on the cell surface of the erythrocyte precursor cells. See, e.g., Graber and Krantz (1978) Ann. Rev. Med. 29:51–66.

EPO is present in very low concentrations in plasma when the body is in a healthy state wherein tissues receive sufficient oxygenation from the existing number of erythrocytes. This normal low concentration is enough to stimulate replacement of red blood cells which are lost normally through aging.

The amount of EPO in the circulation is increased under conditions of hypoxia when oxygen transport by blood cells in the circulation is reduced. Hypoxia may be caused by loss of large amounts of blood through hemorrhage, destruction of red blood cells by over-exposure to radiation, reduction in oxygen intake due to high altitudes or prolonged unconsciousness, or various forms of anemia. In response to tissues undergoing hypoxic stress, EPO will increase red blood cell production by stimulation of proliferation of erythroid progenitor cells. When the number of red blood cells in circulation is greater than needed for normal tissue oxygen requirements, EPO in circulation is decreased.

Because EPO is essential in the process of red blood cell formation, the hormone has potentially useful applications in both the diagnosis and the treatment of blood disorders characterized by low or defective red blood cell production. Recent studies have provided a basis for the projection of efficacy of EPO therapy in a variety of disease states, disorders, and states of hematologic irregularity, including: beta-thalassemia (see, Vedovato et al. (1984) Acta. Haematol. 71:211–213); cystic fibrosis (see, Vichinsky et al. (1984) J. Pediatric 105:15–21; pregnancy and menstrual disorders (see, Cotes et al. (193) Brit. J. Ostet. Gyneacol. 90:304–311; early anemia of prematurity (see, Haga et al. (1983) Acta Pediatr. Scand. 72; 827–831); spinal cord injury (see, Claus-Walker et al. (1984) Arch. Phys. Med. Rehabil. 65:370–374); space flight (see, Dunn et al. (1984) Eur. J. Appl. Physiol. 52:178–182); acute blood loss (see, Miller et al. (1982) Brit. J. Haematol. 52:545–590); aging (see, Udupa et al. (1984) J. Lab. Clin. Med. 103:574–580 and 581–588 and Lipschitz et al. (1983) Blood 63:502–509; various neoplastic disease states accompanied by abnormal erythropoiesis (see, Dainiak et al. (1983) Cancer 5:1101–1106 and Schwartz et al. (1983) Otolaryngol. 109:269–272); and renal insufficiency (see, Eschbach et al. (1987) N. Eng. J. Med. 316:73–78).

Purified, homogeneous EPO has been characterized. See, Hewick U.S. Pat. No. 4,677,195. A DNA sequence encoding EPO was purified, cloned and expressed to produce synthetic polypeptides with the same biochemical and immunological properties. A recombinant EPO molecule with oligosaccharides identical to those on the natural material has also been produced. See, Sasaki et al. (1987) J. Biol. Chem. 262:12059–12076.

Despite the availability of purified recombinant EPO, little is known concerning the mechanism of EPO-induced erythroblast proliferation and differentiation. The specific interaction of EPO with progenitors of immature red blood cells, platelets, and megakaryocytes remains to be characterized. This is due, at least in part, to the small number of surface EPO receptor molecules on normal erythroblasts and on the erythroleukemia cell line. See, Krantz and Goldwasser (1984) Proc. Natl. Acad. Sci. USA 81:7574–7578; Branch et al. (1987) Blood 69:1782–1785; Mayeux et al. (1987) FEBS Letters 211:229–233; Mufson and Gesner (1987) Blood 69:1485–1490; Sakaguchi et al. (1987) Biochem. Biophys. Res. Commun. 146:7–12; Sawyer et al. (1987) Proc. Natl. Acad. Sci. USA 84:3690–3694; Sawyer et al. (1987) J. Biol. Chem. 262:5554–5562; and Todokoro et al. (1988) Proc. Natl. Acad. Sci. USA 84:4126–4130.

Cross-linked complexes between radioiodinated EPO and cell surface proteins suggest that the cell surface proteins comprise two polypeptides having approximate molecular weights of 85,000 daltons and 100,000 daltons, respectively. More recently, the two cross-linked complexes have been subjected to V8 protease digestion and have been found to have identical peptide fragments, suggesting that the two EPO-binding polypeptides may be products of the same or very similar genes. See, Sawyer et al. (1988) supra. Most cell surface binding studies, however, have revealed a single class of binding sites, averaging 300 to 600 per cell surface, with a Kd of approximately 800 pM (picomolar). See, Sawyer et al. (1987) Proc. Natl. Acad. Sci. USA 84:3690–3694. However, EPO-responsive splenic erythroblasts, prepared from mice injected with the anemic strain (FVA) of the Friend leukemia virus, demonstrate a high and a low affinity binding site with dissociation constants of 100 pM and 800 pM, respectively. See, Sawyer et aL (1987) J. Biol. Chem. 262:5554–5562 and Landschulz (1989) Blood 73:1476–1478. The DNA sequences and encoded peptide sequences for murine and human EPO receptor proteins have been described. See, D'Andrea et al. PCT Patent Publication No. WO 90/08822 (published 1990).

The availability of cloned genes for the EPO-R facilitates the search for agonists and antagonists of this important receptor. The availability of the recombinant receptor protein allows the study of receptor-ligand interaction in a variety of random and semi-random peptide diversity generation systems. These systems include the "peptides on plasmids" system described in U.S. patent application Ser. No. 778,233, filed Oct. 16, 1991, issued as U.S. Pat. No. 5,270,170, the "peptides on phage" system described in U.S. patent application Ser. No. 718,577, filed Jun. 20, 1991, issued as U.S. Pat. No. 5,432,018, and in Cwirla et al., August 1990, *Proc. Natl. Acad. Sci. USA* 87:6378–6382, the "encoded synthetic library" (ESL) system described in U.S. patent application Ser. No. 946,239, filed Sep. 16, 1992, pending which is a continuation-in-part application of Ser. No. 762,522, filed Sep. 18, 1991, now abandoned, and the "very large scale immobilized polymer synthesis" system described in U.S. patent application Ser. No. 492,462, filed Mar. 7, 1990, now U.S. Pat. No. 5,143,854; PCT patent publication No. 90/15070, published Dec. 13, 1990; U.S. patent application Ser. No. 624,120, filed Dec. 6, 1990, now abandoned; Fodor et al., 15 Feb., 1991, *Science* 251:767–773; Dower and Fodor, 1991, *Ann. Rep. Med. Chem.* 26 :271–180; and U.S. patent application Ser. No. 805,727, filed Dec. 6, 1991 now U.S. Pat. No. 5,424,186; each of the foregoing patent applications and publications is incorporated herein by reference.

There remains a need, however, for compounds that bind to or otherwise interact with the EPO-R, both for studies of the important biological activities mediated by this receptor and for treatment of disease. The present invention provides such compounds.

SUMMARY OF THE INVENTION

In one embodiment, the invention provides peptides that bind to and activate the EPO-R or otherwise behave as EPO agonists. These peptides are 10 to 40 or more amino acid residues in length, preferably 14 to 20 amino acid residues in length, and comprise a core sequence of amino acids $X_3X_4X_5GPX_6TWX_7X_8$ (SEQ ID NO:1), where each amino acid is indicated by standard one letter abbreviation; $X_3$ can be C, A, α-amino-γ-bromobutyric acid, or Hoc, where Hoc is homocysteine; $X_4$ can be R, H, L, or W; $X_5$ can be M, F, or I; $X_6$ is independently selected from any one of the 20 genetically coded L-amino acids or the stereoisomeric D-amino acids; $X_7$ can be D, E, I, L, or V; and $X_8$ can be C, A, α-amino-γ-bromobutyric acid, or Hoc, where Hoc is homocysteine, provided that either $X_3$ or $X_8$ is C or Hoc. Preferably, the peptide will comprise a core sequence $YX_2X_3X_4X_5GPX_6TWX_7X_8$ (SEQ ID NO:2), where each amino acid is indicated by standard one letter abbreviation; each $X_2$ and $X_6$ is independently selected from any one of the 20 genetically coded L-amino acids; $X_3$ can be C, A, α-amino-γ-bromobutyric acid, or Hoc, where Hoc is homocysteine; $X_4$ can be R, H, L, or W; $X_5$ can be M, F, or I; $X_7$ can be D, E, I, L, or V; and $X_8$ can be C, A, α-amino-γ-bromobutyric acid, or Hoc, where Hoc is homocysteine, provided that either $X_3$ or $X_8$ is C or Hoc.

More preferably, the peptide will comprise a core sequence of amino acids $X_1YX_2X_3X_4X_5GPX_6TWX_7X_8X_9X_{10}X_{11}$ (SEQ ID NO:3), where each amino acid is indicated by standard one letter abbreviation; each $X_1, X_2, X_6, X_9, X_{10}$, and $X_{11}$ is independently selected from any one of the 20 genetically coded L-amino acids; $X_3$ can be C, A, α-amino-γ-bromobutyric acid, or Hoc, where Hoc is homocysteine; $X_4$ can be R, H, L, or W; $X_5$ can be M, F, or I; $X_7$ can be D, E, I, L, or V; and $X_8$ can be C, A, α-amino-γ-bromobutyric acid, or Hoc, where Hoc is homocysteine, provided that either $X_3$ or $X_8$ is C or Hoc.

In a more preferred embodiment, both $X_3$ and $X_8$ will be C and, thus, the peptide will comprise a core sequence of amino acids $X_1YX_2CX_4X_5GPX_6TWX_7CX_9X_{10}X_{11}$ (SEQ ID NO:4). More preferably, the peptide will comprise a core sequence of amino acids $X_1YX_2CX_4X_5GPX_6TWX_7CX_9X_{10}X_{11}$ (SEQ ID NO:5), where $X_4$ can be R or H; $X_5$ can be F or M; $X_6$ can be I, L, T, M, or V; $X_7$ is D or V; $X_9$ can be G, K, L, Q, R, S, or T; and $X_{10}$ can be A, G, P, R, or Y. In a most preferred embodiment, the peptide will comprise a core sequence of amino acids $X_1YX_2CX_4X_5GPX_6TWX_7CX_9X_{10}X_{11}$ (SEQ ID NO:6), where $X_1$ can be D, E, L, N, S, T, or V; $X_2$ can be A, H, K, L, M, S, or T; $X_4$ is R or H; $X_9$ can be K, R, S, or T; and $X_{10}$ is P. Particularly preferred peptides include but are not limited to, the following:
GGLYLCRFGPVTWDCGYKGG (SEQ ID NO:7);
GGTYSCHFGPLTWVCKPQGG (SEQ ID NO:8);
GGDYHCRMGPLTWVCKPLGG (SEQ ID NO:9);
VGNYMCHFGPITWVCRPGGG (SEQ ID NO:10);
GGVYACRMGPITWVCSPLGG (SEQ ID NO:11);
VGNYMAHMGPITWVCRPGG (SEQ ID NO:12);
GGTYSCHFGPLTWVCKPQ (SEQ ID NO:13);
GGLYACHMGPMTWVCQPLRG (SEQ ID NO:14);
TIAQYICYMGPETWECRPSPKA (SEQ ID NO:15);
YSCHFGPLTWVCK (SEQ ID NO:16); and
YCHFGPLTWVC (SEQ ID:17).

According to some embodiments of this invention, two or more, and preferably between two to six amino acid residues, independently selected from any of the 20 genetically coded L-amino acids or the stereoisomeric D-amino acids, will be coupled to either or both ends of the core sequences described above. For example, the sequence GG will often be appended to either or both termini of the core sequences for ease in synthesis of the peptides. The present invention also provides conjugates of these peptides and derivatives and peptidomimetics of the peptides that retain the property of EPO-R binding.

The present invention also provides methods for treating disease involving a deficiency of EPO utilizing the novel compounds of the invention. The present invention further provides pharmaceutical compositions comprising one or more compounds of the invention and a physiologically acceptable carrier.

BRIEF DESCRIPTION OF THE DRAWINGS

FIGS. 2-1 and 2-2 provide the sequences of representative peptides of this invention.

FIG. 3 illustrates a new phagemid mutagenesis library constructed using the pVIII display system. In this library, the tyrosine, glycine-proline and threonine-tryptophan residues (underlined) were fixed, as well at the two cysteines. Other positions between the cysteine residues (shown in outline italic typeface present in the original AF11154 hit peptide) were mutated by oligo construction such that each amino acid residue could change to any other at a frequency of 50%. "X" denotes a random amino acid position.

FIGS. 4A–4C illustrate pIII and pVIII phagemid mutagenesis libraries currently under construction and screening. Amino acid residues in bold face are fixed, the remainder (indicated by NNK) are randomized. 4A (ON3007) and 4C (ON3017) are designed to investigate the contribution of extra flanking regions N-terminal and C-terminal, respectively, to the core sequence (tyrosine to the second cysteine). 4B (ON3016) is based on peptide Y-CHFGPLTWVC (SEQ ID NO:17), where the tyrosine residue is placed directly next to the first cysteine. This library adds additional random residues on both sides of the core sequence.

FIG. 5 illustrates a mutagenesis library, based on GGTYSCHFGPLTWVCKPQGG (SEQ ID NO:8), constructed and screened using a new Lac-I display vector ("Headpiece Dimer"). Amino acid residues denoted X are random (NNK), those underlined are lightly mutated (91:3:3:3/91:3:3:3/K), whereas those in outline are mutated more heavily (70:10:10/70:10:10/K).

FIG. 6 illustrates a mutagenesis library, based on TIAQYICYMGPETWECRPSPKA (SEQ ID NO:15), constructed and screened using a new Lac-I display vector ("Headpiece Dimer"). Amino acid residues denoted X are random (NNK), those in outline were fixed, and the two glutamic acid residues were lightly mutated (91:3:3:3/91:3:3:3/K).

FIG. 7 is a graphical depiction of the results of the FDCP-1/hEPO-R bioassay for selected peptides of the invention with:

● designating the results for GGCRIGPITWVCGG (SEQ ID NO:19);

○ designating the results for GGLYLCRFGPVTWDCGYKGG (SEQ ID NO:7);

■ designating the results for GGTYSCHFGPLTWVCKPQGG (SEQ ID NO:8);

▲ designating the results for GGDYHCRMGPLTWVCKPLGG (SEQ ID NO:9);

▼ designating the results for VGNYMCHFGPITWVCRPGGG (SEQ ID NO:10);

▌ designating the results for GGVYACRMGPITWVCSPLGG (SEQ ID NO:11);

+ designating the results for VGNYMAHMGPITWVCRPGG (SEQ ID NO:12); and

* designating the results for EPO.

Figure 8:
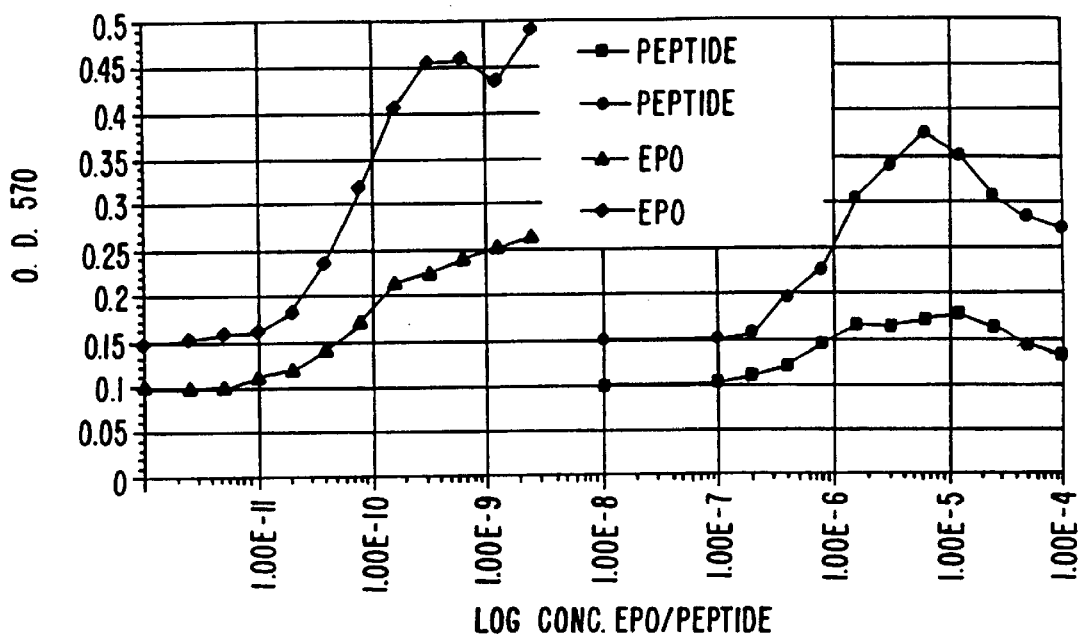

FIG. 8 is a graphical depiction of the results of the TF-1 bioassay for EPO (▲ and ♦ designate the results for the assay using EPO and 10,000 or 20,000 cells per well, respectively); and for the peptide VGNYMCHFGPITWVCRPGGG (SEQ ID NO:10) (■ and ● designate the results for the assay using the peptide and 10,000 or 20,000 cells per well, respectively).

Figure 9A:
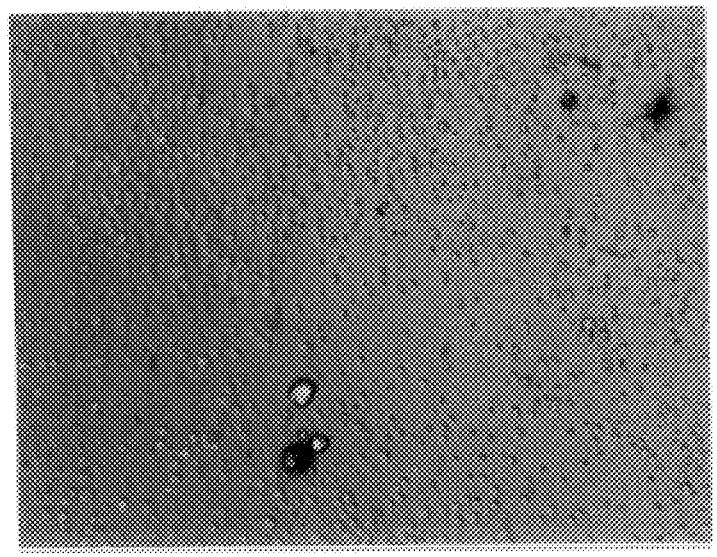

FIGS. 9A (control), 9B (treated with 500 pM EPO) and 9C (treated with 25 mm GGDYHCRMGPLTWVCKPLGG (SEQ ID NO:9)) are photographs depicting the results of a MTT proliferation assay on representative populations of spleen cells of phenylhydrazine treated mice at 20033 magnification.

Figure 10:
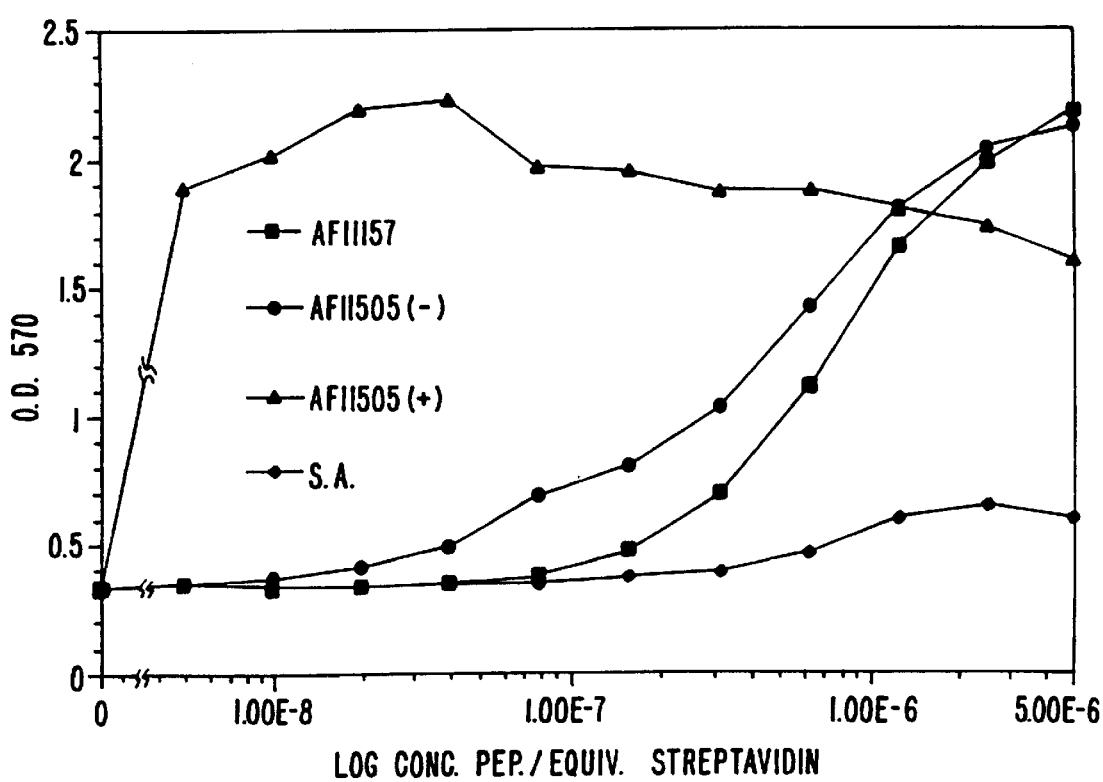

FIG. 10 is a graphical depiction of the results of the FDCP-1/hEPOR bioassay showing increased potency of the biotinylated peptide (i.e., GGTYSCHFGPLTWVCKPQGGSSK (SEQ ID NO:20) (Ahx-biotin)), by oligomerization with streptavidin. Peptides GGTYSCHFGPLTWVCKPQGG (SEQ ID NO:8) and GGTYSCHFGPLTWVCKPQGGSSK (SEQ ID NO:20) (Ahx-biotin) exhibit approximately the same activity, but when the latter is precomplexed with streptavidin (i.e., GGTYSCHFGPLTWVCKPQGGSSK (SEQ ID NO:20) (Ahx-biotin)-streptavidin complex), it is far more potent. In this assay, little reduction in activity is seen at the lowest concentration (5 nM with respect to peptide in the complex). Streptavidin, alone, has marginal activity at high concentrations.

Figure 11:
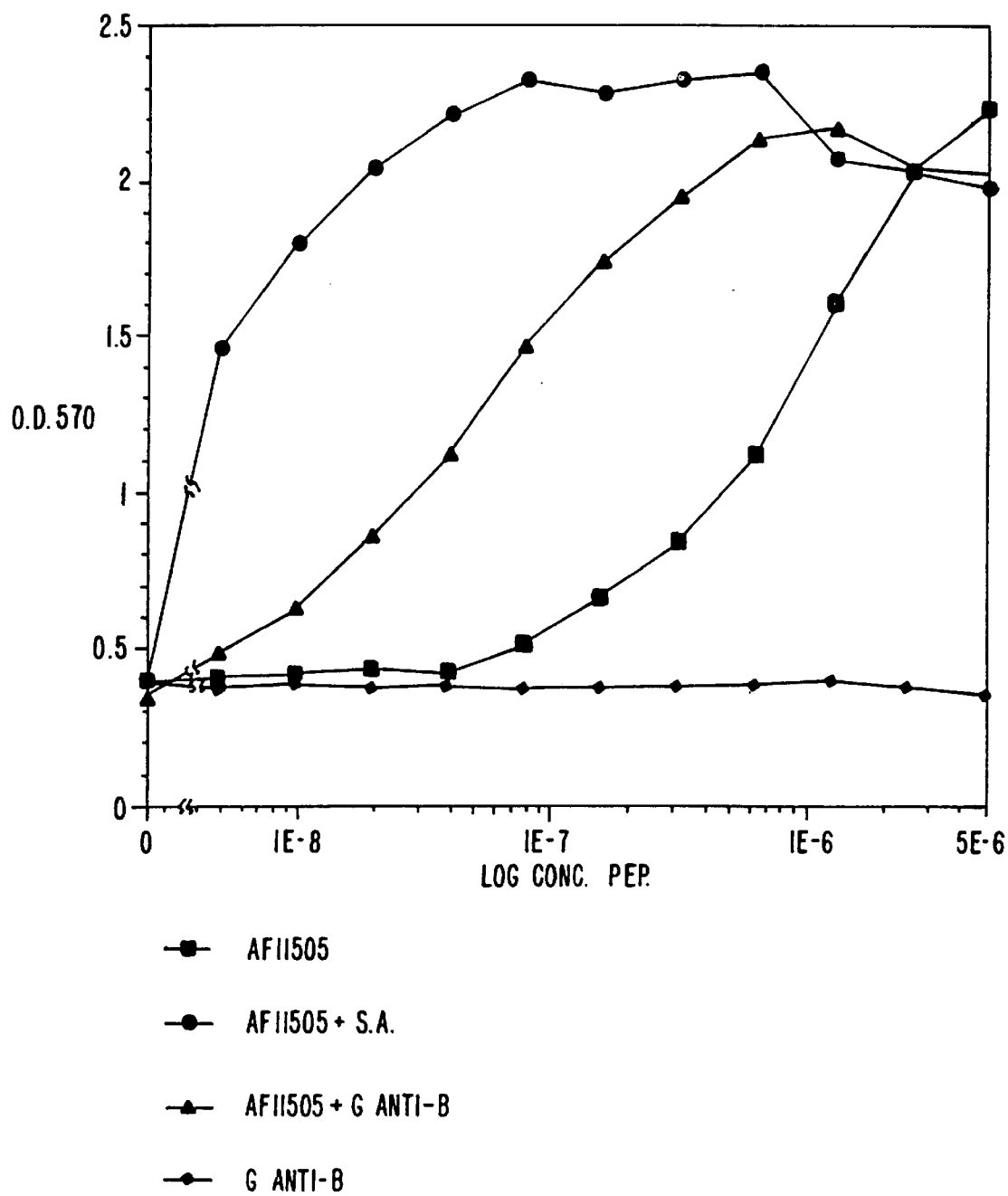

FIG. 11 is a graphical depiction of the results of the FDCP-1/hEPOR bioassay showing polyclonal goat anti-biotin-mediated increase in potency of peptide AF11505. Pre-complexing GGTYSCHFGPLTWVCKPQGGSSK (SEQ ID NO:20) (Ahx-biotin) with goat anti-biotin antibodies (GGTYSCHFGPLTWVCKPQGGSSK (SEQ ID NO:20) +G anti-B) increases the potency of the peptide one log over the free peptide. The purified antibodies (G anti-B) have no stimulatory effect alone.

Figures 1, 12:
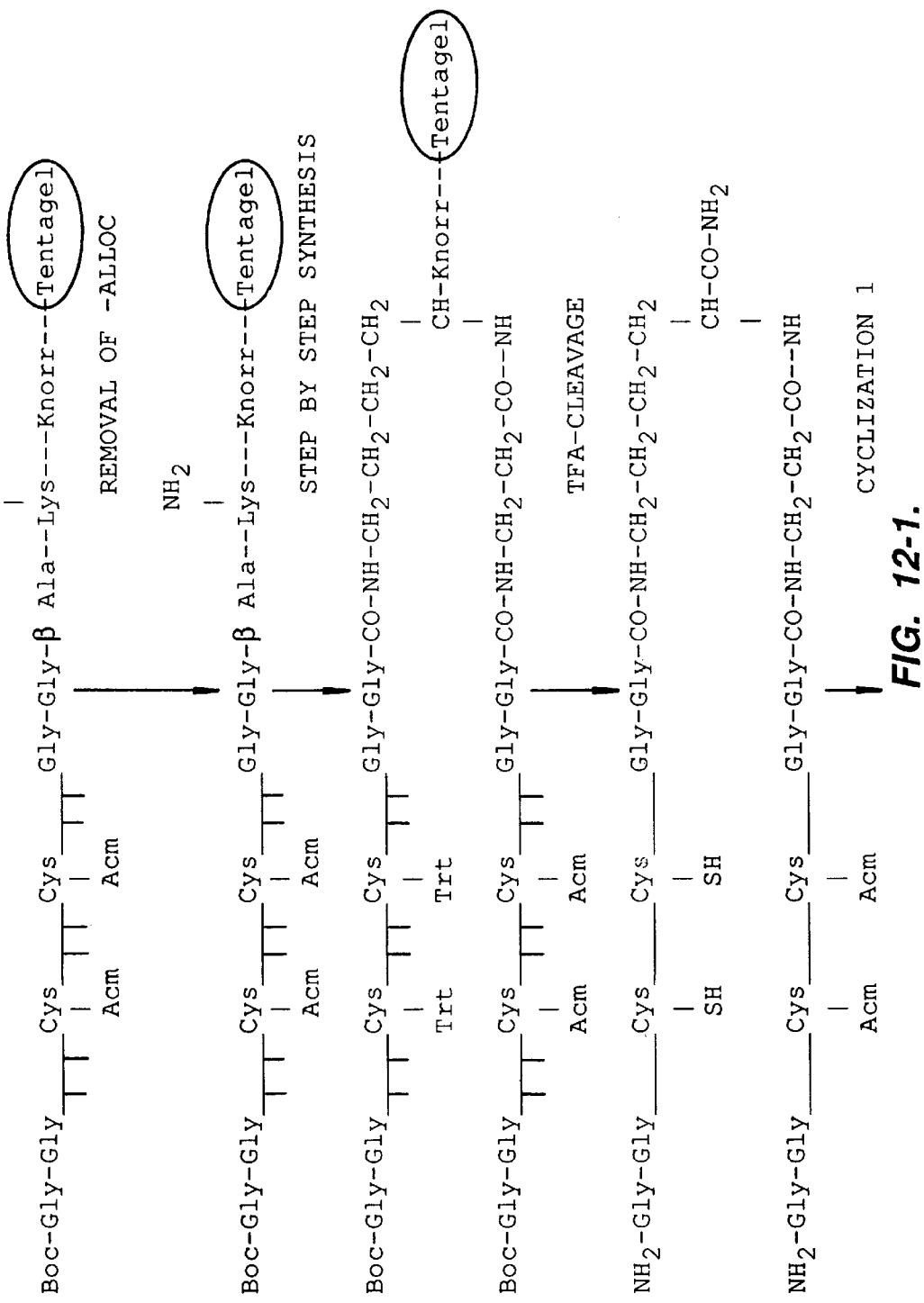
FIG. 1 provides the sequences of the mutagenesis oligomers employed in the procedures described herein N=any nucleotide; K=G or T.
Figures 2, 12:
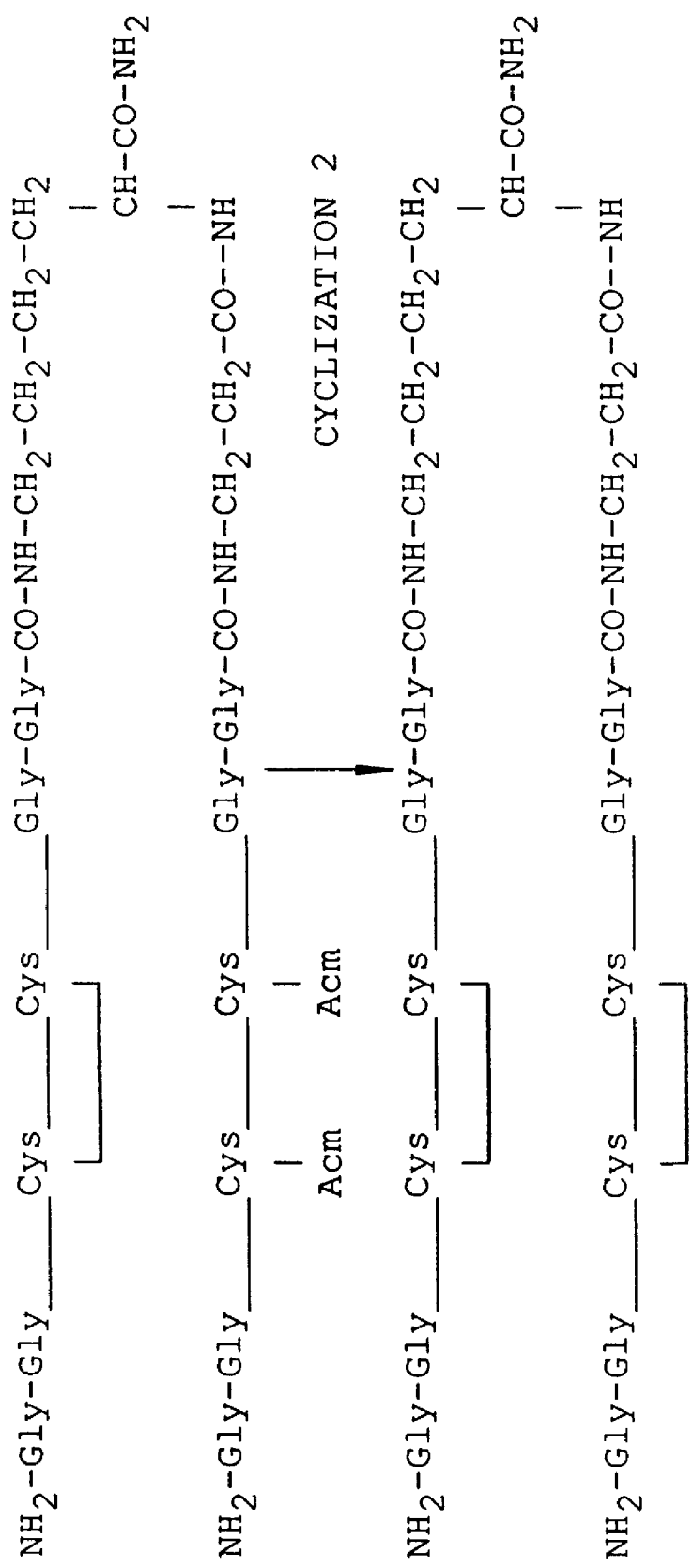

FIGS. 12-1 and 12-2 illustrate the synthetic scheme for the preparation of the dimeric peptide analog of GGTYSCHFGPLTWVCKPQGG (SEQ ID NO:8).

Figure 13:
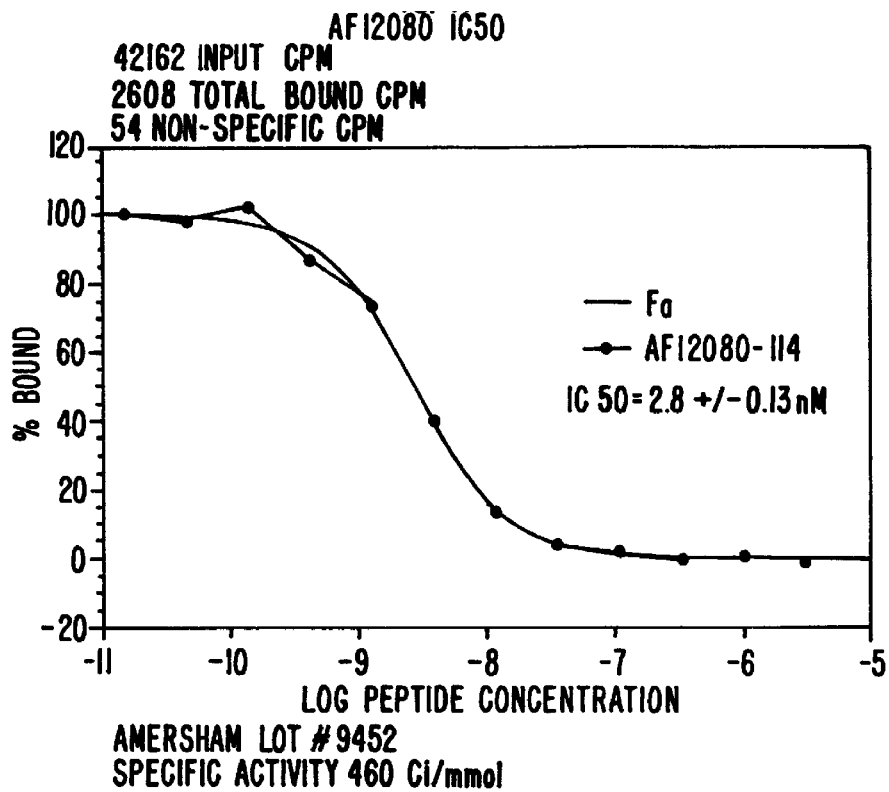

FIG. 13 illustrates the $IC_{50}$ plot of the dimeric peptide analog of GGTYSCHFGPLTWVCKPQGG (SEQ ID NO:8). Affinity was determined using a radioligand competition binding assay against PIG-tailed EPOR immobilized on mAB179.

Figure 14:
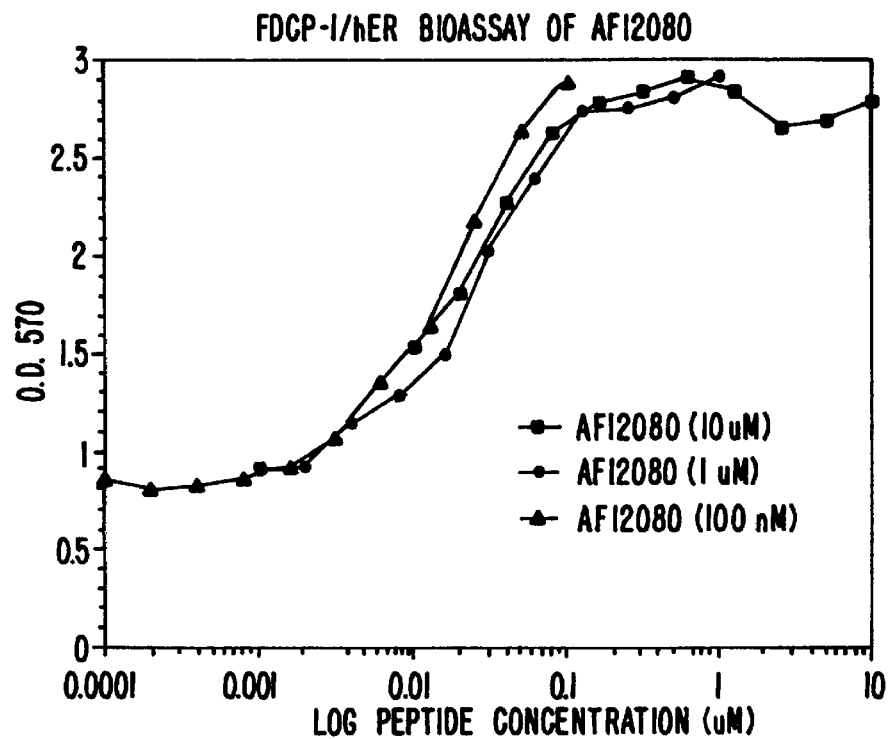

FIG. 14 illustrates the in vitro biological activity of the dimeric peptide analog of GGTYSCHFGPLTWVCKPQGG (SEQ ID NO:8) using the FDCP-1/hEPOR cell proliferation assay. The dimeric peptide has an $EC_{50}$ of approximately 20 nM, a 20-fold increase in potency over the parental peptide.

Figure 15:
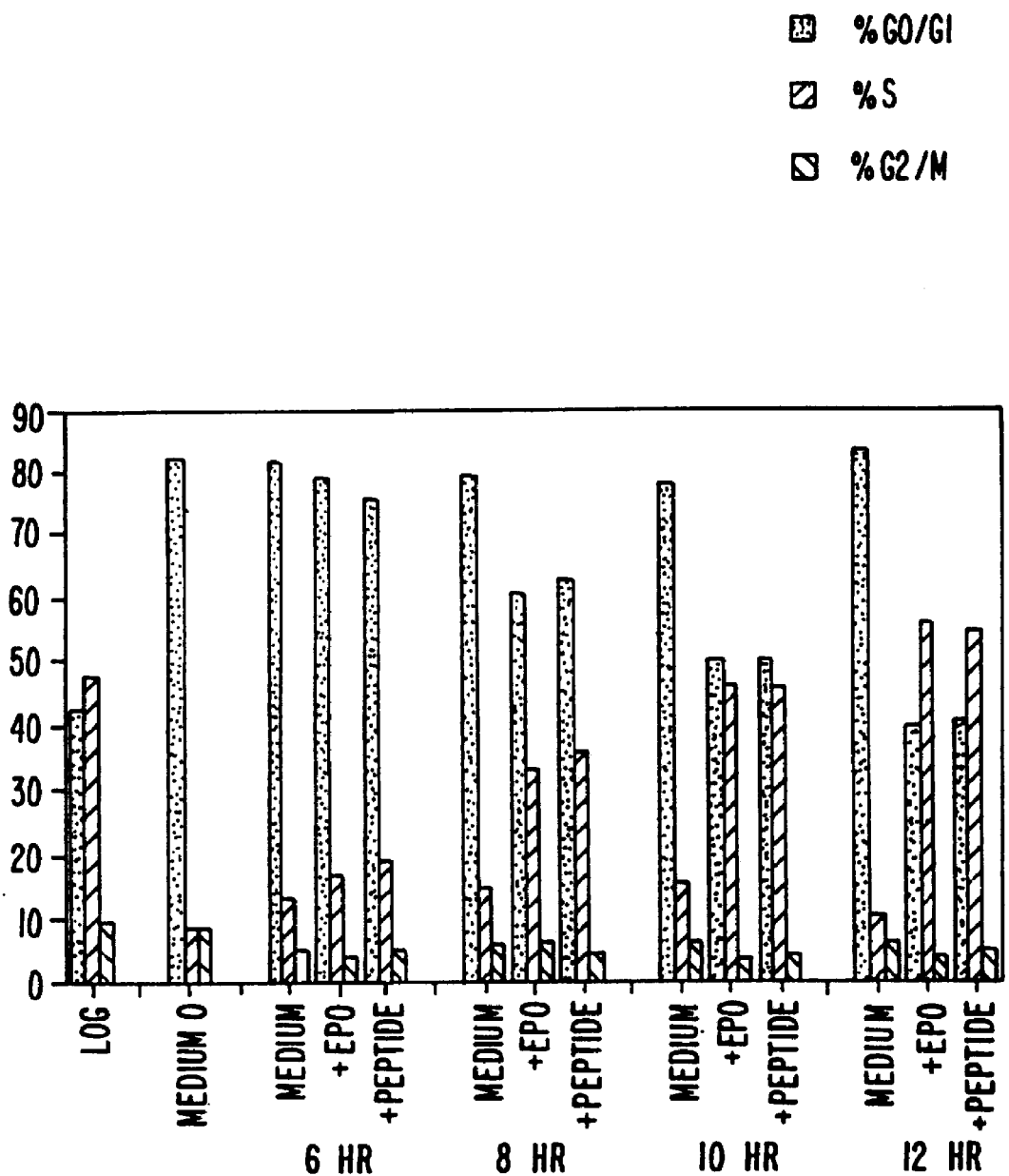

FIG. 15 illustrates the cell cycle progression of FDC-P1/ER.

Figure 16A:
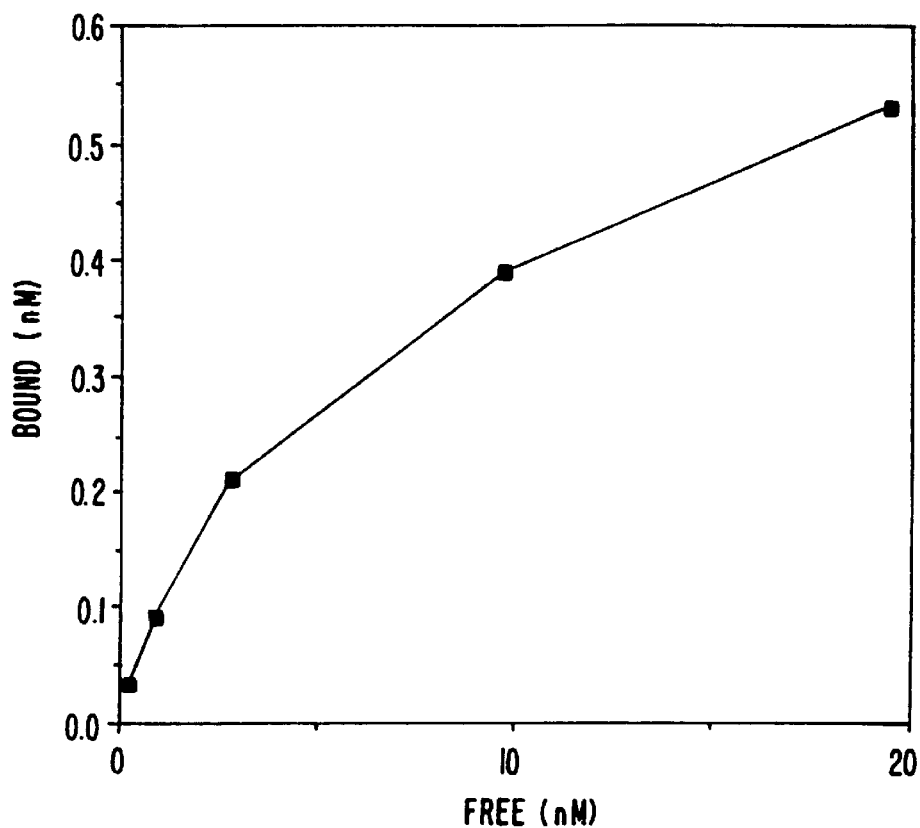
Figure 16B:
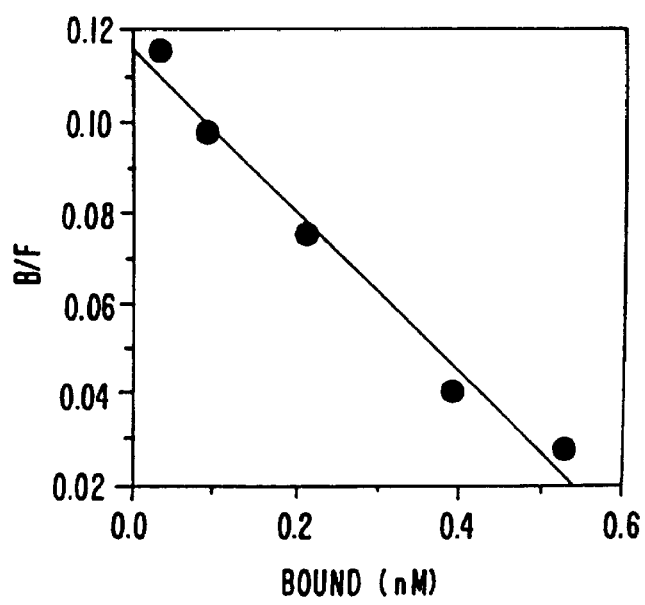

FIGS. 16A and 16B illustrate the equilibrium binding analysis of the specific association of $[^{125}I]$EPO with EBP immobilized on agarose beads and indicates a Kd of 5 nM±2 based on a linear transformation (Scatchard) of the binding isotherm.

Figure 17A:
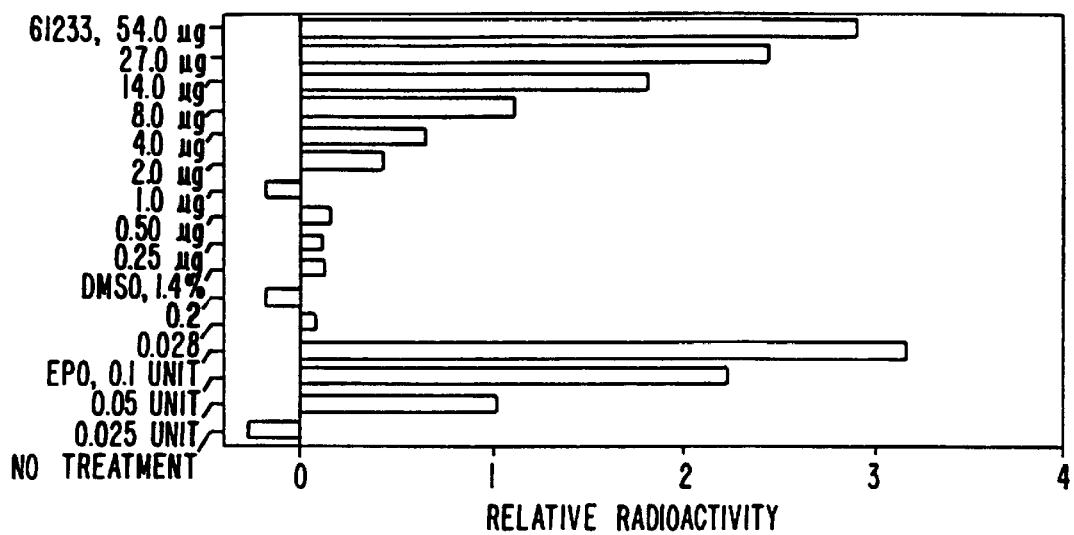
Figure 17B:
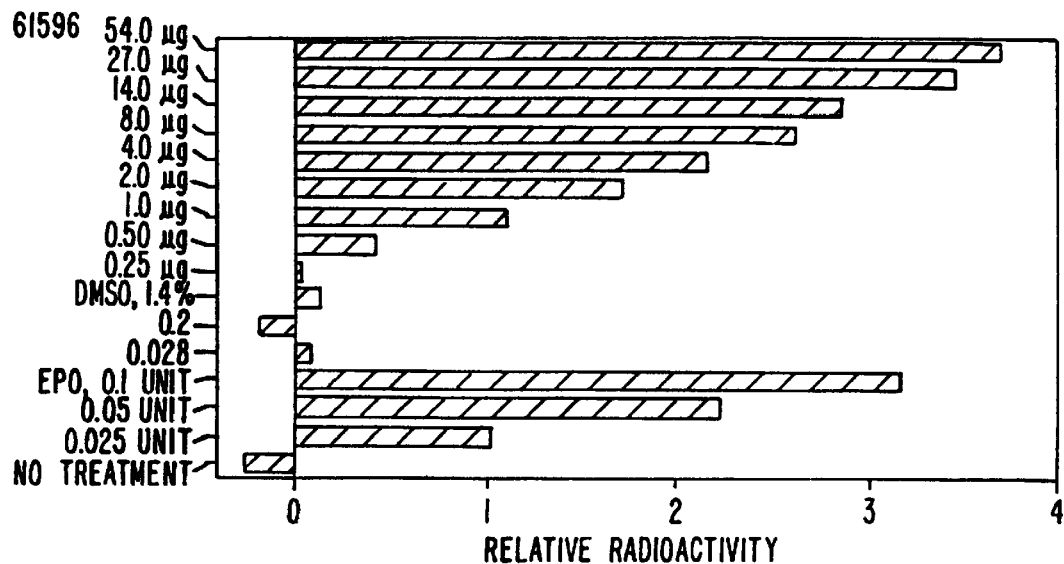
Figure 17C:
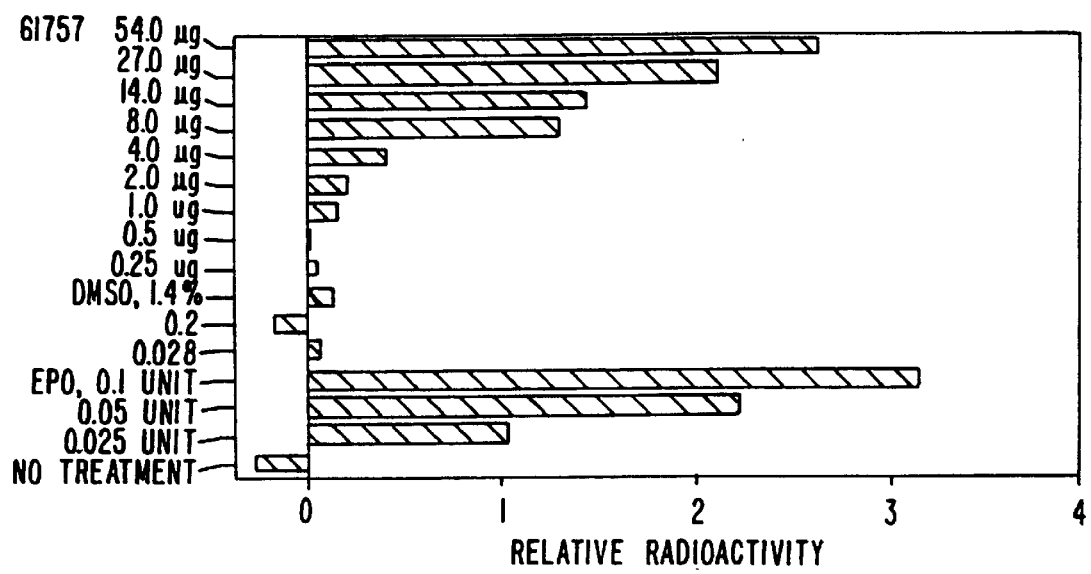

FIGS. 17A, 17B and 17C illustrate the results of the polycythemic exhypoxic mouse bioassay using peptides GGTYSCHFGPLTWVCKPQGG (SEQ ID NO:8), GTYSCHFGPLTWVCKPQ (SEQ ID NO:13) and LGRKYSCHFGPLTWVCQPAKKD(SEQ ID NO:21), respectively.

Figure 18A:
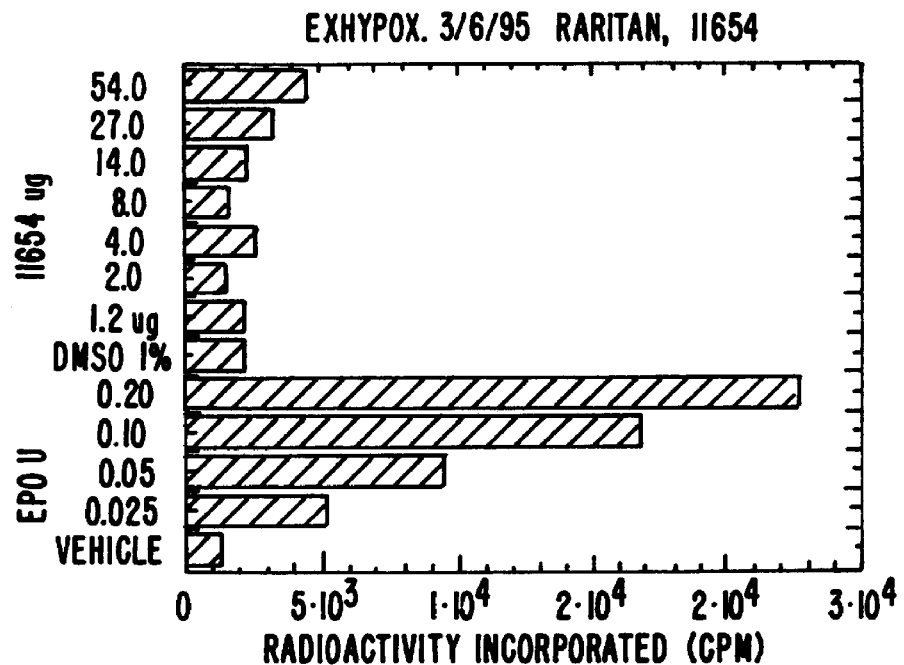
Figure 18B:
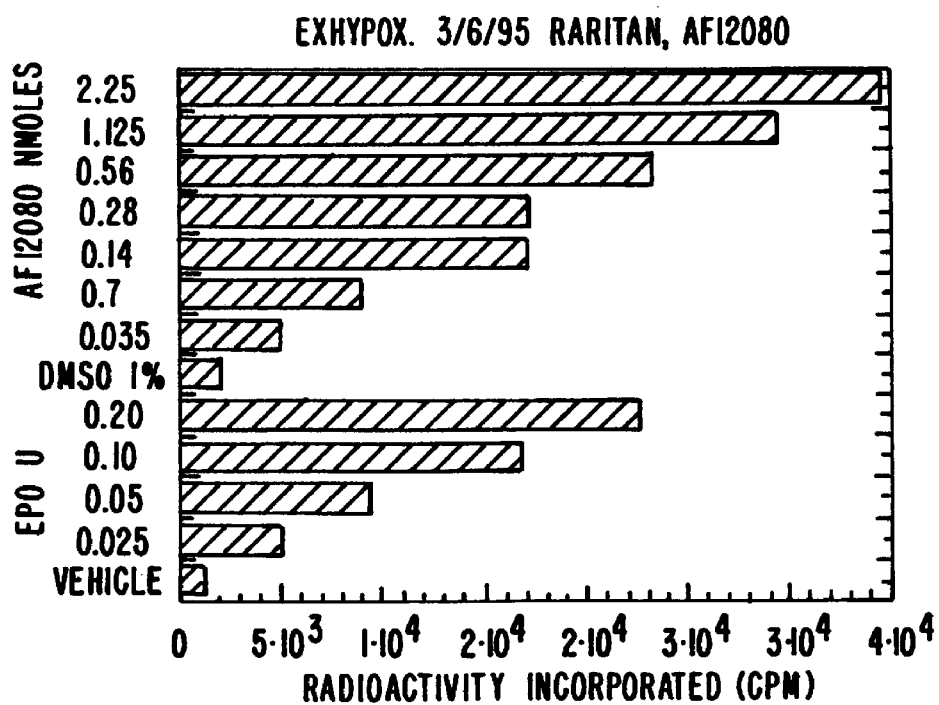

FIGS. 18A and 18B illustrate the results of the polycythemic exhypoxic mouse bioassay using peptides TIAQYICYMGPETWECRPSPKA (SEQ ID NO:15) and a dimeric peptide analog of GGTYSCHFGPLTWVCKPQGG (SEQ ID NO:8) containing two disulfide bonds (AF12080), respectively.

Figure 19A:
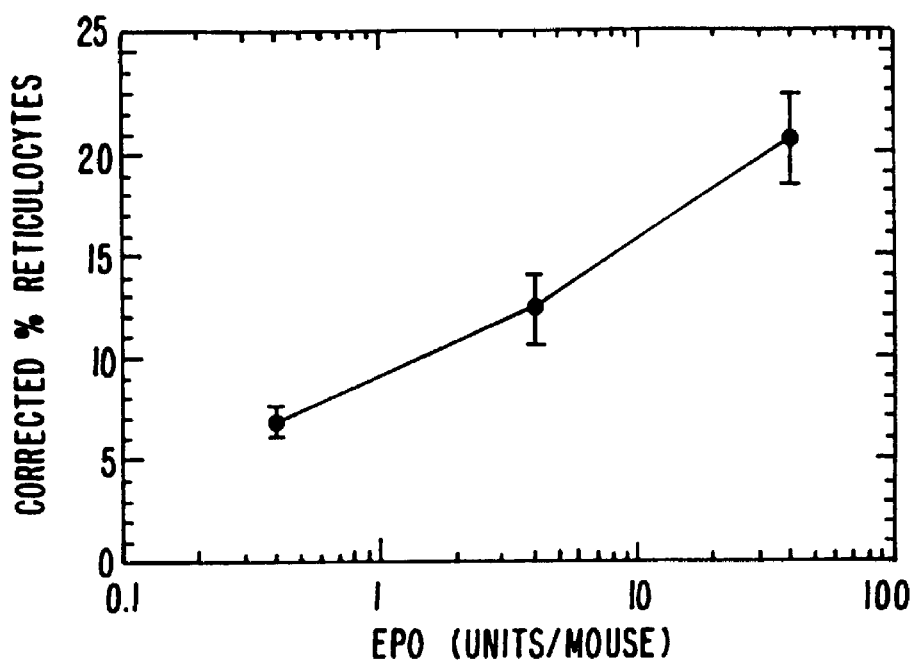
Figure 19B:
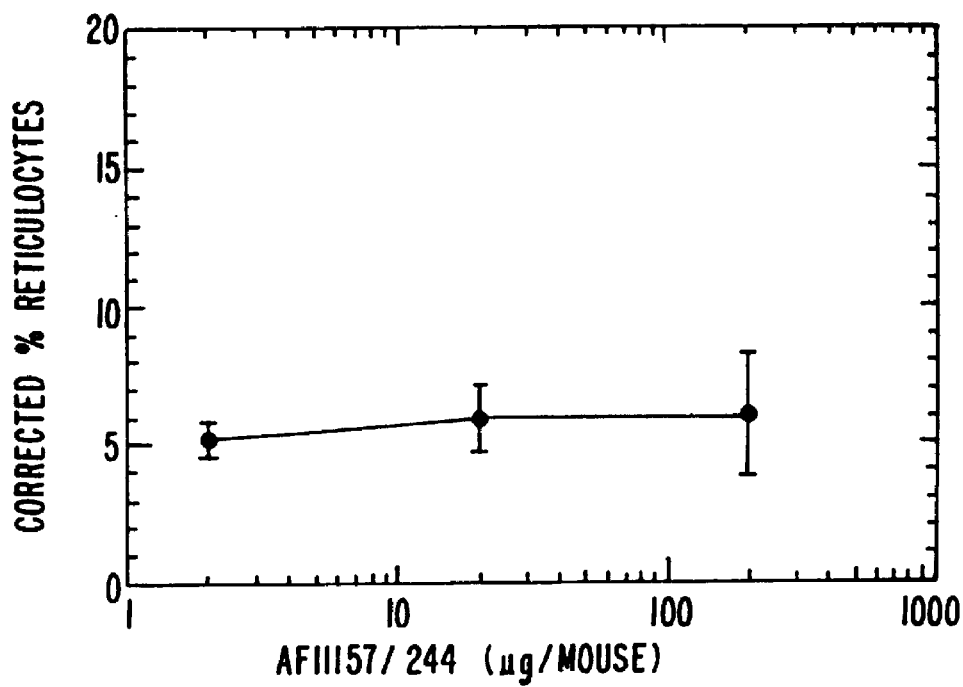

FIGS. 19A and 19B illustrate the results of the reticulocyte assay using EPO and GGTYSCHFGPLTWVCKPQGG (SEQ ID NO:8), respectively. For both dose groups, n=10 animals. EPO: 0.4, 4.0, 40.0 Units/mouse, total dose vehicle control; GGTYSCHFGPLTWVCKPQGG (SEQ ID NO:8): 2.0, 20.0, 200.0 μg/mouse, total dose vehicle control+ DMSO (1–2%) 200 μg/mouse=10 mg/kg. Rational: in vitro proliferation assay data suggests: 2 μg of GGTYSCHFGPLTWVCKPQGG (SEQ ID NO:8)=0.4 Units of EPO.

Figure 20A:
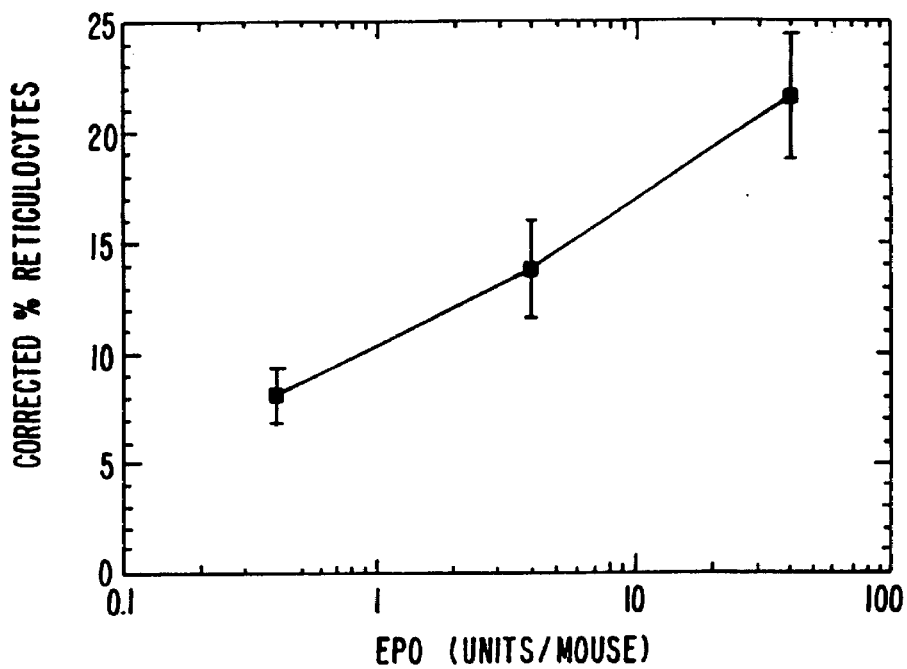
Figure 20B:
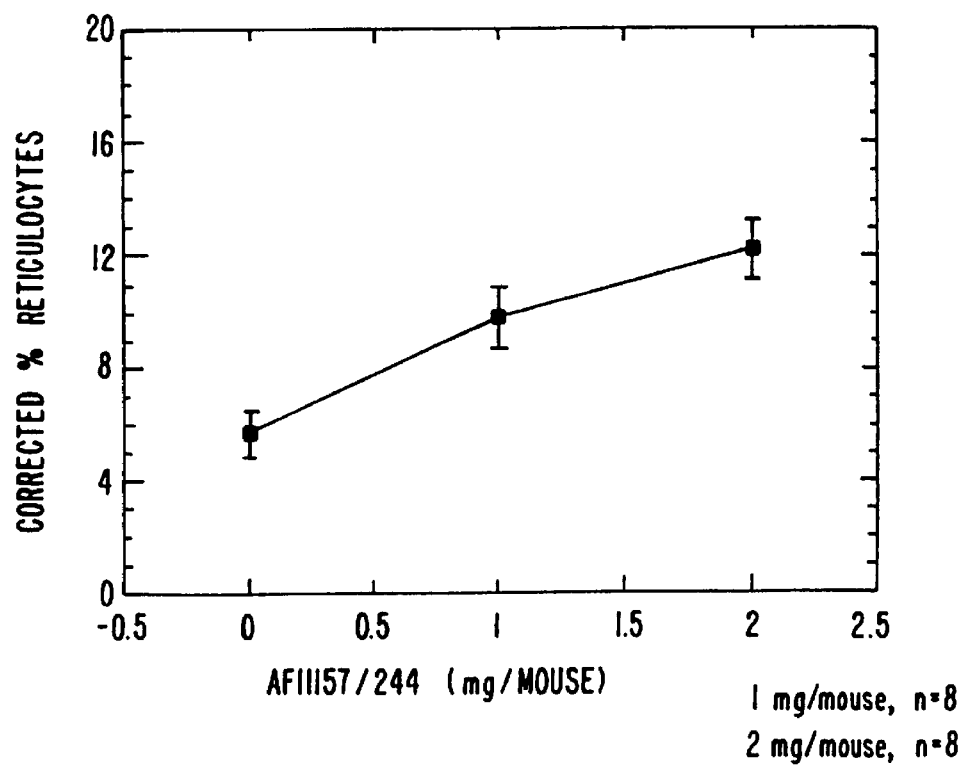

FIGS. 20A and 20B illustrate the results of the reticulocyte assay using EPO and GGTYSCHFGPLTWVCKPQGG (SEQ ID NO:8), respectively. For both dose groups, n=10 animals. EPO: 0.4, 4.0, 40.0 units/mouse, total dose; GGTYSCHFGPLTWVCKPQGG (SEQ ID NO:8): increase dose to 1 mg/mouse, total dose=50 mg/kg and to 2 mg/mouse, total dose=mg/kg.

DETAILED DESCRIPTION OF THE INVENTION AND PREFERRED EMBODIMENT

The following terms are intended to have the following general meanings:

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

Stereoisomers (e.g., D-amino acids) of the twenty conventional amino acids, unnatural amino acids such as a,a-disubstituted amino acids, N-alkyl amino acids, lactic acid, and other unconventional amino acids may also be suitable components for compounds of the present invention. Examples of unconventional amino acids include: 4-hydroxyproline, O-phosphoserine, N-acetylserine, N-formylmethionine, 3-methylhistidine, 5-hydroxylysine, and other similar amino acids and imino acids (e.g., 4-hydroxyproline).

"Agonist" refers to a biologically active ligand which binds to its omplementary biologically active receptor and activates the latter either to cause a biological response in the receptor, or to enhance preexisting biological activity of the receptor.

"Host Cell" refers to a eukaryotic or procaryotic cell or group of cells that can be or has been transformed by a recombinant DNA vector. For purposes of the present invention, procaryotic host cells are preferred.

"Peptide" or "polypeptide" refers to a polymer in which the monomers are alpha amino acids joined together through amide bonds. Peptides are two or often more amino acid monomers long.

"Pharmaceutically acceptable salts" refers to the non-toxic alkali metal, alkaline earth metal, and ammonium salts commonly used in the pharmaceutical industry including the sodium, potassium, lithium, calcium, magnesium, barium, ammonium and protamine zinc salts, which are prepared by methods well known in the art. The term also includes non-toxic acid addition salts, which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate and the like.

"Pharmaceutically or therapeutically effective dose or amount" refers to a dosage level sufficient to induce a desired biological result. That result can be alleviation of the signs, symptoms, or causes of a disease, or any other desired alteration of a biological system. Preferably, this dose or amount will be sufficient to stimulate the EPO-R and, thus, alleviate the symptoms associated with a deficiency of EPO, or a defective or low red blood population in vivo.

"Recombinant DNA Cloning or Expression Vector" refers to a DNA or RNA molecule that encodes a useful function and can be used to transform a host cell. For purposes of the present invention, a cloning vector typically serves primarily as an intermediate in the construction of an expression vector; the latter vector is used to transform or transfect a host cell so that the transformed host cell produces a protein or other product encoded by the vector. Such vectors are typically "plasmids," which for purposes of the present invention, are vectors that can be extrachromosomally maintained in a host cell, but can also be vectors that integrate into the genome of a host cell. Those of skill in the art may refer to "cloning vectors", as defined herein, as "vectors" and to "expression vectors," as defined herein, as "plasmids."

The present invention provides compounds that bind to and activate the EPO-R or otherwise behave as an EPO agonist. These compounds include "lead" peptide compounds, discovered with random peptide diversity generating systems, and "derivative" compounds constructed so as to have the same or similar molecular structure or shape as the lead compounds, but that differ from the lead compounds either with respect to susceptibility to hydrolysis or proteolysis and/or with respect to other biological properties, such as increased affinity for the receptor, increased in vitro activity or in vivo activity.

The random peptide diversity generating systems initially employed included the "peptides on phage" system discussed above. The random peptides were designed to be 8 amino acid residues in length, flanked by Cys residues at both termini (thus, 10 amino acid residues in total length). In these initial systems, the random peptides were presented as part of a fusion protein comprising the pVIII coat protein of a phage fd derivative (peptides on phage). The fusion proteins, along with the DNA encoding the fusion proteins, were "panned" on immobilized EPO-R. The panning process involved multiple rounds of incubating the fusion proteins with the immobilized receptor, collecting the fusion proteins that bound to the receptor (along with the accompanying DNA), and producing more of the fusion proteins collected.

Typically, after three rounds of panning, the fusion proteins and accompanying DNA were isolated and cultured to produce fusion protein preparations for an ELISA to determine if the fusion protein bound specifically to the receptor. This assay was carried out similarly to the panning, except that after removing unbound fusion proteins, the wells were treated with rabbit anti-phage antibody (or with anti-lac antibody for the peptides on plasmids system), then with alkaline phosphatase-conjugated goat anti-rabbit antibody, and then the amount of alkaline phosphatase in each well was determined by standard methods. By comparing test wells with control wells (no receptor), one can determine whether the fusion proteins bound to the receptor specifically.

The immobilized receptor used in the panning and ELISA procedures comprised the extracellular domain of the EPO-receptor and was produced in recombinant host cells. This receptor molecule can be produced in a variety of different forms and host cells. One useful form is constructed with a signal peptide for protein secretion and for glycophospholipid membrane anchor attachment (this form of anchor attachment is called "PIG-tailing;" see, Caras and Weddell, 3 Mar., 1989, *Science* 243:1196–1198; and Lin et al., 10 Aug., 1990, *Science* 249:677–679, each of which is incorporated herein by reference). This system allows for cleavage of the receptor from the surface of the cells expressing the receptor and collection of the cleaved receptor quite easily. Preferably, a protease cleavage site, such as a thrombin cleavage site, is inserted between the HPAP epitope of the PIG-tailed receptor and the receptor itself.

The recombinant receptor protein was immobilized using the following methodology. Microtiter plates were coated within an anti-receptor antibody and the wells which were to contain the immobilized receptor were treated with bovine serum albumin (BSA) to block non-specific binding. The PIG-tailed receptor having a thrombin cleavage site was added to the coated wells of the microtiter plate, which were then washed to remove unbound receptor.

When using random peptide generation systems that allow for multivalent ligand-receptor interaction, one must recognize that the density of the immobilized receptor is an important factor in determining the affinity of the ligands that will bind to the immobilized receptor. At higher receptor densities (i.e., each anti-receptor antibody-coated well treated with 0.25 to 0.5 mg of receptor), multivalent binding is more likely to occur (if at all) than at lower receptor densities (i.e., each anti-receptor antibody-coated well treated with 0.5 to 1 ng of the receptor). If multivalent binding is occurring, then one will be more likely to isolate ligands with relatively low affinity. Typically, one can identify lead compounds using a high density of immobilized receptor and then test the derivatives of the lead compound at lower receptor densities to isolate compounds with higher affinity for the receptor than the lead compound.

Often, the receptor was added only to alternate rows of the microtiter plate; the BSA-blocked wells in the "blank" rows served as useful negative controls to determine whether a receptor-specific reaction was creating the observed results. Fusion protein preparations were then added to the wells and incubated to allow binding to the receptor to occur; then, the wells were washed to remove unbound fusion proteins.

With the above systems, a peptide was discovered that bound to the EPO-R. The DNA encoding the fusion protein that bound to the receptor was sequenced. This peptide had the sequence: GGCRIGPITWVCGG (SEQ ID NO:19) (the N-terminal GG residue allowing for cleavage on the phage). This peptide consistently showed low affinities to BSA and to the anti-receptor antibody and high affinity to EPO-R by ELISA. Moreover, the phagemid clone was competed by free EPO and by cognate free peptide. Further, the free peptide was found to compete EPO-phagemid, LacI-EPO fusion, and radioligand. Finally, the free peptide did not compete in IL-2Rαβ binding assays.

A mutagenesis study on this preferred peptide was then conducted. To generate the collection of oligonucleotides that encode the random peptides, the mutagenesis oligomers shown in FIG. 1 were prepared where N was nucleotide A, C, G, or T (equimolar; depending on the methodology employed, other nucleotides can be employed) and K was G or T (equimolar) in the codon motif (NNK). Those of skill in the art will recognize that the NNK motif encodes all of the amino acids, encodes only one stop codon, and reduces codon bias. There are 32 possible codons resulting from the NNK motif: 1 for each of 12 amino acids, 2 for each of 5 amino acids, 3 for each of 3 amino acids, and only one of the three stop codons.

The mutagenesis fusion proteins, along with the DNA encoding them, again were "panned" on immobilized EPO-R. The fusion proteins and accompanying DNA were then isolated and cultured to produce fusion protein preparations for an ELISA to determine if the fusion protein bound specifically to the receptor. Preferred peptides resulting from this study are shown in FIG. 2. These peptides are characterized by the motif "$X_3X_4X_5GPX_6TWX_7X_8$" (SEQ ID NO:1), where each amino acid is indicated by standard one letter abbreviation; $X_6$ is independently selected from any one of the 20 genetically coded L-amino acids or the stereoisomeric D-amino acids; $X_3$ can be C, A, α-amino-γ-bromobutyric acid, or Hoc, where Hoc is homocysteine; $X_4$ can be R, H, L, or W; $X_5$ can be M, F, or I; $X_7$ can be D, E, I, L, or V; and $X_8$ can be C, A, α-amino-γ-bromobutyric acid, or Hoc, where Hoc is homocysteine, provided that either $X_3$ or $X_8$ is C or Hoc.

To ascertain a rough indication of the affinity of the peptides, the phage libraries were also screened using an affinity selection protocol wherein the peptides are competed with EPO (100 nM). This process is repeated typically for two rounds of panning. In subsequent rounds of panning, the competition temperature (4° C. to ambient temperature) and time (15 to 30 minutes) as well as the temperature (4° C. to ambient temperature) of the wash solutions can be altered to further select for peptides with high affinity. Using this affinity selection procedure, peptides sharing the common motif "$X_1YX_2CX_4X_5GPX_6TWX_7CX_9X_{10}X_{11}$" (SEQ ID NO:4), where each amino acid is indicated by standard one letter abbreviation; each $X_1$, $X_2$, $X_6$, $X_9$, $X_{10}$, and $X_{11}$, is independently selected from any one of the 20 genetically coded L-amino acids or the stereoisomeric D-amino acids; $X_4$ can be R, H, L, or W, $X_5$ can be M, F, or I, and $X_7$ can be D, E, I, L, or V, and were isolated. In a more preferred embodiment, the peptide will comprise a sequence of amino acids $X_1YX_2CX_4X_5GPX_6TWX_7CX_9X_{10}X_{11}$ (SEQ ID NO:5), where $X_4$ can be R or H, $X_5$ can be F or M, $X_6$ can be I, L, T, M, or V, $X_7$ is D or V, $X_9$ can be G, K, L, Q, R, S, or T, and $X_{10}$ can be A, G, P, R, or Y. In a most preferred embodiment, the core peptide will comprise a sequence of amino acids $X_1YX_2CX_4X_5GPX_6TWX_7CX_9X_{10}X_{11}$ (SEQ ID NO:6), where $X_1$ can be D, E, L, N, S, T, or V; $X_2$ can be A, H, K, L, M, S, or T; $X_4$ is R or H; $X_9$ can be K, R, S, or T; and $X_{10}$ is P.

Examples of representative peptides falling within this motif and isolated during the affinity selection process are shown in the tables below.

TABLE 1

Peptides from Affinity Selection Protocol

Competition with 100 nM EPO, 15 min. 4° C.

| | |
|---|---|
| GGWVTCRMGPITWVCGVHGG | (SEQ ID NO: 22) |
| GGQLLCGIGPITWVCRWVGG | (SEQ ID NO: 23) |
| GGLYLCRMGPVTWECQPRGG | (SEQ ID NO: 24) |
| GGKYSCFMGPTTWVCSPVGRGV | (SEQ ID NO: 25) |
| GGWVYCRIGPITWVCDTNGG | (SEQ ID NO: 26) |
| GGIYKCLMGPLTWVCTPDGG | (SEQ ID NO: 27) |
| GGMYYCRMGPMTWVCKGAGG | (SEQ ID NO: 28) |
| No Competition | |
| GGTTQCWIGPITWVCRARGG | (SEQ ID NO: 29) |
| GGPYHCRMGPITWVCGPVGG | (SEQ ID NO: 30) |
| GGEYLCRMGPITWVCERYGG | (SEQ ID NO: 31) |
| GGEYRCRMGPISWVCSPQGG | (SEQ ID NO: 32) |
| GGNYTCRFGPLTWECTPQGGGA | (SEQ ID NO: 33) |
| GGNYVCRMGPITWICTPAGG | (SEQ ID NO: 34) |

TABLE 2

Peptides from Affinity Selection Protocol

Second Competition with 100 nM EPO, 15 min. 4° C.

| | |
|---|---|
| GGSWDCRIGPITWVCKWSGG | (SEQ ID NO: 35) |
| GGDYTCRMGPMTWICTATRG | (SEQ ID NO: 36) |
| GGDYNCRFGPLTWVCKPSGG | (SEQ ID NO: 37) |
| GGSYLCRMGPTTWLCTAQRG | (SEQ ID NO: 38) |
| GGDYHCRMGPLTWVCKPLGG | (SEQ ID NO: 9) |
| VGNYMCHFGPITWVCRPGGG | (SEQ ID NO: 10) |
| GGLYLCRMGPQTWMCQPGGG | (SEQ ID NO: 39) |
| GGTYSCHFGPLTWVCKPQGG | (SEQ ID NO: 8) |
| GGDYVCRMGPMTWVCAPYGR | (SEQ ID NO: 40) |
| GGLYECRMGPMTWVCRPGGG | (SEQ ID NO: 41) |
| GGWYSCLMGPMTWVCKAHRG | (SEQ ID NO: 42) |
| GGKYYCWMGPMTWVCSPAGG | (SEQ ID NO: 44) |
| No Competition | |
| GGYVMCRIGPITWVCDIPGG | (SEQ ID NO: 45) |
| GSCLQCCIGPITWVCRHAGG | (SEQ ID NO: 46) |

TABLE 2-continued

Peptides from Affinity Selection Protocol

| | |
|---|---|
| GGNYFCRMGPITWVCQRSVG | (SEQ ID NO: 47) |
| GGEYICRMGPLTWECKRTGG | (SEQ ID NO: 48) |
| GGLYACRMGPITWVCKYMAG | (SEQ ID NO: 49) |
| GGQYLCTFGPITWLCRGAGGGS | (SEQ ID NO: 11) |
| GGVYACRMGPITWVCSPLGG | (SEQ ID NO: 50) |
| GGYTTCRMGPITWVCSAHGG | (SEQ ID NO: 45) |

TABLE 3

Peptides from Affinity Selection Protocol

Competition with 100 nM EPO, 15 min. Room Temp.

| | |
|---|---|
| VGNYMCHFGPITWVCRPGGG | (SEQ ID NO: 10) |
| GGTYKCWMGPMTWVCRPVGG | (SEQ ID NO: 51) |
| GGTYSCHFGPLTWVCKPQGG | (SEQ ID NO: 8) |
| GGDYHCRMGPLTWVCKPLGG | (SEQ.ID NO: 9) |
| GGNYYCRFGPITFECHPTGG | (SEQ ID NO: 53) |
| GGLYACHMGPMTWVCQPLRGGGS | (SEQ ID NO: 54) |
| GGEYKCYMGPITWVCKPEGG | (SEQ ID NO: 55) |
| GGDYVCRMGPMTWVCAPYGRGGS | (SEQ ID NO: 56) |
| No Competition | |
| GGNYVCRMGPITWICTPAGG | (SEQ ID NO: 34) |
| GGDYTCRMGPMTWICTATRG | (SEQ ID NO: 36) |
| GGEYLCRMGPMTWVCTPVGG | (SEQ ID NO: 57) |
| GGSYLCRMGPTTWLCTAQRGGGN | (SEQ ID NO: 58) |
| GGLYTCRMGPITWVCLPAGG | (SEQ ID NO: 59) |
| GGLYKCRMGPMTWVCSPFGG | (SEQ ID NO: 60) |

TABLE 4

Peptides from Affinity Selection Protocol

Competition with 100 nM EPO, 30 min. Room Temp.

| | |
|---|---|
| GGTYSCHFGPLTWVCKPQGG | (SEQ ID NO: 8) |
| GGDYHCRMGPLTWVCKPLGG | (SEQ ID NO: 9) |
| VGNYMCHFGPITWVCRPGGG | (SEQ ID NO: 10) |
| No Competition | |
| GGDYVCRHGPHTWVCAPYGR | (SEQ ID NO: 40) |
| GGDYNCRFGPLTWVCKPSGG | (SEQ ID NO: 37) |

Another mutagenesis library having six random amino acid residues adjacent to a random 8-mer flanked by two cysteine residues was also screened against immobilized EPO-R. The mutagenesis fusion proteins, along with the DNA encoding them, again were "panned" on immobilized EPO-R. The fusion proteins and accompanying DNA were then isolated and cultured to produce fusion protein preparations for an ELISA to determine if the fusion protein bound specifically to the receptor. The preferred pepfide resulting from this study had the sequence GGPHHVY-ACRMGPLTWIC (SEQ ID NO:61) and, thus, is encompassed by the core sequence "YX$_2$X$_3$X$_4$X$_5$GPX$_6$TWX$_7$X$_8$" (SEQ ID NO:2), where each amino acid is indicated by standard one letter abbreviation; each X$_2$ and X$_6$ is independently selected from any one of the 20 genetically coded L-amino acids or the stereoisomeric D-amino acids; X$_3$ can be C, A, α-amino-γ-bromobutyric acid, or Hoc, where Hoc is homocysteine; X$_4$ can be R, H, L, or W; X$_5$ can be M, F, or I; X$_7$ can be D, E, I, L, or V; and X$_8$ can be C, A, α-amino-γ-bromobutyric acid, or Hoc, where Hoc is homocysteine, provided that either X$_3$ or X$_8$ is C or Hoc, wherein the core sequence is coupled at its amino terminus to a six amino acid unit, wherein each amino acid is independently selected from any of the 20 genetically coded L-amino acids or the stereoisomeric D-amino acids.

IC$_{50}$s were calculated for several of the peptides falling within the general motifs described above. These values were determined using the free peptide and are shown in Table 5 below. (Each of these peptides were independently synthesized and are C-terminally amidated, but could be easily prepared as the free carboxy acid or as an ester or other carboxy amide.)

TABLE 5

| Peptide | IC$_{50}$ |
|---|---|
| GGLYLCRFGPVTWDCGYKGG (SEQ ID NO: 7) | 1.67 μM |
| GGTYSCHFGPLTWVCKPQGG (SEQ ID NO: 8) | 237 nm |
| GGDYHCRMGPLTWVCKPLGG (SEQ ID NO: 9) | 179 nm |
| VGNYMCHFGPITWVCRPGGG (SEQ ID NO: 10) | 420 nm |
| GGVYACRMGPITWVCSPLGG (SEQ ID NO: 11) | 352 nm |
| VGNYMAHNGPITWVCRPGG (SEQ ID NO: 12) | 67 μM |

In addition to the foregoing, other mutagenesis studies were carried on this high affinity EPO agonist family of peptides under conditions designed to enrich for higher affinity peptides. As previously described, to enrich for higher affinity peptides, libraries are screened using an affinity selection protocol wherein the peptides are competed with EPO (100 nM). This process is typically repeated for two rounds of panning. In subsequent rounds of panning, the competition temperature (4° C. to ambient temperature) and time (15 to 30 minutes) as well as the temperature of the wash solutions (4° C. to ambient temperature) can be altered to further select for peptides with high affinity. Using these techniques, a mutagenesis library having three random amino acid residues on either side of the flanking sequence YXCRIGPITWVC (SEQ ID NO:62) was also screened against immobilized EPO-R (see, FIG. 3). The mutagenesis fusion proteins, along with the DNA encoding them, again were "panned" on immobilized EPO-R. The fusion proteins and accompanying DNA were then isolated and cultured to produce fusion protein preparations for an ELISA to determine if the fusion protein bound specifically to the receptor. Preferred peptides resulting from this study are set forth in Table 6, infra.

TABLE 6

| | |
|---|---|
| GGEYICVMGPNTWVCSPTRGHGS | (SEQ ID NO: 63) |
| GGEYLCRMGPMTWVSPFTRKGG | (SEQ ID NO: 64) |
| GGQYICRFGPITWQSQPAGGGS | (SEQ ID NO: 65) |
| GREYSCRMGPITWVCMPRASLGS | (SEQ ID NO: 66) |
| GDYLCSMGPITWICVPERGGGS | (SEQ ID NO: 67) |
| ELWYSCRMGPVTWMCGRYQGGGS | (SEQ ID NO: 68) |

In another mutagenesis study, a mutagenesis library having the strongly conserved residues (i.e., Y, C, G, P, T and W) fixed, the other residues randomized and 10 additional residues at the N-terminus before the tyrosine was also screened against immobilized EPO-R (see, FIG. 4A). The mutagenesis fusion proteins, along with the DNA encoding them, again were "panned" on immobilized EPO-R. The fusion proteins and accompanying DNA were then isolated and cultured to produce fusion protein preparations for an ELISA to determine if the fusion protein bound specifically to the receptor. Preferred peptides resulting from this study are set forth in Table 7, infra.

TABLE 7

| | |
|---|---|
| QICRADRKGIYQCWYGPETWICgg | (SEQ ID NO: 69) |
| QQGYSLWLPWYNCVLGPYTWVCgg | (SEQ ID NO: 70) |
| YGGSAAVPWKYGCSLGPVTWVCgg | (SEQ ID NO: 71) |
| QIVSWGLYSGYLCMVGPVTWLCgg | (SEQ ID NO: 72) |
| GSGALSAAGWYGCRVGPLTWVCgg | (SEQ ID NO: 73) |
| SVVSHDAAGVYDCVIGPVTWICgg | (SEQ ID NO: 74) |
| IYSWTGILGSYVCWYGPDTWVCgg | (SEQ ID NO: 75) |
| SCIYVRFFYCYQCSEGPATWLCgg | (SEQ ID NO: 76) |
| TVAKGQSGVRYSCLRGPETWVCgg | (SEQ ID NO: 77) |
| VQPQYKWATMYQCWKGPSTWFCgg | (SEQ ID NO: 78) |
| KSGVWEMGSSYQCARGPRTWCCgg | (SEQ ID NO: 79) |
| CSVRRMDREYYRCCRGPFTWQCgg | (SEQ ID NO: 80) |
| KYQEEMFMGYQCLQGPKTQLCgg | (SEQ ID NO: 81) |
| VCPGSEFRVGYICAMGPYTWDCgg | (SEQ ID NO: 82) |
| SLCSSRCNSPYFCSIGPSTWRCgg | (SEQ ID NO: 83) |
| QASLGLPLKQYLCVLGPHTWLCgg | (SEQ ID NO: 84) |
| ACKPAALFVQYGCVLGPMTWICgg | (SEQ ID NO: 85) |
| SCERAGGRWEYVCQWGPDTWLCgg | (SEQ ID NO: 86) |
| RVARQVQQVSYWCAHGPATCYCgg | (SEQ ID NO: 87) |
| HKYDTLMLTNYVCQRGPLTQLCgg | (SEQ ID NO: 88) |

In still another mutagenesis study, a mutagenesis library having the strongly conserved residues (i.e., Y, C, G, P, T and W) fixed, the other residues randomized and 10 additional residues between the second cysteine and the (Gly)$_4$-Ser (SEQ ID NO:240) linker was also screened against immobilized EPO-R (see, FIG. 4B). In this library, the conserved tyrosine residue was preceded by two glycine residue to allow for efficient signal peptide cleavage. The mutagenesis fusion proteins, along with the DNA encoding them, again were "panned" on immobilized EPO-R. The fusion proteins and accompanying DNA were then isolated and cultured to produce fusion protein preparations for an ELISA to determine if the fusion protein bound specifically to the receptor. Preferred peptides resulting from this study are set forth in Table 8, infra.

TABLE 8

| | |
|---|---|
| ggYHCEWGPETWICRPEISPLTVMgg | (SEQ ID NO: 89) |
| ggYICDYGPLTWACKPAGATLLQPgg | (SEQ ID NO: 90) |
| ggYTCRFGPVTWDCLPAINHNGVLgg | (SEQ ID NO: 91) |
| ggYQ*FMGPETWVCAPEPRVERVSgg | (SEQ ID NO: 240) |
| ggYLCRFGPETWTCAPERSVVTQSgg | (SEQ ID NO: 242) |
| ggYVCDFGPTTWICRGQVMEHINTgg | (SEQ ID NO: 92) |
| ggYMCNMGPLTWDCSPVRSTSMAWgg | (SEQ ID NO: 93) |
| ggYNCTMGPNTWVCTPAAESPAVFgg | (SEQ ID NO: 94) |
| ggYGCRIGPITWICDDVSRSPRA | (SEQ ID NO: 95) |
| ggYTCRMGPQTWECLPMSEGV | (SEQ ID NO: 96) |
| ggYNCKFGPQTWDCSSANLKEV | (SEQ ID NO: 97) |
| gYLCEMGPETWMCRPEDAKLGV | (SEQ ID NO: 98) |
| ggYGCKFGPVTWICEDLLLDPMY | (SEQ ID NO: 99) |
| ggYNCKFGPQTWDCSSANLKEVLV | (SEQ ID NO: 100) |
| YLCEMGPETWMCRPEDCEAW | (SEQ ID NO: 101) |
| ggYGCGLAPVTWECPQVSIPYGLSgg | (SEQ ID NO: 102) |
| ggYGCRIGPTTWICDSTVPQLREVgg | (SEQ ID NO: 103) |
| ggYRSCWAPETWVCDNHSA | (SEQ ID NO: 104) |
| gYLCNFGPITWDCVSSAQSEMQIgg | (SEQ ID NO: 105) |

In yet another mutagenesis study, a mutagenesis library having the strongly conserved residues (i.e., Y, C, G, P, T and W) fixed with the tyrosine placed directly next to the first cysteine and the other amino acids randomized, including 4 residues N-terminal to the tyrosine and 5 between the second cysteine and the linker, was also screened against immobilized EPO-R (see, FIG. 4C). The N-terminal random amino acids were again preceded by two glycine residues to allow for efficient processing. The mutagenesis fusion proteins, along with the DNA encoding them, again were "panned" on immobilized EPO-R. The fusion proteins and accompanying DNA were then isolated and cultured to produce fusion protein preparations for an ELISA to determine if the fusion protein bound specifically to the receptor. Preferred peptides resulting from this study are set forth in Table 9, infra.

TABLE 9

| | |
|---|---|
| ggAELQYCKIGPETWVCDWPHIgg | (SEQ ID NO: 106) |
| ggPYEGYCSGGPVTWECCVSVCgg | (SEQ ID NO: 107) |
| ggQPLPYCSPGPTTWFCINWLFgg | (SEQ ID NO: 108) |
| ggCSYGYCPMGPFTWMCRQRRLgg | (SEQ ID NO: 109) |
| ggVRGSYCQSGPPTWQCDLRFFgg | (SEQ ID NO: 110) |
| ggRCARYCACGPGTWNCLGRCQgg | (SEQ ID NO: 111) |
| ggLGRCYCVYGPLTWWCSQTSLgg | (SEQ ID NO: 112) |
| ggLCVWYCSAGPWTWYCIYRSAgg | (SEQ ID NO: 113) |
| ggKPGPYCSFGPETWVCTALGMgg | (SEQ ID NO: 114) |
| ggRLGEYCEIGPITWICRLFLPgg | (SEQ ID NO: 115) |
| ggPGLGYCDFGPLTWVCDGSVDgg | (SEQ ID NO: 116) |
| ggLSSAYCRYGPETWICWAGTGgg | (SEQ ID NO: 117) |
| ggVLHLYCYYGPETWDCLPIKAgg | (SEQ ID NO: 118) |
| ggGGGVYCLVGPVTWLCGPAAMgg | (SEQ ID NO: 119) |
| ggLTRNYCRIGPETWICQEVAIgg | (SEQ ID NO: 120) |
| ggWSERYCVLGPLTWECVHLFAgg | (SEQ ID NO: 121) |
| ggMPLKYCGMGPVTWVCCEAVSgg | (SEQ ID NO: 122) |
| ggSVMRYCHFGPETWICPYDMPgg | (SEQ ID NO: 123) |
| ggALYPYCLIGPMTWVCQVGWIgg | (SEQ ID NO: 124) |
| ggTYGNYCRGGPGTWHCEDTRGgg | (SEQ ID NO: 125) |
| ggASYCYCSKGPATWKCVGSILgg | (SEQ ID NO: 126) |
| ggSLAAYCLQGPKTWPCVRRRLgg | (SEQ ID NO: 127) |
| ggTDSLYCKLGPLTWHCQLYQKgg | (SEQ ID NO: 128) |
| gISQQYCWRGPATWVCLEWELgg | (SEQ ID NO: 129) |

In addition to the foregoing mutagenesis studies, mutagenesis of peptide GGTYSCHFGPLTWVCKPQGG was performed using a modified C-terminal Lac-I display system in which display valency was reduced with the aim of identifying higher affinity hits ("Headpiece Dimer"). The Lac-I Headpiece Dimer (HPD) Display system is described in greater detail in U.S. Pat. No. 5,338,665, which is hereby incorporated by reference for all purposes. Essentially, the residues which were highly conserved in the previous mutagenesis studies (i.e., Y, C, G, P, T and W) were mutated lightly, whereas the less conserved residues (i.e., H, F, L and V) were subject to a higher level of mutation. Four random residues proceeded the tyrosine residue, the latter being also followed by one random residue. The C-terminus of the mutagenesis scheme ended with 6 random amino acids, following the cysteine. The details of the library construction are set forth in FIG. 5.

The library was screened through four rounds on PIG-tailed EPO-R immunobilized on mAb179, employing EPO elution from round two onward to enrich for higher affinity clones. The resulting DNA inserts were then cloned as a pool into a maltose binding protein (MBP) vector allowing their expression as a C-terminal fusion protein. Crude cell lysates from randomly picked individual MBP fusion clones were then assayed for EPO-R binding in an ELISA format. Preferred peptides resulting from this study are set forth in Table 10, infra.

TABLE 10

| | |
|---|---|
| RTKEYSCQMGPLTWICVPKS | (SEQ ID NO: 130) |
| SKARYMCHMGPLTWVCRPEV | (SEQ ID NO: 131) |
| GGKAYMCRLGPVTWVCSPRIKL | (SEQ ID NO: 132) |
| LLRGYECYMGPLTWVCRSSKPR | (SEQ ID NO: 133) |
| TIAQYICYMGPETWECRPSPKA | (SEQ ID NO: 15) |
| NGRTYSCQLGPVTWVCSRGVRR | (SEQ ID NO: 134) |
| LGRKYSCHFGPLTWVCQPAKKD | (SEQ ID NO: 21) |
| MKTKYKCYMGPLTWVCEGS | (SEQ ID NO: 135) |
| SKTKYRCEMGPLTWVCERW | (SEQ ID NO: 136) |
| LTRLYSCHMGPSTWVCSTALRK | (SEQ ID NO: 137) |
| RGQLYACHFGPVWVCKRRKRV | (SEQ ID NO: 138) |

TABLE 10-continued

| | |
|---|---|
| SGILYECHMGPLTWVCTPSRRR | (SEQ ID NO: 139) |
| GSKTYSCQLGPVTWVCGRKR | (SEQ ID NO: 140) |
| ARGKYQCQFGPLTWECLPIRPR | (SEQ ID NO: 141) |
| VTRMYRCRMGPLTWVCER | (SEQ ID NO: 142) |
| KPSLYECHLGPLTWECRPRRRE | (SEQ ID NO: 143) |
| RGHMYSCQLGPVTWVCKPLSGR | (SEQ ID NO: 144) |
| ITPTYHCKFGPQTWVCAPKRSALTK | (SEQ ID NO: 145) |
| GNRMYQCHMGPLTWVCQPTRIH | (SEQ ID NO: 146) |
| MKTKYKCYMGPLTWVCEGSRLK | (SEQ ID NO: 147) |
| HLGKYDCSFGPQTWVCKPRRSL | (SEQ ID NO: 148) |
| ERRVYECQMGPLTWECKPGVKG | (SEQ ID NO: 149) |
| LGRKYSCHFGPVTWVCQPAKKD | (SEQ ID NO: 243) |
| RGRGYSCQMGPVTWVCKRERYF | (SEQ ID NO: 150) |
| RLREYRCHMGPQTWVCNGHHSK | (SEQ ID NO: 151) |
| SGALYDCQMGPITWVCRANRQK | (SEQ ID NO: 152) |
| TNQVYGCKFGPKTWVCKPAPRI | (SEQ ID NO: 153) |
| TRGMYACHMGPQTWVCRPTQPR | (SEQ ID NO: 154) |
| VLSNYECTMGPKTWVCKPLRLK | (SEQ ID NO: 155) |

One of the most striking features of the peptides obtained using the Lac-I Headpiece Dimer Display system is the accumulation of multiple positive charges in the regions flanking the conserved cysteines, particularly so in RGQ-LYACHFGPVTWVCKRRKRV (SEQ ID NO:138), which has a C-terminal stretch of 5 such residues. Amino acids which were lightly mutagenized (i.e., Y, C, G, P, T and W) were absolutely conserved, whereas new motifs were generated at those positions which were more heavily mutated. Of particular interest is the presence of an additional tyrosine residue in a number of the peptides (see, e.g., LLRGYECYMGPLTWVCRSSKPR (SEQ ID NO:133)), and the presence of two glutamic acid residues between the cysteines in TIAQYICYMGPETWECRPSPKA (SEQ ID NO:15).

In addition to the foregoing mutagenesis studies, mutagenesis of peptide TIAQYICYMGPETWECRPSPKA (SEQ ID NO:15) was performed using a modified C-terminal Lac-I display system similar to the system previously described. Essentially, the residues which were highly conserved in previous mutagenesis studies (i.e., Y, C, G, P, T and W) were fixed, whereas the less conserved residues (i.e., H, F, L and V) were randomized. In addition, the two glutamic acid residues were lightly mutated. Four random residues proceeded the tyrosine residue, the latter being also followed by one random residue. The C-terminus of the mutagenesis scheme ended with 6 random amino acids following the cysteine. The details of the library construction are set forth in FIG. 6.

The library was screened through three rounds on PIG-tailed EPO-R immobilized on mAb179, employing EPO elufion from round two onward to enrich for higher affinity clones. Colony lifts were performed probing with the human Fcγ-EBP reagent, followed by goat anti-human Fcγ conjugated to akaline phosphatase the latter of which is available from Sigma Chemical Co., St. Louis, Mo. Thereafter, the HPD plasmids identified were sequenced. Peptides resulting from this study are set forth in Table 11, infra.

TABLE 11

| | |
|---|---|
| ALKKYDCYFGPETWECLARRPH | (SEQ ID NO: 156) |
| ERRFYKCRFGPETWECTL | (SEQ ID NO: 157) |
| FGQEYRCHLGPETWQCSPVRVG | (SEQ ID NO: 158) |
| FRPEYMCRMGPETWECGGARP | (SEQ ID NO: 159) |
| GSRKYwCRMGPETWECMKPVRL | (SEQ ID NO: 160) |
| GLKAYGCRYGPETWDCRSVILI | (SEQ ID NO: 161) |
| IRQPYICHMGPETWECGRYPAG | (SEQ ID NO: 162) |
| KGASYHCIMGPETWECIPQRV | (SEQ ID NO: 163) |
| MKQLYSCIMGPETWECRPGVER | (SEQ ID NO: 164) |
| QRHYYRCALGPETWECRPMSPE | (SEQ ID NO: 165) |
| TKRLYHCHMGPETWECHGPMRK | (SEQ ID NO: 166) |
| TRPSYRCAFGPVTWECIPAR | (SEQ ID NO: 167) |
| RHKSYVCTFGPETWECTGAIRR | (SEQ ID NO: 168) |
| RGRMYNCRMGPETWECKGQSKD | (SEQ ID NO: 169) |
| RRRYYRCWMGPETWECSPVSNK | (SEQ ID NO: 170) |
| VADNYDCPIGPVTWECIHVRAS | (SEQ ID NO: 171) |
| VQKKYLCHFGPETWECGPDRD | (SEQ ID NO: 172) |
| WQTWYICERGPETWECRWLVL | (SEQ ID NO: 173) |
| YRMPYRCKMGPETWECVGGRGR | (SEQ ID NO: 174) |
| YSREYSCRMGPETWECXRGFLR | (SEQ ID NO: 175) |

The foregoing pool of pepfide sequences were then cloned into a maltose binding protein (MBP) vector allowing their expression as a C-terminal fusion protein. Crude cell lysates from randomly picked individual MBP fusion clones were then assayed for EPO-R binding in an ELISA format. Preferred peptides resulting from this study are set forth in Table 12, infra.

TABLE 12

| | |
|---|---|
| RSMWYRCQMGPQTWVCGPRSAS | (SEQ ID NO: 176) |
| SRREYICHLGPQTWVCGPGGR | (SEQ ID NO: 177) |
| GSPSYHCHLGPLTWVCKPHRMR | (SEQ ID NO: 178) |
| MVGRYQCHMGPRTWVCKPWHG | (SEQ ID NO: 179) |
| GTARYQCHFGPLTWVCKPSLKG | (SEQ ID NO: 180) |
| ELRGYICHFGPVTWVCKPNGSR | (SEQ ID NO: 181) |
| LKQGYQCQLGPQTWVCRPLRMP | (SEQ ID NO: 182) |
| KERKYECQFGPRTWVCQPTRAN | (SEQ ID NO: 183) |
| VRKVYACHMGPVTWVCVPGYKG | (SEQ ID NO: 184) |
| SGQRYVCRMGPETWVCRSYRGL | (SEQ ID NO: 185) |
| ERRSYSCQMGPVTWVCGRQMGQ | (SEQ ID NO: 186) |
| VKNNYRCQFGPVTWVCKAFR | (SEQ ID NO: 187) |
| SGASYDCQMGPITWVCRANRQK | (SEQ ID NO: 188) |

Representative peptides which were found to bind specifically to the EPO-receptor were also tested in cell-based functional assays. One assay utilized FDCP-1, a growth factor dependent murine multi-potential primitive hematopoietic progenitor cell line (see, e.g., Dexter et al. (1980) *J. Exp. Med.* 152:1036–1047), as the parental cell line. This cell line can proliferate, but not differentiate, when supplemented with WEHI3-conditioned media (a medium that contains IL-3, ATCC number T1B68). The parental cell line is transfected with the human or murine EPO-R as described below to produce the FDCP-1-hEPO-R or FDCP-1-mEPO-R cell line, respectively. These transfected cell lines can proliferate, but not differentiate, in the presence of human or murine EPO.

Figure 7:
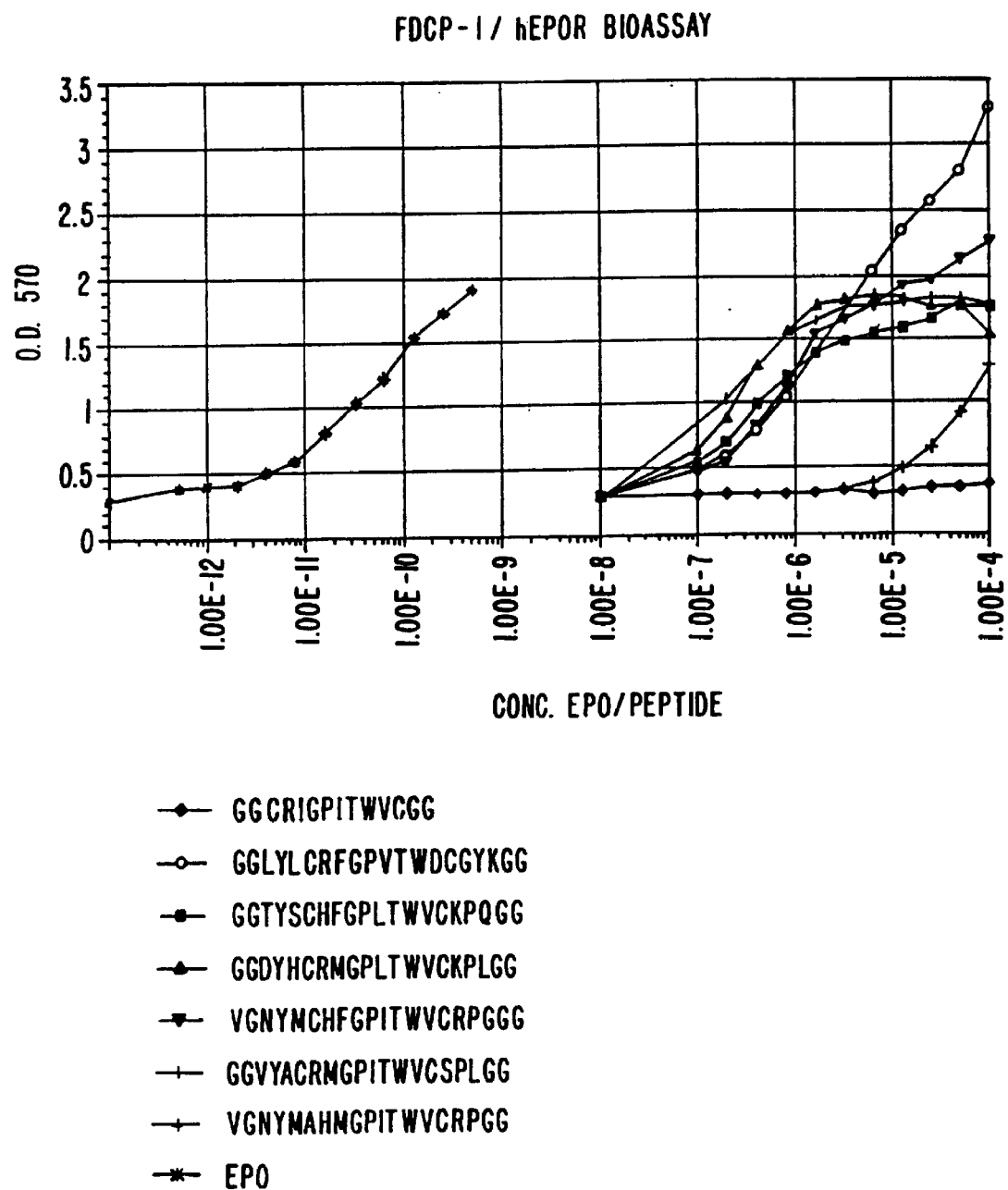

In brief, the cells are grown to half stationary density in the presence of the necessary growth factors. The cells are then washed in PBS and starved for 16–24 hours in whole media without the growth factors. After determining the viability of the cells, stock solutions (in whole media without the growth factors) are made to give about $10^5$ cells per 50 microliters. Ser. dilutions of the compounds (typically the free, solution phase peptide as opposed to a phage-bound or other bound or immobilized peptide) to be tested are made in 96-well tissue culture plates for a final volume of 50 microliters per well. Cells (50 microliters) are added to each well and the cells are incubated 24–48 hours, at which point the negative controls should die or be quiescent. Cell proliferation is then measured by techniques known in the art, such as an MTT assay which correlates with $^3$H-thymidine incorporation as an indication of cell proliferation (see, Mosmann (1983) *J. Immunol. Methods* 65:55). FIG. 7 illustrates the results of this assay for EPO and for the peptides listed in Table 5 above. Peptides which bind to the EPO receptor and exhibit activity in the FDCP-1/hEPO-R cell based bioassay are preferred compounds of the invention.

A second cell based assay utilized the TF-1 cell line. See, Kitamura et al. (1989) *Blood* 73:375–380, which is incorporated herein by reference. Representative results are shown in FIG. 8. FIG. 8 depicts the effects of EPO and the free peptide VGNYMCHFGPITWVCRPGGG (SEQ ID NO:10) on cellular proliferation of the cell line TF-1.

Figure 9B:
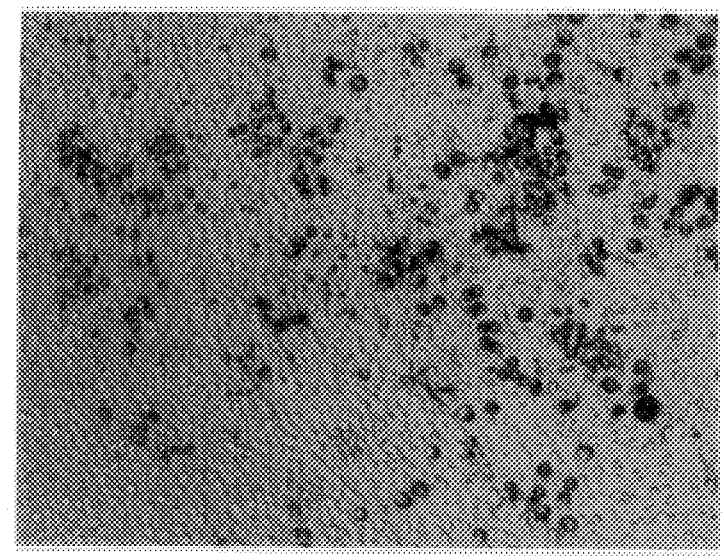
Figure 9C:
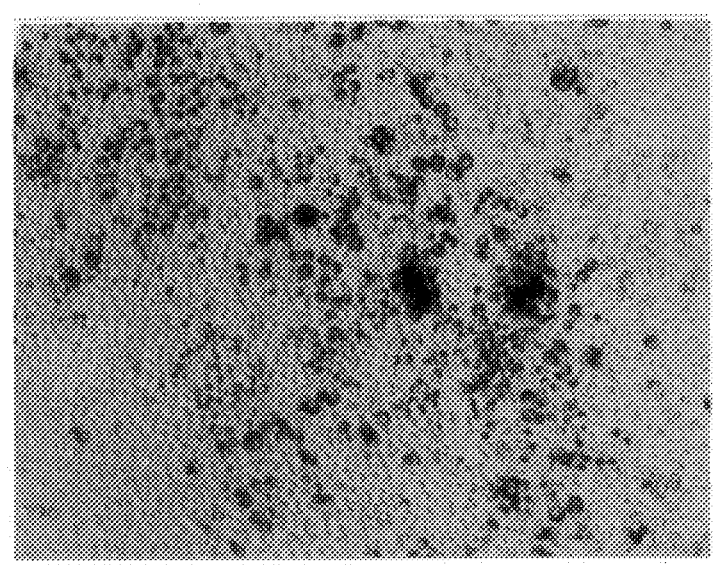

Another cell based assay which further illustrates the ability of the compounds of this invention to act as EPO agonists is based on $^3$H-thymidine incorporation into spleen cells of phenylhydrazine treated mice. The results of this assay are shown in FIGS. 9A–9C.

Other biological assays that can be used to demonstrate the activity of the compounds of the present invention are disclosed in Greenberger et al. (1983) *Proc. Natl. Acad. Sci. USA* 80:2931–2935 (EPO-dependent hematopoietic progenitor cell line); Quelle and Wojchowski (1991) *J. Biol. Chem.* 266:609–614 (protein tyrosine phosphorylation in B6SUt.EP cells); Dusanter-Fourt et al. (1992) *J. Biol. Chem.* 287:10670–10678 (tyrosine phosphorylation of EPO-receptor in human EPO-responsive cells); Quelle et al. (1992) *J. Biol. Chem.* 267:17055–17060 (tyrosine phosphorylation of a cytosolic protein (pp100) in FDC-ER cells); Worthington et al. (1987) *Exp. Hematol.* 15:85–92 (colorimetric assay for hemoglobin); Kaiho and Miuno (1985) *Anal. Biochem.* 149:117–120 (detection of hemoglobin with 2,7-diaminofluorene); Patel et al. (1992) *J. Biol. Chem.* 267:21300–21302 (expression of c-myb; Witthuhn et al. (1993) *Cell* 74:227–236 (association and tyrosine phosphorylation of JAK2); Leonard et al. (1993) *Blood* 82:1071–1079 (expression of GATA transcription factors); Ando et al. (1993) *Proc. Natl. Acad. Sci. USA* 90:9571–9575 (regulation of $G_1$/3 transition by cycling D2 and D3); and calcium flux, each of which is incorporated herein by reference.

An instrument designed by Molecular Devices Corp., known as a microphysiometer, has been reported to be successfully used for measurement of the effect of agonists and antagonists on various receptors. The basis for this apparatus is the measurement of the alterations in the acidification rate of the extracellular media in response to receptor activation.

According to a preferred embodiment, the peptides of the present invention are dimerized or oligomerized, thereby increasing the affinity and/or activity of the lead compounds disclosed herein. To investigate the effect that peptide dimerization/oligomerization has on EPO mimetic potency in cell proliferation assays, a C-terminally biotinylated analog of GGTYSCHFGPLTWVCKPQGG (SEQ ID NO:8) was synthesized (i.e., GGTYSCHFGPLTWVCKPQGGSSK (SEQ ID NO:20) (Ahx-biotin)).

This peptide was incubated with streptavidin in PBS at a 4:1 molar ratio at room temperature for one hour. Following this, the complex was introduced into the PIG-tailed EPO-R binding assay for $IC_{50}$ determination. Peptide that had not been complexed to streptavidin was also run in the same experiment. Pre-complexed peptide was found to have an $IC_{50}$ of 20 nM compared to the 350 nM $IC_{50}$ of peptide that had not been incubated with streptavidin. This greater than 10-fold increase in apparent affinity is presumably due to the multivalent state of the peptide-streptavidin complex. Since this comparison was made using the free peptide concentrations and not the effective complex concentration (theoretically 4-fold lower), the effect will be even greater.

In addition, this peptide was preincubated with streptavidin in serum-free HEPES-buffered RPMI at a 4:1 molar ratio, as above. The complex was tested for stimulation of cell proliferation in an FDCP-1/hEPO-R bioassay alongside free GGTYSCHFGPLTWVCKPQGGSSK (SEQ ID NO:20) (Ahx-biotin)) and the unbiotinylated parental peptide, i.e., GGTYSCHFGPLTWVCKPQGG (SEQ ID NO:8). FIG. 10 illustrates the results of the assay where the EPO-$ED_{50}$ of the free peptides were similar (approximately 1 $\mu$M), but that of the pre-formed streptavidin complex was less than 10 nM, a two log reduction in EPO-$ED_{50}$. Streptavidin, alone, had some small stimulatory effect at the highest concentrations, presumably due to contamination with bacterial endotoxin.

In addition, an increase in biological potency was found when the peptide was dimerization with goat anti-biotin IgG. FIG. 11 illustrates that a one log reduction in EPO-$ED_{50}$ can also be achieved by preincubation of GGTYSCHFGPLTWVCKPQGGSSK (SEQ ID NO:20) (Ahx-biotin) with purified goat anti-biotin IgG at a 2:1 molar ratio. This increase in biological potency is presumably due to the dimerization of the peptide by the antibodies. The anti-biotin antibodies alone had no effect on the cells. Moreover, a 100-fold reduction in EPO-$ED_{50}$ was seen with the GGTYSCHFGPLTWVCKPQGGSSK (SEQ ID NO:20) (Ahx-biotin)-streptavidin complex. As such, by dimerizing or oligomerizing the lead peptides of the present invention, the affinity and/or activity of such peptides can be increased.

In another embodiment, a dimeric peptide analog of GGTYSCHFGPLTWVCKPQGG (SEQ ID NO:8) containing two disulfide bonds was prepared using the general scheme set forth in FIG. 12. Briefly, the first peptide chain was assembled on a Tentagel resin. The Fmoc-Lys(Alloc) was coupled to the Knorr linker, the Alloc group being used as an orthogonal protecting group. For the first peptide chain, Cys(Acm) was used. After the completion of the first peptide chain, the Alloc group was removed and the second peptide chain was built upon the side chain amines of the lysine residue. In this peptide chain, Cys(trt) was used. After the synthesis was completed, the peptide was cleaved from the resin and purified. The peptide was then cyclized to a compound containing a single disulfide bond. Thereafter, the second disulfide bond was formed by iodine oxidation, yielding the bicyclic dimer.

FIGS. 13 and 14 show the in vitro EPOR binding and biological activities of the dimer. The affinity of the dimer was tested against the PIG-tailed EPOR immobilized on mAb179 in strip wells. The result of the equilibrium competition binding assay indicated an affinity of approximately 2 nM, a 200-fold increase over the value for the parental peptide, GGTYSCHFGPLTWVCKPQGG (SEQ ID NO:8), (200 nM), and 5-fold over the GGTYSCHFGPLTWVCK-PQGGSSK (SEQ ID NO:20) (Ahx-biotin)-streptavidin complex. In vitro bioactivity, as measured by FDCP-1/hEPOR cell proliferation, was increased approximately 20-fold from an $EC_{50}$ of 400 nM (for the parental peptide) to 20 nM. As such, by dimerizing or oligomerizing the lead peptides of the present invention, the affinity and/or activity of such peptides can be significantly increased.

The peptides of this invention or derivatives thereof can be conjugated to compounds that bind to the EPO-R to construct compounds with an affinity for the receptor greater than either of the compounds of which the conjugate is composed. The discovery of these peptides also facilitates the identification of peptides that bind to the same site on the EPO-R, because one can bias the library or panning procedure to eliminate peptides with the complementary "non-blocking" motif.

The preferred motif sequence also provides a means to determine the minimum size of an EPO agonist of the invention. Using the "encoded synthetic library" (ESL) system described in U.S. patent application Ser. No. 946,239, filed Sep. 16, 1992, which is a continuation-in-part application of Ser. No. 762,522, filed Sep. 18, 1991, or the "very large scale immobilized polymer synthesis" system described in U.S. patent application Ser. Nos. 492,462, filed Mar. 7, 1990; 624,120, filed Dec. 6, 1990; and 805,727, filed Dec. 6, 1991; one can not only determine the minimum size of a peptide with such activity, one can also make all of the peptides that form the group of peptides that differ from the preferred motif (or the minimum size of that motif) in one, two, or more residues. This collection of peptides can then be screened for the ability to bind to EPO-receptor. This immobilized polymer synthesis system or other peptide synthesis methods can also be used to synthesize every truncation analog and every deletion analog and every combination of truncation and deletion analog of all of the peptide compounds of the invention.

The peptides of the invention can also be prepared by classical methods known in the art, for example, by using standard solid phase techniques. The standard methods include exclusive solid phase synthesis, partial solid phase synthesis methods, fragment condensation, classical solution synthesis, and even by recombinant DNA technology. See, e.g., Merrifield, 1963, *J. Am. Chem. Soc.* 85:2149, incorporated herein by reference. On solid phase, the synthesis is typically commenced from the C-terminal end of the peptide using an α-amino protected resin. A suitable starting material can be prepared, for instance, by attaching the required α-amino acid to a chloromethylated resin, a hydroxymethyl resin, or a benzhydrylamine resin. One such chloromethylated resin is sold under the tradename BIO-BEADS SX-1 by Bio Rad Laboratories, Richmond, Calif., and the preparation of the hydroxymethyl resin is described by Bodonszky et al., 1966, *Chem. Ind.* (London) 38:1597. The benzhydrylamine (BHA) resin has been described by Pietta and Marshall, 1970, *Chem. Commn.* 650, and is commercially available from Beckman Instruments, Inc., Palo Alto, Calif., in the hydrochloride form.

Thus, the compounds of the invention can be prepared by coupling an α-amino protected amino acid to the chloromethylated resin with the aid of, for example, cesium bicarbonate catalyst, according to the method described by Gisin, 1973, *Helv. Chim. Acta* 56:1467. After the initial coupling, the α-amino protecting group is removed by a choice of reagents including trifluoroacetic acid (TFA) or hydrochloric acid (HCl) solutions in organic solvents at room temperature.

The α-amino protecting groups are those known to be useful in the art of stepwise synthesis of peptides. Included are acyl type protecting groups (e.g., formyl, trifluoroacetyl, acetyl), aromatic urethane type protecting groups (e.g., benzyloxycarboyl (Cbz) and substituted Cbz), aliphatic urethane protecting groups (e.g., t-butyloxycarbonyl (Boc), isopropyloxycarbonyl, cyclohexyloxycarbonyl) and alkyl type protecting groups (e.g., benzyl, triphenylmethyl). Fmoc is a preferred protecting group. The side chain protecting group (typically ethers, esters, trityl, PMC, and the like) remains intact during coupling and is not split off during the deprotection of the amino-terminus protecting group or during coupling. The side chain protecting group must be removable upon the completion of the synthesis of the final peptide and under reaction conditions that will not alter the target peptide.

The side chain protecting groups for Tyr include tetrahydropyranyl, tert-butyl, trityl, benzyl, Cbz, Z-Br-Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting groups for Thr and Ser are benzyl. The side chain protecting groups for Arg include nitro, Tosyl (Tos), Cbz, adamantyloxycarbonyl mesitoylsulfonyl (Mts), or Boc. The side chain protecting groups for Lys include Cbz, 2-chlorobenzyloxycarbonyl (2-Cl-Cbz), 2-bromobenzyloxycarbonyl (2-BrCbz), Tos, or Boc.

After removal of the α-amino protecting group, the remaining protected amino acids are coupled stepwise in the desired order. Each protected amino acid is generally reacted in about a 3-fold excess using an appropriate carboxyl group activator such as 2-(1H-benzotriazol-1-yl)-1,1,3,3tetramethyluronium hexafluorophosphate (HBTU) or dicyclohexylcarbodiimide (DCC) in solution, for example, in methylene chloride ($CH_2Cl_2$), dimethyl formamide (DMF) mixtures.

After the desired amino acid sequence has been completed, the desired peptide is decoupled from the resin support by treatment with a reagent such as trifluoroacetic acid (TFA) or hydrogen fluoride (HF), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

In preparing the esters of the invention, the resins used to prepare the peptide acids are employed, and the side chain protected peptide is cleaved with base and the appropriate alcohol, i.e., methanol. Side chain protecting groups are then removed in the usual fashion by treatment with hydrogen fluoride to obtain the desired ester. These solid phase peptide synthesis procedures are well-known in the art and further described in Stewart, Solid Phase Peptide Syntheses (Freeman and Co., San Francisco, 1969).

These procedures can also be used to synthesize peptides in which amino acids other than the 20 naturally occurring, genetically encoded amino acids are substituted at one, two, or more positions of any of the compounds of the invention. For instance, naphthylalanine can be substituted for tryptophan, facilitating synthesis. Other synthetic amino acids that can be substituted into the peptides of the present invention include L-hydroxypropyl, L-3,4-dihydroxyphenylalanyl, δ amino acids such as L-δ-hydroxylysyl and D-δ-methylalanyl, L-α-methylalanyl, β amino acids, and isoquinolyl. D-amino acids and non-naturally occurring synthetic amino acids can also be incorporated into the peptides of the present invention.

One can also modify the amino and/or carboxy terminus of the peptide compounds of the invention to produce other compounds of the invention. Amino terminus modifications include methylating (i.e., —$NHCH_3$ or —$N(CH_3)_2$), acetylating, adding a benzyloxycarbonyl (Cbz) group, or blocking the amino terminus with any blocking group containing a carboxylate functionality defined by RCOO— or sulfonyl functionality defined by R—SO$_2$—, where R is selected from the group consisting of alkyl, aryl, heteroaryl, alkyl aryl, and the like, and similar groups. Carboxy terminus modifications include replacing the free acid with a carboxamide group or forming a cyclic lactam at the carboxy terminus to introduce structural constraints. One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the 20 genetically encoded amino acids (or the stereoisomeric D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. In particular, proline analogues in which the ring size of the proline residue is changed from 5 members to 4, 6, or 7 members can be employed.

Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify peptides by phosphorylation, and other methods for making peptide derivatives of the compounds of the present invention are described in Hruby et al., 1 Jun., 1990, *Biochem J.* 268:249–262, incorporated herein by reference. Thus, the peptide compounds of the invention also serve as structural models for non-peptidic compounds with similar biological activity. Those of skill in the art recognize that a variety of techniques are available for constructing compounds with the same or similar desired biological activity as the lead peptide compound, but with more favorable activity than the lead with respect to solubility, stability, and susceptibility to hydrolysis and proteolysis. See, Morgan and Gainor, 1989, *Ann. Rep. Med. Chem.* 24:243–252, incorporated herein by reference. These techniques include replacing the peptide backbone with a backbone composed of phosphonates, amidates, carbamates, sulfonamides, secondary amines, and N-methylamino acids.

According to another preferred embodiment, residues $X_3$ and $X_8$ will be independently selected from the group of C and Hoc. Thus, the compounds of the present invention may exist in a cyclized form with an intramolecular disulfide bond. Alternatively, an intermolecular disulfide bond can be produced to yield a dimeric compound. These intramolecular or intermolecular disulfide derivatives can be represented schematically as shown below:

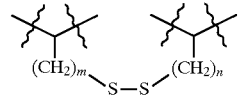

wherein m and n are independently 1 or 2.

Other embodiments of this invention provide for analogues of these disulfide derivatives in which one of the sulfurs has been replaced by a CH$_2$ group or other isostere for sulfur. These analogues can be prepared from the compounds of the present invention wherein either $X_3$ or $X_8$ is C or Hoc and the other is α-amino-γ-butyric acid, via an intramolecular or intermolecular displacement, using methods known in the art as shown below:

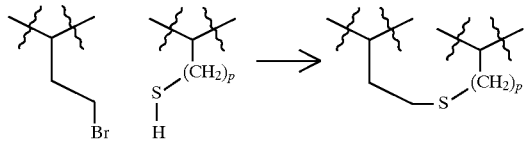

wherein p is 1 or 2. One of skill in the art will readily appreciate that this displacement can also occur using other homologs of α-amino-γ-butyric acid and homocysteine.

In addition to the foregoing cyclization strategies, other non-disulfide peptide cyclization strategies can be employed. Such alternative cyclization strategies include, for example, amide-cyclization strategies as well as cyclization strategies involving the formation of thio-ether bonds. Thus, the compounds of the present invention can exist in a cyclized form with either an intramolecular amide bond or an intramolecular thio-ether bond. To illustrate the feasibility of the amide-cyclization strategy, a peptide based on ggTYSCHFGPLTWVCKPQgg (SEQ ID NO:8) was synthesized wherein the first cysteine was replaced with lysine, the second cysteine was replaced with glutamic acid, and a cyclic monomer was formed through an amide bond between the side chains of these two residues. In addition, to illustrate the feasibility of the thio-ether cyclization strategy, a peptide based on ggTYSCHFGPLTWVCKPQgg (SEQ ID NO:8) was synthesized wherein the first cysteine was replaced with lysine and a cyclic monomer was formed through a thio-ether linkage between the side chains of the lysine residue and the C-terminal cysteine. As such, in addition to disulfide cyclization strategies, amide-cyclization strategies and thio-ether cyclization strategies can both be readily used to cyclize the compounds of the present invention.

Alternatively, the amino-terminus of the peptide can be capped with an alpha-substituted acetic acid, wherein the alpha substituent is a leaving group, such as an α-haloacetic acid, for example, α-chloroacetic acid, α-bromoacetic acid, or α-iodoacetic acid. The compounds of the present invention wherein $X_3$ is C or Hoc can be cyclized via displacement of the leaving group by the sulfur of the $X_3$ residue. See, e.g., Barker et al. (1992) *J. Med. Chem.* 35:2040–2048 and Or et al. (1991) *J. Org. Chem.* 56:3146–3149, each of which is incorporated herein by reference.

The compounds of the invention are useful in vitro as unique tools for understanding the biological role of EPO, including the evaluation of the many factors thought to influence, and be influenced by, the production of EPO and the binding of EPO to the EPO-R (e.g., the mechanism of EPO signal transduction/receptor activation). The present compounds are also useful in the development of other compounds that bind to the EPO-R, because the present compounds provide important structure-activity relationship (SAR) information that facilitate that development.

Moreover, based on their ability to bind to the EPO receptor, the peptides of the present invention can be used as reagents for detecting EPO receptors on living cells, fixed cells, in biological fluids, in tissue homogenates, in purified, natural biological materials, etc. For example, by labelling such peptides, one can identify cells having EPO-R on their surfaces. In addition, based on their ability to bind the EPO receptor, the peptides of the present invention can be used in in situ staining, FACS (fluorescence-activated cell sorting), Western blotting, ELISA (enzyme-linked immunoadsoptive assay), etc. In addition, based on their ability to bind to the EPO receptor, the peptides of the present invention can be used in receptor purification, or in purifying cells expressing EPO receptors on the cell surface (or inside permeabilized cells).

The compounds of the invention can also be utilized as commercial research reagents for various medical research and diagnostic uses. Such uses can include but are not limited to: (1) use as a calibration standard for quantitating the activities of candidate EPO agonists in a variety of functional assays; (2) use as blocking reagents in random peptide screening, i.e., in looking for new families of EPO receptor peptide ligands, the peptides can be used to block recovery of the presently claimed EPO peptides; (3) use in the co-crystallization with EPO receptor, i.e., the peptides of the present invention will allow formation of crystals bound to the EPO receptor, enabling the determination of receptor/peptide structure x-ray crystallography; (4) use to measure the capacity of erythrocyte precursor cells to differentiate and thus, stimulate the induction of globin synthesis and increases in the synthesis of the heme complex and in the number of ferritin receptors; (5) use to maintain the proliferation and growth of EPO-dependent cell lines, such as the FDCP-1-mEPO-R and the TF-1 cell lines; and (6) other research and diagnostic applications wherein the EPO-receptor is preferably activated or such activation is conveniently calibrated against a known quantity of an EPO agonist, and the like.

The compounds of the invention can also be administered to warm blooded animals, including humans, to simulate the binding of EPO to the EPO-R in vivo. Thus, the present invention encompasses methods for therapeutic treatment of disorders associated with a deficiency of EPO that comprise administering a compound of the invention in amounts sufficient to stimulate the EPO-R and thus, alleviate the symptoms associated with a deficiency of EPO in vivo. For example, the compounds of this invention will find use in the treatment of end-stage renal failure/dialysis; anemia associated with AIDS, anemia associated with chronic inflammatory diseases (for example, rheumatoid arthritis and chronic bowel inflammation), autoimmune disease, and malignancies; and for boosting the red blood count of a patient prior to surgery.

Other embodiments of this invention provide for the administration of the compounds of the invention for the treatment of disorders which are not characterized by low or deficient red blood cells, for example as a pretreatment prior to transfusions. In addition, administration of the compounds of this invention can result in a decrease in bleeding time and thus, will find use in the administration to patients prior to surgery or for indications wherein bleeding is expected to occur. In addition, the compounds of this invention will find use in the activation of megakaryoctes.

Since EPO has been shown to have a mitogenic and chemotactic effect on vascular endothelial cells as well as an effect on central cholinergic neurons (see, e.g., Amagnostou et al. (1990) Proc. Natl. Acad. Sci. USA 87:5978–5982 and Konishi et al. (1993) Brain Res. 609:29–35), the compounds of this invention will also find use for the treatment of a variety of vascular disorders, such as promoting wound healing, growth of collateral coronary blood vessels (such as those that may occur after myocardial infarction), trauma, and post-vascular graft treatment, and a variety of neurological disorders, generally characterized by low absolute levels of acetyl choline or low relative levels of acetyl choline as compared to other neuroactive substances e.g., neurotransmitters.

Accordingly, the present invention includes pharmaceutical compositions comprising, as an active ingredient, at least one of the peptides or other compounds of the invention in association with a pharmaceutical carrier or diluent. The compounds of this invention can be administered by oral, parenteral (intramuscular, intraperitoneal, intravenous (IV) or subcutaneous injection), transdermal (either passively or using iontophoresis or electroporation), transmucosal (nasal, vaginal, rectal, or sublingual) routes of administration or using bioerodible inserts and can be formulated in dosage forms appropriate for each route of administration.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating, agents such as magnesium stearate. In the case of capsules, tablets, and pills, the dosage forms may also comprise buffering, agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired. Generally dosage levels of between 0.001 to 10 mg/kg of body weight daily are administered to mammals.

As can be appreciated from the disclosure above, the present invention has a wide variety of applications. Accordingly, the following examples are offered by way of illustration, not by way of limitation.

EXAMPLE 1

Solid Phase Peptide Synthesis

Various peptides of the invention were synthesized using the Merrifield solid phase synthesis techniques (see, Stewart, J. M., and Young, J. D., *Solid Phase Peptide Synthesis*, 2d. edition (Pierce Chemical, Rockford, Ill., 1984)) on a Milligen/Biosearch 9600 automated instrument. The resin used was PAL (Milligen/Biosearch), which is cross-linked polystyrene with 5-(4'-Fmoc-aminomethyl-3,5'-dimethoxyphenoxy) valeric acid as a linker. Use of PAL resin results in a carboxyl terminal amide function upon cleavage of the peptide from the resin. Primary amine protection on amino acids was achieved with F-moc, and side chain protection groups were t-butyl for serine and tyrosine hydroxyls, trityl for glutamine amides, and Pmc (2,2,5,7,8-pentamethylchroman sulfonate) for the arginine guanidino group. Each coupling was performed for either one or two hours with BOP (benzotriazolyl N-oxtrisdimethylaminophosphonium hexafluorophosphate) and HOBt (1-hydroxybenztriazole).

In the synthesis of peptides with an amidated carboxy terminus, the fully assembled peptide was cleaved with a mixture of 90% trifluoroacetic acid, 5% ethanedithiol, and 5% water, initially at 4° C., and gradually increasing to room temperature over 1.5 hours. The deprotected product was filtered from the resin and precipitated with diethyl ether. After thorough drying the product was purified by C18 reverse phase high performance liquid chromatography with a gradient of acetonitrile/water in 0.1% trifluoroacetic acid.

EXAMPLE 2

Bioassays

A. FDCP-1/mEPO-R

The FDCP-1/mEPO-R cells ($10^5$) were grown to half stationary density in the presence of growth factors (2.5 nm EPO). The cells were washed twice in PBS and then starved for 24 hours in whole media minus growth factors.

Cell viability was determined by trypan blue staining. Stock in whole media minus growth factors was made to give desired number of cells per 50 μl. The compounds to be tested were diluted 2-fold in 96 well tissue culture plate (50 μl per well final).

Cells (50 μl per well) were added to each well and incubated 24–48 hours (when the negative controls should die). Cell proliferation was determined by MTT assay.

B. TF-1

The procedure set forth in Kitamura et al. (*Blood* 73:375–380 (1989), which is incorporated herein by reference) relating to the cell line TF-1 having growth dependency on EPO was also conducted to demonstrate the activities of the compounds of the present invention as EPO agonists. Representative results are shown in FIG. 8. FIG. 8 depicts the effects of EPO and the peptide VGNYMCHFGPITWVCRPGGG (SEQ ID NO:10) on cellular proliferation of the cell line TF-1.

C. Spleen Cell Proliferation

The procedure set forth in Krystal (*Exp. Hematol.* 11:649–660 (1983), which is incorporated herein by reference) for a microassay based on $^3$H-thymidine incorporation into spleen cells was also employed to ascertain the ability of the compounds of the present invention to serve as EPO agonists. In brief, B6C3F$_1$, mice were injected daily for two days with phenylhydrazine (60 mg/kg). On the third day, spleen cells were removed and their ability to proliferate over 24 hours using an MTT assay was ascertained. Photographs showing the proliferation of representative populations of spleen cells are shown in FIGS. 9A (control), 9B (treated with 500 pM EPO), and 9C (treated with 25 μm GGDYHCRMGPLTWVCKPLGG (SEQ ID NO:9)) at 200× magnification.

D. Cellular Prolferation: Peptide Dependent Growth of the EPO-Responsive Cell Line, FDC-P1/ER 1. Materials and Method a. Sample Preparation: Peptides were resuspended in DMSO as a $1\times10^{-2}$M stock solution and serially diluted in 10-fold increments to generate the following 100× solutions:

$$1 \times 10^{-3}\ 1 \times 10^{-4}\ 1 \times 10^{-5}\ 1 \times 10^{-6}\ 1 \times 10^{-7}\ 1 \times 10^{-8}$$

Two μl of each stock dilution was added to a cell well as described below in a total volume of 200 μl to generate final concentrations as follows:

$$1 \times 10^{-5}\ 1 \times 10^{-6}\ 1 \times 10^{-7}\ 1 \times 10^{-8}\ 1 \times 10^{-9}\ 1 \times 10^{-10}$$

b. Cell Proliferation Assay:

i. Cell source: FDC-P1/ER, (Dexter, et al., *J. Exp. Med.* (1980) 152:1036–1047, which is incorporated herein by reference), is a well characterized non transformed murine bone marrow derived cell line in which the erythropoietin receptor has been stably transfected. Cells exhibit EPO dependent proliferation.

c. Experimental Protocol: Cells maintained in RPMI 1640/10% Fetal Bovine Serum/antibiotics and 10 U/ml erythropoietin are grown to stationary phase. Cells are harvested and resuspended in fresh medium without growth factor (erythropoietin) for 24 hr. Cells are counted and resuspended at a concentration of 800,000 cells/ml. Approximately forty thousand cells (50μl) are added to each well of a 96 well microtiter plate. Peptide is added to each well in triplicate. A standard dose response determination is run with each series of peptides. After a forty-two hr incubation (≈2 doubling), each well is pulsed with 1 μCi/well Thymidine. Cells are incubated an additional six hr at which time cells are harvested and counted to assess thymidine incorporation as an indicator of cell proliferation.

d. Results: Peptides are evaluated on both the erythropoietin receptor cell line and the parental nonreceptor bearing cell line. In most cases, the peptide has been evaluated on a truncated human erythropoietin receptor cell line. Results are expressed as the amount of peptide necessary to yield one half of the maximal activity obtained with recombinant erythropoietin. Representative results are reported in tabular form with the relative binding data (See, Tables 17–21, infra.)

E. Tyrosine Phosphorylation: Peptide Induced Tyrosine Phosphorylation of Erythropoietin Receptor and Intracellular Proteins 1. Materials and Method a. Sample preparation: Peptide was resuspended in DMSO to yield a concentrate of $1\times10^{-2}$M.

b. Experimental Protocol: FDC-P1/muER cells maintained in RPMI 1640/10% Fetal Bovine Serum/antibiotics and 10 U/ml erythropoietin are grown to stationary phase. Cells are harvested and resuspended in fresh medium without growth factor (erythropoietin) for 24 hr. Cells are counted and resuspended at a concentration of 500,000 cells/ml. One milliliter of cells (500,000) are placed in an eppendorf tube. One microliter of a 1×10⁻³ peptide solution is added to the cells (final concentration 1×10⁻⁵M) and allowed to incubate for 10 minutes at 37° C. An erythropoietin control (final concentration 10 U/ml) was run with each assay. Cells are collected by centrifugation at 14,000 rpm 4° C. Cells are resuspended in 100 μl of SDS lysis buffer and subjected to SDS polyacrylamide gel electrophoresis. The gel is transferred to nitrocellulose and probed with an anti-phosphotyrosine antibody (Upstate Biotechnology Incorporated) diluted 1:1000 for 1 hour. The membrane is washed with Tris buffered saline and reprobed with an anti-mouse peroxidase labeled antibody. Reactive proteins are visualized using the ECL western blotting reagents (Amersham).

c. Results: Erythropoietin binding to its receptor in an erythropoietin-responsive cell line induces tyrosine phosphorylation of both the receptor and numerous intracellular proteins, including Shc, vav and JAK2 kinase. Numerous peptides, including GGTYSCHFGPLTWVCKPQGG (SEQ ID NO:8), have been analyzed to assess their ability to mimic the response seen with erythropoietin. Active peptides, as judged by binding and proliferation criteria, elicit an identical phosphorylation pattern as that of erythropoietin in erythropoietin-responsive cells. These results implicate that active peptides elicit their response through an erythropoietin-induced signal transduction pathway. Results are reported in tabular form with the binding and proliferation data (See, Tables 17–21, infra).

F. Cellular response kinetics: Peptide-Induced Initiation of Cell Cycle Measured By DNA Content 1. Experimental Protocol: FDCP-1/muER cells were grown to stationery phase≈3.0×10⁶ cells/ml. The cells were collected and resuspended in fresh medium in the absence of factor and allowed to grow for an additional 18 hr at which point the cells were divided into three flasks of equal cell density: −factor, +EPO and +peptide. Cells were then stimulated with either 10 U/ml EPO or 10 μM peptide. Three million cells were collected at the following time points: 0, 6, 8, 10, and 12 hr. (see, FIG. 15). Cells were washed twice in cold PBS and fixed by resuspending the cell pellet in 100 μl of cold PBS followed by 900 μl of cold 70% ethanol. Cells were stained with 50 μg/ml of propidium iodine and fluorescence was measured on FACS Scan Flow cytometer. The percentage of cells in each phase was measured using the SOBR model of CellFIT software, by Becton Dickinson. Erythropoietin (10 U/ml) and GGTYSCHFGPLTWVCKPQGG (SEQ ID NO:8) (1×10⁻⁵M) are equally effective at progressing cells through the cell cycle. By ten hours postinduction by either erythropoietin or peptide, approximately 45% of cells are in S phase as compared to the medium control of 15%. This result suggests that the peptide is able to elicit its response with the same kinetics as recombinant erythropoietin.

G. Colony Assay: Murine Bone Marrow and Human Peripheral Blood Colony Assay

1. Materials and Methods:

A ten milliliter sample of peripheral blood was obtained from a healthy individual in a standard sterile heparin vacutainer tube. Murine bone marrow was obtained from the femurs of approximately 10 mice per experiment. All reagents were obtained from Stem Cell Technologies Inc. (Vancouver, Canada).

a. Experimental Protocol: Briefly, a nucleated cell count was performed to establish the number and concentration of nucleated cells in the original sample. In the case of peripheral blood, the sample is subjected to centrifugation through a Ficoll-Hypaque (1.077 g per ml) gradient at 400 g for 30 minutes at room temperature. Mononuclear cells at the interface of the Ficoll-Hypaque solution are carefully removed and diluted to a total volume of about 10 ml. The cells obtained from murine bone marrow or human peripheral blood were collected by centrifugation and the supernatant was decanted. The pelleted cells were resuspended in fresh medium and subjected to collection as described above. The washed cells were diluted in Iscove's medium/ 2% fetal bovine serum to the following concentration for plating:

Normal marrow: 1×10⁵ light density cells

Normal blood: 4×10⁵ light density cells

Cells were added to methyl cellulose per directions of the manufacturer. Peptides were assayed at the following final concentrations: 1×10−6 and 1×10−5M in a "minus EPO" methylcellulose medium. Equivalent cell numbers were plated in "Complete" methylcellulose medium to assess maximal colony formation. A control plate was run with each assay minus EPO and peptide to determine background colony formation. Colonies were scored after both 10 days and 18 days of incubation.

b. Results: As shown in Tables 13–15, GGTYSCHFGPLTWVCKPQGG (SEQ ID NO:8) was able to promote colony formation, albeit at significantly lower levels as compared to that obtained on "Complete" methylcellulose medium (Erythropoietin 3 U/ml), in both murine bone marrow and human peripheral blood.

TABLE 13

COLONY ASSAY ON A HUMAN PERIPHERAL BLOOD SPECIMEN (DONOR: MALE) (SET UP DATE: 2/10/94)

| DATE | SAMPLE | CFU-E | MBFU-E | PBFU-E | CFU-GM |
|---|---|---|---|---|---|
| 2/23/94 | ZERO | X | X | X | X |
| | DMSO | X | X | X | X |
| | EPO (METHOCULT) | 11 | 25 | X | X |
| | EPO (3U/m1) | 7 | 7 | X | X |
| | AFFY 244 10⁻⁵M | 10 | 5 | X | X |
| | AFFY 244 10⁻⁶M | 11 | 5 | X | X |
| 3/4/94 | ZERO | X | X | X | X |
| | DMSO | X | X | X | X |
| | EPO (METHOCULT) | 1 | 11 | 13 | 9 |
| | EPO(3U/ml) | 4 | 7 | 7 | 3 |
| | AFFY 244 10⁻⁵M | 7 | 9 | 2 | 4 |
| | AFFY 244 10⁻⁶M | 6 | 11 | 1 | 2 |

CFU-E: COLONY-FORMING UNIT-ERYTHROID (1–2 CLUSTERS)
MBFU-E: MATURE BURST-FORMING UNIT-ERYTHROID (3–8 CLUSTERS)
PBRU-E: PRIMITIVE BURST-FORMING UNiT-ERYTHROID (9 OR MORE)
CFU-GM: COLONY-FORMING UNIT GRANULOCYTIC/MONOCYTE/ MACROPHAGE

TABLE 14

Colony-Forming Cell Numbers (Murine Bone Marrow) 1/28/94

| | | | AFFY1115/AFFY 244 | |
|---|---|---|---|---|
| Progenitor | Control | EPO | 10⁻⁵M | 10⁻⁶M |
| | | 2/10/94 | | |
| CFU-E | 0 | 23 | 2 | 3 |
| BFU-E | 0 | 5 | 0 | 0 |

TABLE 14-continued

Colony-Forming Cell Numbers (Murine Bone Marrow) 1/28/94

| | | | AFFY1115/AFFY 244 | |
|---|---|---|---|---|
| Progenitor | Control | EPO | $10^{-5}$M | $10^{-6}$M |
| CFU-GM | 0 | 3 | 0 | 0 |
| | | 2/21/94 | | |
| CFU-E | 0 | 0 | 0 | 0 |
| BFU-E | 0 | 30 | 2 | 4 |
| CFU-GM | 0 | 3 | 0 | 0 |

AFFY11157 = ggTYSCHFGPLTWVCKPQgg (SEQ ID NO: 8)

TABLE 15

Colony-Forming Cell Numbers (Murine Bone Marrow) 2/21/94

| | | | AFFY1115/AFFY 244 | |
|---|---|---|---|---|
| Progenitor | Control | EPO | $10^{-5}$M | $10^{-6}$M |
| | | 3/1/94 | | |
| CFU-E | 0 | 3 | 9 | 0 |
| BFU-E | 0 | 3 | 12 | 0 |
| CFU-GM | 0 | >10 | 0 | 0 |
| | | 3/14/94 | | |
| CFU-E | 0 | 0 | 1 | 0 |
| PBFU-E | 0 | 10 | 8 | 0 |
| MBFU-E | 0 | 0 | 4 | 0 |
| CFU-GM | 0 | 26 | 0 | 0 |

H. Peptide-Induced Proliferation: Peptide-Dependent Growth on Cell Lines Not Responsive to Erythropoietin a. Experimental protocol: Peptides were assayed as described in Section D, supra. A growth curve was performed on each cell line using the relevant mitogen/growth factor for each cell line to assess growth potential.

b. Results: As shown in Table 16, GGTYSCHFG-PLTWVCKPQGG (SEQ ID NO:8) was unable to stimulate a growth response on non-erythropoietin responsive cell lines including both hematopoietic and non-hematopoietic cell lines.

TABLE 16

Cell Proliferation Assays with 61233

| Cell type | Species | EPO | 61233 | Growth factor response |
|---|---|---|---|---|
| hematopietic | | | | |
| TF-1 | human | + | + | GM-CSF, IL3 (erythroid) |
| M-07E | human | – | – | GM-CSF, IL3 (megakaryoblastic) |
| AML193 | human | – | – | GM-CSF, G-CSF, IL3 (monocytic) |
| T-cell clone | human | ND | – | IL2 |
| osteoblastic | | | | |
| TE85 | human | – | – | serum |
| MC3T3 | murine | – | – | serum |
| breast cell | | | | |
| T47D | human | ND | – | progestin |

I. Immobilized EBP Based [$^{125}$I]EPO Competition Binding Assay.

The extracellular domain of the human erythropoietin receptor (EPO binding protein, EBP) has been expressed and overproduced in E. coli. As with many other recombinant eukaryotic proteins used in E. coli, the protein appeared as an insoluble product in laboratory scale fermentations and was refolded and purified to obtain active protein. EBP as produced by this method contains one free sulfhydryl group which can be modified without effecting the solution phase binding of ligand. In order to immobilize the EBP for equilibrium binding analysis and as the basis for a competition binding assay, this observation was extended for the covalent attachment of EBP to agarose beads. The iodoacetyl activation chemistry of Sufolink beads (Pierce Chemical Co, Rockford, Ill.) is specific for free thiols and assures that the linkage is not easily reversible. EBP-Sulfolink beads were made as follows: SulfoLink gel suspension (10 ml) was mixed with coupling buffer (40 ml: 50 mM Tris, pH 8.3, 5 mM EDTA) and the gel was allowed to settle. The supernatant was removed and the EBP (0.3–1 mg/ml in coupling buffer) to be bound was added directly to the washed beads. The mixture was rocked gently for 30 minutes at room temperature, and the beads were allowed to settle for 1 hour at room temperature. The supernatant was removed and retained, and the beads were washed twice with 20 ml of coupling buffer. The washes were recovered as well. The beads were then treated with 20 ml of 0.05M cysteine for 30 minutes at room temperature to block unbound sites. Finally, the beads were washed with 50 ml of 1M NaCl, then with 30 ml of PBS, and resuspended in 20 ml of PBS and stored at 4° C. for later use. The amount of EBP which was covalently bound to the beads was determined by comparing the $OD_{280}$ of the original EBP solution to the total $OD_{280}$ recovered in the reaction supernatant and the two 20 ml washes. Typically, 40–60% of the applied EBP remains associated with the beads.

Binding assays were initiated by the addition of EBP beads (50 µl) to individual reaction tubes. Total binding was measured in tubes containing 0.3–30 nM $^{125}$I-EPO (NEN Research Products, Boston Mass., 100 µCi/µg). For determination of non-specific binding, unlabelled EPO was added at a level of 1000 fold in excess of the corresponding [$^{125}$I]EPO concentration. Each reaction volume was brought to 500 µl with binding buffer (PBS/0.2% BSA). The tubes were incubated for five hours (a time period experimentally determined as adequate for the establishment of equilibrium) at room temperature with gentle rocking. After five hours, each reaction mixture was passed through a 1 ml pipet tip plugged with glass wool. The tubes were washed with 1 ml wash buffer (PBS/5% BSA) and this volume, as well as 2 additional 1 ml washes, were passed through the pipet tip and collected for determination of the free EPO concentration. Equilibrium binding analysis of the specific association of [$^{125}$I]EPO with EBP immobilized on these agarose beads indicates a Kd of 5 nM±2 based on a linear transformation (Scatchard) of the binding isotherm (see, FIG. 16).

Competitive binding analysis assays of candidate peptides were performed as outlined below. Individual peptides were dissolved in DMSO to prepare a stock solution of 1 mM. All reaction tubes (in duplicate) contained 50 µL of EBP beads, 0.5 nM [$^{125}$I]EPO and 0–500 µM peptide in a total of 500 µL binding buffer. The final concentration of DMSO was adjusted to 2.5% in all assay tubes, a value without detectable effect since an examination of the sensitivity of the assay to DMSO demonstrated that concentrations of up to 25% DMSO (V/V) had no deleterious effect on binding. Non-specific binding was measured in each individual assay by inclusion of tubes containing a large excess of unlabelled EPO (1000 nM). Initial assay points with no added peptide were included in each assay to determine total binding.

Binding mixtures were incubated overnight at room temperature with gentle rocking. The beads were then collected using Micro-columns (Isolab, Inc., Akron, Ohio) and washed with 3 mL of wash buffer. The columns containing the washed beads were placed in 12×75 mm glass tubes and bound radioactivity levels were determined using a gamma counter. The amount of bound [$^{125}$I]EPO was expressed as a percentage of the control (total=100%) binding and plotted versus the peptide concentration after correction for non-specific binding. The $IC_{50}$ was defined as the concentration of peptide which reduced the binding of [$^{125}$I]EPO to the EBP beads by 50%. All data are reported as relative to GGTYSCHFGPLTWVCKPQGG (SEQ ID NO:8) (RWJ61233) which demonstrated an $IC_{50}$ of 5 μM (see, Tables 17–21, infra).

TABLE 17

GGTYSCHFGPLTWVCKPQGG (SEQ ID NO: 8) Substitution Series

| SEQ ID NO; | RWJ NO: | Sequence | Relative Binding‡ | EPO-ED$_{50}$ (μM) | Phosphorylation[1] |
|---|---|---|---|---|---|
| 8 | 61233※ | GGTYSCHFGPLTWVCKPQGG | 1 | 0.1 | + |
| 52 | 61231 | GGTASCHFGPLTWVCKPQGG | 24 | IA | − |
| 189 | 61520 | GGTTSCHFGPLTWVCKPQGG | 24 | IA | − |
| 190 | 61598 | GGTFSCHFGPLTWVCKPQGG | 12 | IA | − |
| 191 | 61277 | GGTYSCHFGALTWVCKPQGG | 2 | 0.1 | + |
| 192 | 61278 | GGTYSCHFGPLAWVCKPQGG | 18 | IA | − |
| 193 | 61313 | GGTYSCHFAPLTWVCKPQGG | 16 | IA | − |
| 194 | 61314 | GGTYSCHFGPATWVCKPQGG | 1 | .2 | + |
| 195 | 61395 | GGTYSCHFGPLTAVCKPQGG | >100 | IA | − |
| 196 | 62145 | GGTYSCHFGPLTFVCKPQGG | 6 | 0.25 | |
| 244 | 61530 | GGTYSC-FGPLTWVCKPQGG | 40 | IA | − |

*Amount required to achieve the half maximal level of EPO dependent proliferation (11 pM)
[1]Assayed at 10 μM
[2]IA = inactive
‡Binding relative to RWJ-61233
※Note that all peptides are cyclic (except 61394) and were analyzed as COOH terminal amides (—CONH$_2$)
61233 = AFFY11157 = =AF11157 AFFY 244

TABLE 18

GGTYSCHFGPLTWVCKPQGG (SEQ ID NO: 8) Truncation Series

| SEQ ID NO: | RWJ No. | Sequence | Relative Binding‡ | EPO-ED$_{50}$ (μM) | Phosphorylation[1] |
|---|---|---|---|---|---|
| 8 | 61233※ | GGTYSCHFGPLTWVCKPQGG | 1 | 0.1 | + |
| 13 | 61596 | GGTYSCHFGPLTWVCKPQ | 1.6 | 0.08 | + |
| 245 | 61597 | TYSCHFGPLTWVCKPQGG | 8 | 2 | + |
| 197 | 61230 | TYSCHFGPLTWVCKPQ | 6 | 2 | + |
| 198 | 61232 | YSCHFGPLTWVCKP | 9 | 20 | +/− |
| 16 | 61279 | YSCHFGPLTWVCK | 14 | 3 | +/− |
| 246 | 61477 | YSCHFGPLTWVC | 50 | IA[2] | − |
| 199 | 61895 | YSCHFGALTWVCK | 32 | IA | − |
| 17 | 61513 | Y-CHFGPLTWVC | 12 | 2 | + |
| 200 | 61177 | SCHFGPLTWVCK | 18 | IA | − |
| 19 | AF11154 | GGCRIGPITWVCGG | 13 | IA | − |
| 201 | 61394 | HFGPLTWV | >100 | IA | − |

*Amount required to achieve the half maximal level of EPO dependent proliferation (11 pM)
[1]Assayed at 10 μM
[2]IA = inactive
‡Binding relative to RWJ-61233
※Note that all peptidse are cyclic (except 61394) and were analyzed as COOH terminal amides (—CONH$_2$)
61233 = AFFY11157 = =AF11157 AFFY244

TABLE 19

Sequence Analog Peptides

| SEQ ID NO: | RWJ No. | Sequence | Relative Bonding‡ | EOP-ED$_{50}$ (μm) | Phosphorylation[1] |
|---|---|---|---|---|---|
| 8 | 61233※ | GGTYSCHFGPLTWVCKPQGG | 1 | 0.1 | + |

TABLE 19-continued

Sequence Analog Peptides

| SEQ ID NO: | RWJ No. | Sequence | Relative Bonding‡ | EOP-ED$_{50}$ ($\mu$m) | Phosphorylation[1] |
|---|---|---|---|---|---|
| 202 | 61721 | GGTYSEHFGPLTWVKKPQGG | >100 | IA[2] | |
| 14 | 61718 | GGLYACHMGPMTWVCQPLRG | O.6 | 0.1 | |
| 57 | 61719 | GGEYLCRMGPMTWVCTPVGG | 8 | 9 | |
| 59 | 61720 | GGLYTCRMGPITWVCLPAGG | ND | — | |
| 53 | 61717 | GGNYYCRFGPITFECHPTGG | >100 (S1) | IA | |

*Amount required to achieve the half maximal level of EPO dependent proliferation (11 pM)
[1]Assayed at 10 $\mu$M;
[2]IA = inactive
‡Binding relative to RWJ-61233
*Note that all peptides are cyclic (except 61394) and were analyzed as COOH terminal amides (—CONH$_2$)
61233 = AFFY11157 = AFF11157 = AFFY244

TABLE 20

Position #4 Substitution Series

| | | | | EOP-ED$_{50}$ ($\mu$M)* | |
|---|---|---|---|---|---|
| RWJ No. | (X) | Sequence | Relative Binding‡ | murine receptor | truncated human receptor |
| 61233‡ | | GGTYSCHFGPLTWVCKPQGG | 1 | 0.1 | 0.1 |
| 61231 | | GGTASCHFGPLTWVCKPQGG | 24 | IA[2] | |
| 61520 | | GGTTSCHFGPLTWVCKPQGG | 24 | IA | |
| 61598 | | GGTFSCHFGPLTWVCKPQGG | 12 | IA | |
| 61894 | p-NO$_2$—Phe | GGTXSCHFGPLTWVCKPQGG | 17 | IA | 0.8 |
| 62019 | p-NH$_2$—Phe | GGTXSCHFGPLTWVCKPQGG | 18 | IA | 3.0 |
| 62020 | p-F—Phe | GGTXSCHFGPLTWVCKPQGG | 8 | 1.0 | 0.1 |
| 62021 | 3,5-dibromo-tyr | GGTXSCHFGPLTWVCKPQGG | 30 | IA | IA |

*Amount required to achieve the half maximal level of EPO dependent proliferation (11 pM)
[1]ND = Not determined
[2]IA = Inactive
‡Binding relative to RWJ-61233
Note that all peptides are cyclic and were analyzed as COOH terminal amides (—CONH$_2$)
61233 = AFFY11157 = AFF11157 = AFFY244

TABLE 21

Differential Activity Series-GGTYSCHFGPLTWVCKPQGG (SEQ ID NO: 8) Based

| | | | | EPO-ED$_{50}$ ($\mu$M)* | |
|---|---|---|---|---|---|
| SEQ ID NO: | RWJ No. | Sequence | Relative Binding‡ | murine receptor | truncated human receptor |
| 8 | 61233‡ | GGTYSCHFGPLTWVCKPQGG | 1 | 0.1 | 0.1 |
| 13 | 61596 | GGTYSCHFGPLTWVCKPQ | 1.6 | 0.08 | 0.02 |
| 14 | 61718 | GGLYACHMGPMTWVCQPLRG | O.6 | 0.1 | 0.08. |
| 14 | AF11288 | GGLYACHMGPMTWVCQPLRG | 0.2 | 0.15 | ND[1] |
| 21 | 61757 (H22) | LGRKYSCHFGPLTWVCQPAKKD | 1 | 0.11 | 0.15 |
| 15 | AF11654 | TIAQYICYMGPETWECRPSPKA | 1 | 0.2 | 0.02 |
| 251 | 62145 | GGTYSCHFGPLTFVCKPQGG | 6 | 0.25 | 0.5 |
| 18 | 62146 | Ac-GGTYSCHFGPLTWVCKPQGG | 4 | 0.03 | 0.06 |
| 247 | 61894 | GGTXSCHFGPLTWVCKPQGG p-NO$_2$—Phe | 17 | IA[2] | 0.8 |
| 248 | 62019 | GGTXSCHFGPLTWVCKPQGG p-NH$_2$—Phe | 18 | IA | 3.0 |
| 249 | 62020 | GGTXSCHFGPLTWVCKPQGG p-F—Phe | 8 | 1.0 | 0.1 |

*Amount required to achieve the half maximal level of EPO dependent prolifeiation (11 pM)

TABLE 21-continued

Differential Activity Series-GGTYSCHFGPLTWVCKPQGG (SEQ ID NO: 8) Based

| SEQ ID NO: | RWJ No. | Sequence | Relative Binding[‡] | EPO-ED$_{50}$ ($\mu$M)* murine receptor | truncated human receptor |
|---|---|---|---|---|---|

[1]ND = Not determined
[2]IA = Inactive
[‡‡‡] Binding relative to RWJ-61233
Note that all peptides are cyclic and were analyzed as COOH terminal amides (—CONH$_2$)
61233 = AFFY11157 = AF11157 = AFFY244

J. Polycythemic Exhypoxic Mouse Bioassay

Female BDF1 mice (18–20 gms) are subjected to a conditioning cycle (in hypobaric chambers) of 18 hrs. at 0.40±0.02 atm. and 6 hrs. at ambient pressure for a period of 14 days.

Mice are maintained at ambient pressure for 72 hrs prior to administration of r-HuEPO or test samples. Test samples or r-HuEPO standard are diluted for injection into conditioned mice. The vehicle consists of: PBS containing 0.1% BSA (w/v). For each dilution, 0.5 ml is administered subcutaneously into each of 10 mice. $^{59}$Fe is administered 48 hrs. later. Blood samples are taken 48 hrs. following administration of $^{59}$Fe. Hematocrits and radioactivity measurements are determined for each sample. Dose range and results (two different assays) are set forth in Table 22 and FIGS. 17A–17C, infra.

TABLE 22

|  | DOSE | n | LOG MEAN |
|---|---|---|---|
| EPO St. | 0.000 U | 10 | 0.26 |
|  | 0.025 | 10 | 1.65 |
|  | 0.050 | 10 | 2.74 |
|  | 0.100 | 10 | 3.28 |
| DMSO | 1.40% | 7 | 0.58 |
|  | 0.35% | 5 | 0.60 |
| 244-1 | 0.25 $\mu$g | 7 | 0.62 |
|  | 0.50 | 8 | 0.76 |
|  | 1.00 | 9 | 0.92 |
| 244-2 | 2.00 | 9 | 1.38 |
|  | 4.00 | 10 | 1.81 |
|  | 8.00 | 9 | 2.26 |
| 244-3 | 14.0 | 10 | 2.44 |
|  | 28.0 | 10 | 3.15 |
|  | 56.0 | 9 | 3.16 |

0.1 mg AFFY244 ≈ 1 U r-HuEPO (8.3 ng)

In addition, using the foregoing polycythemic exhypoxic mouse bioassay, TIAQYICYMGPETWECRPSPKA (SEQ ID NO:15) and a dimeric peptide analog of GGTYSCHFGPLTWVCKPQGG (SEQ ID NO:8) containing two disulfide bonds (AF12080) were tested. The results of the polycythemic exhypoxic mouse bioassay are set forth in FIGS. 18A–18B. In addition, Table 23, infra, sets forth the approximate equivalency of EPO and various mimetic peptides.

TABLE 23

| SEQ ID NO: | Peptide | Amount of Peptide Equivalent to 0.025 units of EPO (nmol) |
|---|---|---|
| 8 | GGTYSCHFGPLTWVCKPQGG (RWJ 61233/AFFY11157) | 3.8 |
| 13 | GGTYSCHFGPLTWVCKPQ (RWJ 61596) | 0.5 |
| 21 | LGRKYSCHFGPLTWVCQPAKKD (RWJ 61757) | 3.1 |
| 15 | TIAQYICYMGPETWECRPSPKA (AFFY11654) | 11–21 |
| 8 | GGTYSCHFGPLTWVCKPQGG Dimer (AFFY12080) | 0.035 |

K. Reticulocyte Assay

Normal untreated female BDF1 mice are dosed (0.5 ml, S.Q.) on three consecutive days with either EPO or experimental compound. The vehicle: PBS, 10% PEG 8000, 0.25% BSA, with DMSO being added. At day three, mice are also dosed (0.1 ml, I.P.) with iron dextran (100 mg/ml). At day five, mice are anesthetized with $CO_2$ and bled by cardiac puncture. % reticulocytes is determined by thiazole orange staining and flow cytometer analysis (retic-count program). Hematocrits are manually determined. The percent of corrected reticulocytes is determined using the following formula:

$$\%RETIC_{(CORRECTED)} = \%RETIC_{(OBSERVED)} \times Hct_{(INDIVIDUAL)}/Hct_{(NORMAL)}$$

The results obtained using the foregoing reticulocyte assay are set forth in FIGS. 18A–18B and FIGS. 19A–19B.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled. The disclosures of all articles and references, including patent publications, are incorporated herein by reference.

What is claimed:

1. A method for treating a patient having a disorder characterized by a deficiency of erythropoietin or a low or defective red blood cell population comprising administering to the patient a therapeutically effective amount of a peptide of 10 to 40 amino acid residues in length that binds to erythropoietin receptor and comprises a sequence of amnio acids $X_3X_4X_5GPX_6TWX_7X_8$ (SEQ ID NO:1) where each amino acid is indicated by standard one letter abbreviation; $X_6$ is independently selected from any one of the 20 genetically coded L-amino acids; $X_3$ is C; $X_4$ is R, H, L, or W; $X_5$ is M, F, I; $X_7$ is D, E, I, L, or V; and $X_8$ is C.

2. The method of claim 1 wherein the disorder is end-stage renal failure or dialysis; anemia associated with AIDS, auto immune disease, or malignancies; beta-thalassemia; cystic fibrosis; early anemia of prematurity; anemia associated with chronic inflammatory diseases; spinal cord injury; acute blood loss; aging; and neoplastic disease states accompanied by abnormal erythropoiesis.

3. The method of claim 2 wherein the peptide comprises a sequence of amino acids $YX_2X_3X_4X_5GPX_6TWX_7X_8$ (SEQ ID NO:253) where each amino acid is indicated by standard one letter abbreviation; each $X_2$ and $X_6$ is independently selected from any one of the 20 genetically coded L-amino acids; $X_3$ is C; $X_4$ is R, H, L, or W; $X_5$ is M, F, or I; $X_7$ is D, E, I, L, or V; and $X_8$ is C.

4. The method of claim 3 wherein the peptide comprises a sequence of amino acids $X_1YX_2X_3X_4X_5GPX_6TWX_7X_8X_9X_{10}X_{11}$ (SEQ ID NO:254) where each amino acid is indicated by standard one letter abbreviation; each $X_1$, $X_2$, $X_6$, $X_9$, $X_{10}$, and $X_{11}$, is independently selected from any one of the 20 genetically coded L-amino acids; $X_3$ is C; $X_4$ is R, H, L, or W; $X_5$ is M, F, or I; $X_7$ is D, E, I, L, or V; and $X_8$ is C.

5. The method of claim 4 wherein $X_4$ is R or H; $X_5$ is F or M; $X_6$ is I, L, T, M, or V; $X_7$ is D or V; $X_9$ is G, K, L, Q, R, S, or T; and $X_{10}$ is A, G, P, R, or Y.

6. The method of claim 5 wherein $X_1$ is D, E, L, N, S, T, or V; $X_2$ is A, H, K, L, M, S, or T; $X_4$ is R or H; $X_9$ is K, R, S, or T; and $X_{10}$ is P.

7. The method of claim 2 wherein the peptide is GGTYSCHFGPLTWVCKPQGG (SEQ ID NO:8).

* * * * *